United States Patent
McCarthy et al.

(10) Patent No.: US 7,189,199 B2
(45) Date of Patent: *Mar. 13, 2007

(54) METHODS AND DEVICES FOR IMPROVING CARDIAC FUNCTION IN HEARTS

(75) Inventors: Patrick M. McCarthy, Hunting Valley, OH (US); Cyril J. Schweich, Jr., St. Paul, MN (US); Todd J. Mortier, Minneapolis, MN (US); Peter T. Keith, St. Paul, MN (US); Michael J. Kallok, New Brighton, MN (US)

(73) Assignee: Myocor, Inc., Maple Grove, MN (US)

( * ) Notice: Subject to any disclaimer, the term of this patent is extended or adjusted under 35 U.S.C. 154(b) by 576 days.

This patent is subject to a terminal disclaimer.

(21) Appl. No.: 10/136,446

(22) Filed: May 2, 2002

(65) Prior Publication Data
US 2002/0169359 A1   Nov. 14, 2002

Related U.S. Application Data

(63) Continuation of application No. 09/422,328, filed on Oct. 21, 1999, now Pat. No. 6,406,420, which is a continuation-in-part of application No. 09/124,286, filed on Jul. 29, 1998, now Pat. No. 6,045,497, which is a continuation-in-part of application No. 08/933,456, filed on Sep. 18, 1997, now Pat. No. 5,961,440, which is a continuation-in-part of application No. 08/778,277, filed on Jan. 2, 1997, now Pat. No. 6,050,936.

(51) Int. Cl.
*A61F 1/00* (2006.01)
(52) U.S. Cl. ............................................. 600/16; 600/37
(58) Field of Classification Search .................. 600/16, 600/37; 623/2.1, 2.33, 2.36, 3.1; 606/151; 128/898
See application file for complete search history.

(56) References Cited

U.S. PATENT DOCUMENTS

| | | | |
|---|---|---|---|
| 963,899 A | 7/1910 | Kistler | |
| 3,019,790 A | 2/1962 | Militana | |
| 3,656,185 A | 4/1972 | Carpentier | |
| 3,980,068 A | 9/1976 | Karsten et al. | |
| 4,035,849 A | 7/1977 | Angell et al. | |
| 4,055,861 A | 11/1977 | Carpentier et al. | |
| 4,192,293 A | 3/1980 | Asrican | 600/18 |
| 4,217,665 A | 8/1980 | Bex et al. | |

(Continued)

FOREIGN PATENT DOCUMENTS

| | | |
|---|---|---|
| DE | 36 14 292 | 11/1987 |
| DE | 42 34 127 | 5/1994 |
| DE | 296 19 294 | 8/1997 |

(Continued)

OTHER PUBLICATIONS

Freeman, Leonard M., M.D., et al, Seminars in Nuclear Medicine, *The Heart*, vol. III, No. 2, Apr. 1973.

(Continued)

*Primary Examiner*—Jeffrey R. Jastrzab
(74) *Attorney, Agent, or Firm*—Finnegan, Henderson, Farabow, Garrett & Dunner, L.L.P.

(57) ABSTRACT

Various methods and devices are disclosed for improving cardiac function in hearts having zones of infarcted (akinetic) and aneurysmal (dyskinetic) tissue regions. The methods and devices reduce the radius of curvature in walls of the heart proximal infarcted and aneurysmal regions to reduce wall stress and improve pumping efficiency. The inventive methods and related devices include splinting of the chamber wall proximal the infarcted region and various other devices and methods including suture and patch techniques.

37 Claims, 25 Drawing Sheets

U.S. PATENT DOCUMENTS

| | | | |
|---|---|---|---|
| 4,261,342 A | 4/1981 | Aranguren Duo | 128/1 |
| 4,300,564 A | 11/1981 | Furihata | |
| 4,306,319 A | 12/1981 | Kaster | |
| 4,343,048 A | 8/1982 | Ross et al. | |
| 4,372,293 A | 2/1983 | Vijil-Rosales | 128/1 |
| 4,409,974 A | 10/1983 | Freedland | 128/92 |
| 4,536,893 A | 8/1985 | Parravicini | 623/3 |
| 4,579,120 A | 4/1986 | MacGregor | |
| 4,592,342 A | 6/1986 | Salmasian | |
| 4,629,459 A | 12/1986 | Ionescu et al. | |
| 4,690,134 A | 9/1987 | Snyders | 128/64 |
| 4,705,040 A | 11/1987 | Mueller et al. | |
| 4,936,857 A | 6/1990 | Kulik | 623/3 |
| 4,944,753 A | 7/1990 | Burgess et al. | 623/16 |
| 4,960,424 A | 10/1990 | Grooters | 623/2 |
| 4,997,431 A | 3/1991 | Isner et al. | 606/15 |
| 5,061,277 A | 10/1991 | Carpentier et al. | |
| 5,104,407 A | 4/1992 | Lam et al. | |
| 5,106,386 A | 4/1992 | Isner et al. | 606/15 |
| 5,131,905 A | 7/1992 | Grooters | 600/16 |
| RE34,021 E | 8/1992 | Mueller et al. | 604/51 |
| 5,156,621 A | 10/1992 | Navia et al. | |
| 5,169,381 A | 12/1992 | Snyders | 600/16 |
| 5,192,314 A | 3/1993 | Daskalakis | 623/3 |
| 5,250,049 A | 10/1993 | Michael | 606/72 |
| 5,258,015 A | 11/1993 | Li et al. | |
| 5,284,488 A | 2/1994 | Sideris | 606/213 |
| 5,300,087 A | 4/1994 | Knoepfler | |
| 5,312,642 A | 5/1994 | Chesterfield et al. | |
| 5,360,444 A | 11/1994 | Kusuhara | |
| 5,376,112 A | 12/1994 | Duren | |
| 5,385,528 A | 1/1995 | Wilk | 600/18 |
| 5,389,096 A | 2/1995 | Aita et al. | |
| 5,417,709 A | 5/1995 | Slater | |
| 5,433,727 A | 7/1995 | Sideris | 606/213 |
| 5,445,600 A | 8/1995 | Abdulla | |
| 5,450,860 A | 9/1995 | O'Connor | 128/898 |
| 5,452,733 A | 9/1995 | Sterman et al. | 128/898 |
| 5,458,574 A | 10/1995 | Machold et al. | 604/101 |
| 5,496,305 A | 3/1996 | Kittrell et al. | 606/15 |
| 5,509,428 A | 4/1996 | Dunlop | 128/898 |
| 5,522,884 A | 6/1996 | Wright | |
| 5,533,958 A | 7/1996 | Wilk | 600/18 |
| 5,571,215 A | 11/1996 | Sterman et al. | 623/66 |
| 5,584,803 A | 12/1996 | Stevens et al. | 604/4 |
| 5,593,424 A | 1/1997 | Northrup III | 606/232 |
| 5,607,471 A | 3/1997 | Seguin et al. | |
| 5,665,092 A | 9/1997 | Mangiardi et al. | |
| 5,674,279 A | 10/1997 | Wright et al. | |
| 5,682,906 A | 11/1997 | Sterman et al. | 128/898 |
| 5,702,343 A | 12/1997 | Alferness | 607/37 |
| 5,713,954 A | 2/1998 | Rosenberg et al. | |
| 5,718,725 A | 2/1998 | Sterman et al. | 623/2 |
| 5,755,783 A | 5/1998 | Stobie et al. | |
| 5,758,663 A | 6/1998 | Wilk et al. | |
| 5,766,234 A | 6/1998 | Chen et al. | |
| 5,776,189 A | 7/1998 | Khalid et al. | |
| 5,800,334 A | 9/1998 | Wilk | 600/18 |
| 5,800,528 A | 9/1998 | Lederman et al. | 623/3 |
| 5,800,531 A | 9/1998 | Cosgrove et al. | |
| 5,807,384 A | 9/1998 | Mueller | |
| 5,814,097 A | 9/1998 | Sterman et al. | 623/2 |
| 5,824,066 A | 10/1998 | Gross | |
| 5,824,069 A | 10/1998 | Lemole | |
| 5,840,059 A | 11/1998 | March et al. | |
| 5,849,005 A | 12/1998 | Garrison et al. | 606/1 |
| 5,855,601 A | 1/1999 | Bessler et al. | |
| 5,855,614 A | 1/1999 | Stevens et al. | 623/11 |
| 5,865,791 A | 2/1999 | Whayne et al. | 604/49 |
| 5,876,436 A | 3/1999 | Vanney et al. | |
| 5,888,240 A | 3/1999 | Carpentier et al. | |
| 5,902,229 A | 5/1999 | Tsitlik et al. | 600/46 |
| 5,928,281 A | 7/1999 | Huynh et al. | |
| 5,944,738 A | 8/1999 | Amplatz et al. | |
| 5,957,977 A | 9/1999 | Melvin | 623/3 |
| 5,961,440 A | 10/1999 | Schweich, Jr. et al. | 600/16 |
| 5,961,539 A | 10/1999 | Northrup, III et al. | |
| 5,961,549 A | 10/1999 | Nguyen et al. | |
| 5,967,990 A | 10/1999 | Thierman et al. | |
| 5,971,910 A | 10/1999 | Tsitlik et al. | 600/16 |
| 5,971,911 A | 10/1999 | Wilk | |
| 5,972,022 A | 10/1999 | Huxel | 606/215 |
| 5,984,857 A | 11/1999 | Buck et al. | 606/16 |
| 5,984,917 A | 11/1999 | Fleischman et al. | |
| 5,999,678 A | 12/1999 | Murphy-Chutorian et al. | |
| 6,001,126 A | 12/1999 | Nguyen-Thien-Nhon | |
| 6,019,722 A | 2/2000 | Spence et al. | |
| 6,024,096 A | 2/2000 | Buckberg | 128/898 |
| 6,024,756 A | 2/2000 | Huebsch et al. | 606/213 |
| 6,045,497 A | 4/2000 | Schweich, Jr. et al. | 600/16 |
| 6,050,936 A | 4/2000 | Schweich, Jr. et al. | 600/37 |
| 6,059,715 A | 5/2000 | Schweich, Jr. et al. | 600/16 |
| 6,071,303 A | 6/2000 | Laufer | 607/96 |
| 6,077,214 A | 6/2000 | Mortier et al. | 600/16 |
| 6,077,218 A | 6/2000 | Alferness | 600/37 |
| 6,079,414 A | 6/2000 | Roth | 128/898 |
| 6,085,754 A | 7/2000 | Alferness et al. | 128/898 |
| 6,086,532 A | 7/2000 | Panescu et al. | |
| 6,095,968 A | 8/2000 | Snyders | 600/16 |
| 6,102,944 A | 8/2000 | Huynh et al. | |
| 6,110,100 A | 8/2000 | Talpade | 600/37 |
| 6,113,536 A | 9/2000 | Aboul-Hosn et al. | |
| 6,117,159 A | 9/2000 | Huebsch et al. | 606/213 |
| 6,120,520 A | 9/2000 | Saadat et al. | |
| 6,123,662 A | 9/2000 | Alferness et al. | 600/37 |
| 6,125,852 A | 10/2000 | Stevens et al. | 128/898 |
| 6,126,590 A | 10/2000 | Alferness | 600/37 |
| 6,129,758 A | 10/2000 | Love | |
| 6,132,438 A | 10/2000 | Fleischman et al. | |
| 6,143,025 A | 11/2000 | Stobie et al. | |
| 6,155,968 A | 12/2000 | Wilk | 600/16 |
| 6,155,972 A | 12/2000 | Nauertz et al. | 600/37 |
| 6,162,168 A | 12/2000 | Schweich, Jr. et al. | 600/16 |
| 6,165,119 A | 12/2000 | Schweich, Jr. et al. | 600/16 |
| 6,165,120 A | 12/2000 | Schweich, Jr. et al. | 600/16 |
| 6,165,121 A | 12/2000 | Alferness | 600/37 |
| 6,165,122 A | 12/2000 | Alferness | 600/37 |
| 6,165,183 A | 12/2000 | Kuehn et al. | |
| 6,169,922 B1 | 1/2001 | Alferness et al. | 607/5 |
| 6,174,279 B1 | 1/2001 | Girard | 600/37 |
| 6,174,332 B1 | 1/2001 | Loch et al. | |
| 6,179,791 B1 | 1/2001 | Krueger | 600/587 |
| 6,182,664 B1 | 2/2001 | Cosgrove | |
| 6,183,411 B1 | 2/2001 | Mortier et al. | |
| 6,183,512 B1 | 2/2001 | Howanec, Jr. et al. | |
| 6,190,408 B1 * | 2/2001 | Melvin | 623/3.1 |
| 6,193,648 B1 | 2/2001 | Krueger | 600/37 |
| 6,197,053 B1 | 3/2001 | Cosgrove et al. | |
| 6,206,004 B1 | 3/2001 | Schmidt et al. | |
| 6,206,820 B1 | 3/2001 | Kazi et al. | |
| 6,210,432 B1 | 4/2001 | Solem et al. | |
| 6,217,610 B1 | 4/2001 | Carpentier et al. | |
| 6,221,013 B1 | 4/2001 | Panescu et al. | |
| 6,221,103 B1 | 4/2001 | Melvin | |
| 6,221,104 B1 | 4/2001 | Buckberg et al. | |
| 6,224,540 B1 | 5/2001 | Lederman et al. | |
| 6,230,714 B1 | 5/2001 | Alferness et al. | |
| 6,231,561 B1 | 5/2001 | Frazier et al. | |
| 6,231,602 B1 | 5/2001 | Carpentier et al. | |
| 6,238,334 B1 | 5/2001 | Easterbrook, III et al. | |
| 6,241,654 B1 | 6/2001 | Alferness | |
| 6,245,102 B1 | 6/2001 | Jayaraman | |
| 6,245,105 B1 | 6/2001 | Nguyen et al. | |
| 6,250,308 B1 | 6/2001 | Cox | |

| | | | | | |
|---|---|---|---|---|---|
| 6,251,061 B1 | 6/2001 | Hastings et al. | 6,706,065 B2 | 3/2004 | Langberg et al. |
| 6,258,021 B1 | 7/2001 | Wilk | 6,709,456 B2 | 3/2004 | Langberg et al. |
| 6,258,023 B1 | 7/2001 | Rogers et al. | 6,712,804 B2 | 3/2004 | Roue et al. |
| 6,260,552 B1 | 7/2001 | Mortier et al. | 6,716,158 B2 | 4/2004 | Raman et al. |
| 6,260,820 B1 | 7/2001 | Chowdhury | 6,719,767 B1 | 4/2004 | Kimblad |
| 6,261,222 B1 | 7/2001 | Schweich, Jr. et al. | 6,723,038 B1 * | 4/2004 | Schroeder et al. ............ 600/16 |
| 6,264,602 B1 | 7/2001 | Mortier et al. | 6,726,716 B2 | 4/2004 | Marquez |
| 6,269,819 B1 | 8/2001 | Oz et al. | 6,726,717 B2 | 4/2004 | Alfieri et al. |
| 6,283,993 B1 | 9/2001 | Cosgrove et al. | 6,730,016 B1 | 5/2004 | Cox et al. |
| 6,290,674 B1 | 9/2001 | Roue et al. | 6,733,525 B2 | 5/2004 | Yang et al. |
| 6,309,370 B1 | 10/2001 | Haim et al. | 6,740,107 B2 | 5/2004 | Loeb et al. |
| 6,312,447 B1 | 11/2001 | Grimes | 6,752,813 B2 | 6/2004 | Goldfarb et al. |
| 6,314,322 B1 | 11/2001 | Rosenberg | 6,755,777 B2 | 6/2004 | Schweich, Jr. et al. |
| 6,328,727 B1 | 12/2001 | Frazier et al. | 6,755,779 B2 | 6/2004 | Vanden Hoek et al. |
| 6,331,157 B2 | 12/2001 | Hancock | 6,767,362 B2 | 7/2004 | Schreck |
| 6,332,863 B1 | 12/2001 | Schweich, Jr. et al. | 6,769,434 B2 | 8/2004 | Liddicoat et al. |
| 6,332,864 B1 | 12/2001 | Schweich, Jr. et al. | 6,776,754 B1 | 8/2004 | Wilk |
| 6,332,893 B1 | 12/2001 | Mortier et al. | 6,790,231 B2 | 9/2004 | Liddicoat et al. |
| 6,338,712 B2 | 1/2002 | Spence et al. | 6,793,673 B2 | 9/2004 | Kowalsky et al. |
| 6,360,749 B1 | 3/2002 | Jayaraman | 6,797,001 B2 | 9/2004 | Mathis et al. |
| 6,370,429 B1 | 4/2002 | Alferness et al. | 6,800,090 B2 | 10/2004 | Alferness et al. |
| 6,375,608 B1 | 4/2002 | Alferness | 6,814,700 B1 | 11/2004 | Mueller et al. |
| 6,379,366 B1 | 4/2002 | Fleischman et al. | 6,837,247 B2 | 1/2005 | Buckberg et al. |
| 6,402,679 B1 | 6/2002 | Mortier et al. | 6,875,224 B2 | 4/2005 | Grimes |
| 6,402,680 B2 | 6/2002 | Mortier et al. | 6,876,887 B2 | 4/2005 | Okuzumi |
| 6,406,420 B1 | 6/2002 | McCarthy et al. | 6,893,392 B2 | 5/2005 | Alferness |
| 6,409,760 B1 | 6/2002 | Melvin | 6,896,652 B2 | 5/2005 | Alferness et al. |
| 6,416,459 B1 | 7/2002 | Haindl | 2001/0003986 A1 | 6/2001 | Cosgrove |
| 6,419,669 B1 | 7/2002 | Frazier et al. | 2001/0014800 A1 | 8/2001 | Frazier et al. |
| 6,432,039 B1 | 8/2002 | Wardle | 2001/0014811 A1 | 8/2001 | Hussein |
| 6,432,059 B2 | 8/2002 | Hickey | 2001/0018611 A1 | 8/2001 | Solem et al. |
| 6,436,088 B2 | 8/2002 | Frazier et al. | 2001/0021874 A1 | 9/2001 | Carpentier et al. |
| 6,439,237 B1 | 8/2002 | Buckberg et al. | 2001/0029314 A1 | 10/2001 | Alferness et al. |
| 6,443,949 B2 | 9/2002 | Altman | 2001/0034551 A1 | 10/2001 | Cox |
| 6,450,171 B1 | 9/2002 | Buckberg et al. | 2001/0037123 A1 | 11/2001 | Hancock |
| 6,458,100 B2 | 10/2002 | Roue et al. | 2001/0039434 A1 | 11/2001 | Frazier et al. |
| 6,461,366 B1 | 10/2002 | Seguin | 2001/0039435 A1 | 11/2001 | Roue et al. |
| 6,478,729 B1 | 11/2002 | Rogers et al. | 2001/0039436 A1 | 11/2001 | Frazier et al. |
| 6,494,825 B1 | 12/2002 | Talpade | 2001/0041914 A1 | 11/2001 | Frazier et al. |
| 6,508,756 B1 | 1/2003 | Kung et al. | 2001/0041915 A1 | 11/2001 | Roue et al. |
| 6,511,426 B1 | 1/2003 | Hossack et al. | 2001/0049492 A1 | 12/2001 | Frazier et al. |
| 6,514,194 B2 | 2/2003 | Schweich, Jr. et al. | 2002/0007216 A1 | 1/2002 | Melvin |
| 6,520,904 B1 | 2/2003 | Melvin | 2002/0013571 A1 | 1/2002 | Goldfarb et al. |
| 6,537,203 B1 | 3/2003 | Alferness et al. | 2002/0022880 A1 | 2/2002 | Melvin |
| 6,544,167 B2 | 4/2003 | Buckberg et al. | 2002/0026092 A1 | 2/2002 | Buckberg et al. |
| 6,544,180 B1 | 4/2003 | Doten et al. | 2002/0029783 A1 | 3/2002 | Stevens et al. |
| 6,547,821 B1 | 4/2003 | Taylor et al. | 2002/0056461 A1 | 5/2002 | Jayaraman |
| 6,572,529 B2 | 6/2003 | Wilk | 2002/0058855 A1 | 5/2002 | Schweich, Jr. et al. |
| 6,582,355 B2 | 6/2003 | Alferness et al. | 2002/0065449 A1 | 5/2002 | Wardle |
| 6,587,734 B2 | 7/2003 | Okuzumi | 2002/0077532 A1 | 6/2002 | Gannoe et al. |
| 6,589,160 B2 | 7/2003 | Schweich, Jr. et al. | 2002/0111533 A1 | 8/2002 | Melvin |
| 6,592,619 B2 | 7/2003 | Melvin | 2002/0133055 A1 | 9/2002 | Haindl |
| 6,626,821 B1 | 9/2003 | Kung et al. | 2002/0143250 A1 | 10/2002 | Panescu et al. |
| 6,626,930 B1 | 9/2003 | Allen et al. | 2002/0161275 A1 | 10/2002 | Schweich, Jr. et al. |
| 6,629,534 B1 | 10/2003 | St. Goar et al. | 2002/0169359 A1 | 11/2002 | McCarthy et al. |
| 6,629,921 B1 | 10/2003 | Schweich, Jr. et al. | 2002/0173694 A1 | 11/2002 | Mortier et al. |
| 6,645,139 B2 | 11/2003 | Haindl | 2003/0009081 A1 | 1/2003 | Rogers et al. |
| 6,651,671 B1 | 11/2003 | Donlon et al. | 2003/0028077 A1 | 2/2003 | Alferness et al. |
| 6,673,009 B1 | 1/2004 | Vanden Hoek et al. | 2003/0032979 A1 | 2/2003 | Mortier et al. |
| 6,676,702 B2 | 1/2004 | Mathis | 2003/0045771 A1 | 3/2003 | Schweich, Jr. et al. |
| 6,681,773 B2 | 1/2004 | Murphy et al. | 2003/0105519 A1 | 6/2003 | Fasol et al. |
| 6,682,474 B2 | 1/2004 | Lau et al. | 2003/0166992 A1 | 9/2003 | Schweich, Jr. et al. |
| 6,682,475 B2 | 1/2004 | Cox et al. | 2003/0171641 A1 | 9/2003 | Schweich, Jr. et al. |
| 6,682,476 B2 | 1/2004 | Alferness et al. | 2003/0191538 A1 | 10/2003 | Buckberg et al. |
| 6,685,627 B2 | 2/2004 | Jayaraman | 2004/0002719 A1 | 1/2004 | Oz et al. |
| 6,685,646 B2 | 2/2004 | Cespedes et al. | 2004/0003819 A1 | 1/2004 | St. Goar et al. |
| 6,689,048 B2 | 2/2004 | Vanden Hoek et al. | 2004/0010305 A1 | 1/2004 | Alferness et al. |
| 6,695,768 B1 | 2/2004 | Levine et al. | 2004/0015039 A1 | 1/2004 | Melvin |
| 6,695,866 B1 | 2/2004 | Kuehn et al. | 2004/0015040 A1 | 1/2004 | Melvin |
| 6,701,929 B2 | 3/2004 | Hussein | 2004/0015041 A1 | 1/2004 | Melvin |
| 6,702,732 B1 | 3/2004 | Lau et al. | 2004/0019377 A1 | 1/2004 | Taylor et al. |
| 6,702,763 B2 | 3/2004 | Murphy et al. | 2004/0019378 A1 | 1/2004 | Hlavka et al. |
| 6,702,826 B2 | 3/2004 | Liddicoat et al. | 2004/0024286 A1 | 2/2004 | Melvin |

| | | |
|---|---|---|
| 2004/0030382 A1 | 2/2004 | St. Goar et al. |
| 2004/0034271 A1 | 2/2004 | Melvin et al. |
| 2004/0039442 A1 | 2/2004 | St. Goar et al. |
| 2004/0039443 A1 | 2/2004 | Solem et al. |
| 2004/0044365 A1 | 3/2004 | Bachman |
| 2004/0049115 A1 | 3/2004 | Murphy et al. |
| 2004/0049116 A1 | 3/2004 | Murphy et al. |
| 2004/0059180 A1 | 3/2004 | Melvin |
| 2004/0059181 A1 | 3/2004 | Alferness |
| 2004/0059182 A1 | 3/2004 | Alferness |
| 2004/0059187 A1 | 3/2004 | Alferness |
| 2004/0059188 A1 | 3/2004 | Alferness |
| 2004/0059189 A1 | 3/2004 | Alferness |
| 2004/0059351 A1 | 3/2004 | Eigler et al. |
| 2004/0064014 A1 | 4/2004 | Melvin et al. |
| 2004/0073302 A1 | 4/2004 | Rourke et al. |
| 2004/0092962 A1 | 5/2004 | Thornton et al. |
| 2004/0093023 A1 | 5/2004 | Allen et al. |
| 2004/0098116 A1 | 5/2004 | Callas et al. |
| 2004/0102678 A1 | 5/2004 | Haindl |
| 2004/0102679 A1 | 5/2004 | Alferness et al. |
| 2004/0102839 A1 | 5/2004 | Cohn et al. |
| 2004/0102840 A1 | 5/2004 | Solem et al. |
| 2004/0111095 A1 | 6/2004 | Gordon et al. |
| 2004/0111101 A1 | 6/2004 | Chin |
| 2004/0122448 A1 | 6/2004 | Levine |
| 2004/0122512 A1 | 6/2004 | Navia et al. |
| 2004/0122513 A1 | 6/2004 | Navia et al. |
| 2004/0127980 A1 | 7/2004 | Kowalsky et al. |
| 2004/0127981 A1 | 7/2004 | Rahdert et al. |
| 2004/0127982 A1 | 7/2004 | Machold et al. |
| 2004/0133062 A1 | 7/2004 | Pai et al. |
| 2004/0133069 A1 | 7/2004 | Shapland et al. |
| 2004/0133220 A1 | 7/2004 | Lashinski et al. |
| 2004/0133240 A1 | 7/2004 | Adams et al. |
| 2004/0133273 A1 | 7/2004 | Cox |
| 2004/0138526 A1 | 7/2004 | Guenst |
| 2004/0138744 A1 | 7/2004 | Lashinski et al. |
| 2004/0143323 A1 | 7/2004 | Chawla |
| 2004/0148019 A1 | 7/2004 | Vidlund et al. |
| 2004/0148020 A1 | 7/2004 | Vidlund et al. |
| 2004/0152947 A1 | 8/2004 | Schroeder et al. |
| 2004/0158123 A1 | 8/2004 | Reuter |
| 2004/0158321 A1 | 8/2004 | Reuter et al. |
| 2004/0162610 A1 | 8/2004 | Liska et al. |
| 2004/0167374 A1 | 8/2004 | Schweich et al. |
| 2004/0167539 A1 | 8/2004 | Kuehn et al. |
| 2004/0171907 A1 | 9/2004 | Alferness et al. |
| 2004/0171908 A1 | 9/2004 | Alferness et al. |
| 2004/0171909 A1 | 9/2004 | Alferness |
| 2004/0172046 A1 | 9/2004 | Hlavka et al. |
| 2004/0176678 A1 | 9/2004 | Murphy et al. |
| 2004/0176679 A1 | 9/2004 | Murphy et al. |
| 2004/0176840 A1 | 9/2004 | Langberg et al. |
| 2004/0181121 A1 | 9/2004 | Alferness et al. |
| 2004/0181122 A1 | 9/2004 | Alferness et al. |
| 2004/0181123 A1 | 9/2004 | Alferness et al. |
| 2004/0181124 A1 | 9/2004 | Alferness |
| 2004/0181125 A1 | 9/2004 | Alferness et al. |
| 2004/0181126 A1 | 9/2004 | Buckberg et al. |
| 2004/0181238 A1 | 9/2004 | Zarbatany et al. |
| 2004/0186342 A1 | 9/2004 | Vanden Hock et al. |
| 2004/0186566 A1 | 9/2004 | Hindrichs et al. |
| 2004/0193191 A1 | 9/2004 | Starksen et al. |
| 2004/0193260 A1 | 9/2004 | Alferness et al. |
| 2004/0199183 A1 | 10/2004 | Oz et al. |
| 2004/0225300 A1 | 11/2004 | Goldfarb et al. |
| 2004/0243229 A1 | 12/2004 | Vidlund et al. |
| 2005/0015723 A1 | 1/2005 | Light et al. |
| 2005/0021056 A1 | 1/2005 | St. Goar et al. |
| 2005/0021057 A1 | 1/2005 | St. Goar et al. |
| 2005/0033446 A1 | 2/2005 | Deem et al. |
| 2005/0043792 A1 | 2/2005 | Solem et al. |
| 2005/0049679 A1 | 3/2005 | Taylor et al. |

FOREIGN PATENT DOCUMENTS

| | | |
|---|---|---|
| DE | 298 24 017 U1 | 6/1998 |
| DE | 198 26 675 A1 | 3/1999 |
| DE | 199 47 885 | 4/2000 |
| DE | 199 47 885 A1 | 4/2000 |
| EP | 0 583 012 | 2/1994 |
| EP | 0 583 012 A1 | 2/1994 |
| EP | 0 792 621 A1 | 9/1997 |
| EP | 0 820 729 A1 | 1/1998 |
| FR | 2 768 324 | 3/1999 |
| WO | 91/19465 | 12/1991 |
| WO | 95/06447 | 3/1995 |
| WO | 95/16476 | 6/1995 |
| WO | WO 95/16407 | 6/1995 |
| WO | 96/04852 | 2/1996 |
| WO | WO 96/02197 A1 | 2/1996 |
| WO | 96/40356 | 12/1996 |
| WO | WO 97/14286 | 4/1997 |
| WO | 97/24082 | 7/1997 |
| WO | 97/24101 | 7/1997 |
| WO | WO 97/24083 | 7/1997 |
| WO | 98/03213 | 1/1998 |
| WO | 98/14136 | 4/1998 |
| WO | WO 98/17347 | 4/1998 |
| WO | 98/18393 | 5/1998 |
| WO | 98/26738 | 6/1998 |
| WO | 98/29041 | 7/1998 |
| WO | 98/32382 | 7/1998 |
| WO | WO 98/44969 | 10/1998 |
| WO | WO 98/58598 | 12/1998 |
| WO | WO 99/00059 | 1/1999 |
| WO | 99/11201 | 3/1999 |
| WO | 99/13777 | 3/1999 |
| WO | WO 99/16350 | 4/1999 |
| WO | WO 99/22784 | 5/1999 |
| WO | 99/30647 | 6/1999 |
| WO | 99/44534 | 9/1999 |
| WO | 99/44680 | 9/1999 |
| WO | WO 99/44969 | 9/1999 |
| WO | 99/52470 | 10/1999 |
| WO | WO 99/53977 | 10/1999 |
| WO | 99/56655 | 11/1999 |
| WO | WO 99/66969 | 12/1999 |
| WO | 00/02500 | 1/2000 |
| WO | WO 00/03759 | 1/2000 |
| WO | 00/06026 | 2/2000 |
| WO | 00/06028 | 2/2000 |
| WO | 00/13722 | 3/2000 |
| WO | 00/18320 | 4/2000 |
| WO | 00/27304 | 5/2000 |
| WO | 00/28912 | 5/2000 |
| WO | 00/28918 | 5/2000 |
| WO | WO 00/25842 | 5/2000 |
| WO | WO 00/25853 | 5/2000 |
| WO | 00/36995 | 6/2000 |
| WO | 00/42919 | 7/2000 |
| WO | 00/42951 | 7/2000 |
| WO | WO 00/42950 | 7/2000 |
| WO | WO 00/42951 | 7/2000 |
| WO | 00/45735 | 8/2000 |
| WO | 00/61033 | 10/2000 |
| WO | 00/62727 | 10/2000 |
| WO | WO 00/60995 | 10/2000 |
| WO | WO 00/62715 | 10/2000 |
| WO | 01/03608 | 1/2001 |
| WO | 01/03608 A1 | 1/2001 |
| WO | WO 01/00111 | 1/2001 |
| WO | 01/19291 A1 | 3/2001 |
| WO | 01/21070 | 3/2001 |
| WO | 01/21098 | 3/2001 |

| | | |
|---|---|---|
| WO | 01/21098 A1 | 3/2001 |
| WO | 01/21099 | 3/2001 |
| WO | 01/21099 A1 | 3/2001 |
| WO | WO 01/19292 A1 | 3/2001 |
| WO | WO 01/21247 A1 | 3/2001 |
| WO | 01/28432 A1 | 4/2001 |
| WO | WO 01/26557 A1 | 4/2001 |
| WO | 01/50981 | 7/2001 |

OTHER PUBLICATIONS

Harken, D.E., et al., The Journal of Thoracic Surgery, *The Surgical Correction of Mitral Insufficiency*, vol. 28, pp. 604-627, Jul.-Dec. 1954.
Kay, Earle et al., The Journal of Thoracic Surgery, *Surgical Treatment of Mitral Insufficiency, Experimental Observations*, Jan. vol. 29, pp. 618-620, Jan.-Jun. 1955.
Bailey, C.P. et al., Diseases of the Chest, vol. XXII, *Closed Intracardiac Tactile Surgery*, Jul. 1952, No. 1, pp. 1-24.
Bailey, Charles P., M.D., et al., *The Surgical Corrction of Mitral Insufficiency by the Use of Pericardial Grafts*, The Journal of Thoracic Surgery, vol. 28, No. 6, pp. 551-603, Dec. 1954.
Sakakibara, Shigeru, M.D., Tokyo, Japan, Annals of Surgery, *A Surgical Approach to the Correction of Mitral Insufficiency*, vol. 142, pp. 196-203, Jul.-Dec. 1955.
Glenn, William W. L., MD et al., New Haven Connecticut, Annals of Surgery, *The Surgical Treatment of Mitral Insufficiency: The Fate of A vascularized Transchamber Intracardiac Graft*, vol. 141, No. 4, pp. 510-518, Apr. 1955.
Kay, Earle B., M.D. et al., Cleveland, Ohio, Surgery, A Monthly Journal Devoted to the Art and Science of Surgery, *Surgical Treatment of Mitral Insufficiency*, vol. 37, No. 5, pp. 697-620, May 1955.
Harken, D.E., et al., Surgical Forum, *The Surgical Correction of Mitral Insufficiency*, pp. 4-7, Oct. 1953.
Shumacker, Jr., Harris, B., Indiana University Press, *The Evolution of Cardiac Surgery*, Attempts to Control Mitral Regurgitation, pp. 203-210, 1992.
Timek, Tomasz A., MD, et al, The Journal of Thoracic Surgery, Surgery for Acquired Cardiovascular Disease, *Septal-lateral annular cinching abolishes acute ischemic mitral regurgitation*, vol. 123, No. 5, pp. 881-888, May 2002.
Press Release dated Oct. 3, 1994, "Heartmate System Becomes First Implantable Cardiac-Assist To Be Approved For Commercial Sale in the U.S.," 2 pages, ICI Thermo Cardiosystems Inc.
Correspondence, The Annals of Thoracic Surgery, vol. 46, No. 3, Sep. 1988.
Timek, Thomasz A. et al, Department of Cardiothoracic Surgery and Division of Cardiovascular Medicine, Stanford University School of Medicine, Stanford, CA, *Septal-Lateral Annular Cinching ('SLAC') reduces Mitral Annular Size without Perturbing Normal Annular Dynamics*, 2002.
Hung, Judy MD et al., *Reverse Ventricular Remodeling Reduces Ischemic Mitral Regurgitation: Echo-Guided Device Application in the Beating Heart*, Circulation, www.circulationaha.org, Nov. 12, 2002.
Dullum, Mercedes K.C., *Update on Restraint Devices for Congestive Heart Failure*, Abstract and copy of presentation slides given at Tech-Con 2005 for Society of Thoracic Surgeons, Jan. 23, 2005, 11 pages.
Alonso-Lej, The Journal of Thoracic and Cardiovascular Surgery, vol. 68, No. 3, Sep. 1974, p. 349.
Edie, M.D. et al., "Surgical repair of single ventricle," *The Journal of Thoracic and Cardiovascular Surgery*, vol. 66, No. 3, Sep. 1973, pp. 350-360.
McGoon, M.D. et al., "Correction of the univentricular heart having two atrioventricular valves," *The Journal of Thoracic and Cardiovascular Surgery*, vol. 74, No. 2, Aug. 1977, pp. 218-226.
Lev, M.D., et al., "Single (Primitive) Ventricle," *Circulation*, vol. 39, May 1969, pp. 577-591.
Westaby with Bosher, "Landmarks in Cardiac Surgery," 1997, pp. 198-199.

Shumacker, "Cardiac Aneurysms," *The Evolution of Cardiac Surgery*, 1992, pp. 159-165.
Feldt, M.D., "Current status of the septation procedure for univentricular heart," *The Journal of Thoracic and Cardiovascular Surgery*, vol. 82, No. 1, Jul. 1981, pp. 93-97.
Doty, M.D., "Septation of the univentricular heart," *The Journal of Thoracic and Cardiovascular Surgery*, vol. 78, No. 3, Sep. 1979, pp. 423-430.
Carpentier et al., "Myocardial Substitution with a Stimulated Skeletal Muscle: First Successful Clinical Case," Letter to the Editor, p. 1267, Sep. 25, 1996.
Ianuzzo et al., "Preservation of the Latissimus Dorsi Muscle During Cardiomyoplasty Surgery," *J. Card. Surg.*, 1996:11:99-108.
Ianuzzo et al., "On Preconditioning of Skeletal Muscle: Application to Dynamic Cardiomyoplasty," Invited Commentary, *J. Card. Surg.*, 1996:11:109-110.
Chachques et al., "Latissimus Dorsi Dynamic Cardiomyoplasty," *Ann. Thorac. Surg.*, 1989:47:600-604.
Moreira et al., "Latissimus Dorsi Cardiomyoplasty in the Treatment of Patients with Dilated Cardiomyopathy," Supplement IV Circulation, Sep. 25, 1996.
Lucas et al., "Long-Term Follow-Up (12 to 35 Weeks) After Dynamic Cardiomyoplasty," *JACC*, vol. 22, No. 3, Sep. 1993:758-67.
Batista et al., "Partial Left Ventriculectomy to Improve Left Ventricular Function in End-Stage Heart Disease," *J. Card. Surg.*, 1996:11:96-98.
"Congestive Heart Failure in the United States: A New Epidemic" Data Fact Sheet, National Heart, Lung, and Blood Institute, National Institutes of Health, Dec. 9, 1996, pp. 1-6.
Kormos et al., "Experience with Univentricular Support In Mortally Ill Cardiac Transplant Candidates," *Ann. Thorac. Surg.*, 1990:49:261-71.
Wampler et al., "Treatment of Cardiogenic Shock with the Hemopump Left Ventricular Assist Device," *Ann. Thorac. Surg.*, 1991:52:506-13.
McCarthy et al., "Clinical Experience with the Novacor Ventricular Assist System," *J. Thorac. Cardiovasc. Surg.*, 1991:102-578-87.
Burnett et al., "Improved Survival After Hemopump Insertion In Patients Experiencing Postcardiotomy Cardiogenic Shock During Cardiopulmonary Bypass," From the Section of Transplantation, Division of Cardiovascular Surgery, Texas Heart Institute and St. Luke's Episcopal Hospital, Houston, Texas, dated even with or prior to Jan. 2, 1997, pp. 626-628.
Phillips et al., "Hemopump Support for the Failing Heart," From the Department of Cardiovascular Medicine and Surgery, Mercy Hospital Medical Center, Des Moines, Iowa, date even with or prior to Jan. 2, 1997, pp. 629-631.
Deeb et al., "Clinical Experience with the Nimbus Pump," From the University of Michigan Medical Center Section of Thoracic Surgery and Division of Cardiology, Ann Arbor, Michigan, date even with or prior to Jan. 2, 1997, pp. 632-636.
Bearnson et al., "Development of a Prototype Magnetically Suspended Rotor Ventricular Assist Device," *ASAIO Journal*, 1996, pp. 275-280.
Sakakibara et al., "A Muscle Powered Cardiac Assist Device for Right Ventricular Support: Total Assist or Partial Assist?," *Trans. Am.Soc. Artif. Intern. Organs*, vol. XXXVI, 1990, pp. 372-375.
Medtronic, Inc. 1996 Annual Shareholders Report, 79 pages.
ABIOMED, Inc. Annual Report 1996, 32 pages.
Press Release dated Sep. 16, 1996, "ABIOMED Wins $8.5 Million Federal Contract to Qualify its Artificial Heart for Human Trials," 5 pages.
Press Release dated Sep. 26, 1996, ABIOMED's Temporary Artificial Heart System Reaches 200 U.S. Medical Center Milestone, 1 page.
Press Release dated May 17, 1996, "ABIOMED Receives FDA Approval to Expand Indications for Use of Cardiac Assist System," 1 page.
Press Release dated Oct. 3, 1995, "ABIOMED Wins $4.35 Million Contract from the National Heart, Lung and Blood Institutes to Develop Implantable Heart Booster," 1 page.

Press Release dated Sep. 29, 1995, "ABIOMED wins NIH Grant to Develop Calcification-Resistant Plastic Heart Valve," 1 page.

Press Release dated Aug. 25, 1995, "ABIOMED Wins Research Grant from NIH to Develop Suturing Instrument for Abdominal surgery," 1 page.

Press Release dated Aug. 11, 1995, "ABIOMED Receives Grant from NIH to Develop Disposable Bearingless Centrifugal Blood Pump," 1 page.

Press Release dated Jun. 9, 1995, "ABIOMED Receives Grant from National Institutes of Health to Develop a Laser Welding Technique for Tissue Repair," 1 page.

Press Release dated Apr. 27, 1995, "ABIOMED's Temporary Artificial Heart System Reaches 1,000 Patient Milestone; BVS-5000 in More Than 100 U.S. Medical Centers," 1 page.

"Reversible Cardiomyopathy," *Thoratec's Heartbeat*, vol. 10.2, aug. 1996, 4 pages.

Tsai et al., "Surface Modifying Additives for Improved Device-Blood Compatibility," *ASAIO Journal*, 1994, pp. 619-624.

Farrar et al., "A New Skeletal Muscle Linear-Pull Energy Convertor as a Power Source for Prosthetic Support Devices," *The Journal of Heart & Lung Transplantation*, vol. 11, No. 5, Sep. 1992, pp. 341-349.

Brochure entitled "Thoratec Ventricular Assist Device System—Because Heart Patients Come In All Sizes," date even with or prior to Jan. 2, 1997, 5 pages.

Press Release dated Oct. 3, 1994, "Heartmate System Becomes First Implantable Cardiac-Assist Device to be Approved for Commercial Safe in the U.S.," 2 pages.

Bocchi et al., "Clinical Outcome after Surgical Remodeling of left Ventricle in Candidates to Heart Transplantation with Idiopathic Dilated Cardiomyopathy—Short Term Results," date even with or prior to Jan. 2, 1997, 1 page.

Bach et al., "Early Improvement in Congestive Heart Failure after Correction of Secondary Mitral Regurgitation in End-Stage Cardiomyopathy," *American Heart Journal*, Jun. 1995, pp. 1165-1170.

Schuler et al., "Temporal Response of Left Ventricular Performance to Mitral Valve Surgery," vol. 59, No. 6, Jun. 1979, pp. 1218-1231.

Huikuri, "Effect of Mitral Valve Replacement on Left Ventricular Function in Mitral Regurgitation," *Br. Heart J.*, vol. 49, 1983, pp. 328-333.

Pitarys II et al., "Long-Term Effects of Excision of the Mitral Apparatus on Global and Regional Ventricular Function in Humans," *JACC*, vol. 15, No. 3, Mar. 1, 1990, pp. 557-563.

Bolling et al., "Surgery for Acquired Heart Disease/Early Outcome of Mitral Valve Reconstruction in Patients with End-Stage Cardiomyopathy," *The Journal of Thoracic and Cardiovascular Surgery*, vol. 109, No. 4, Apr. 1995, pp. 676-683.

Masahiro et al., "Surgery for Acquired Heart Disease/Effects of Preserving Mitral Apparatus on Ventricular Systolic Function in Mitral Valve Operations in Dogs," *The Journal of Thoracic and Cardiovascular Surgery*, vol. 106, No. 6, Dec. 1993, pp. 1138-1146.

Dickstein et al., "Heart Reduction Surgery: An Analysis of the Impact on Cardiac Function," *The Journal of Thoracic and Cardiovascular Surgery*, vol. 113, No. 6, Jun. 1997, 9 pages.

McCarthy et al., "Early Results with Partial Left Ventriculectomy," From the Departments of Thoracic and Cardiovascular Surgery, Cardiology, and Transplant Center, Cleveland Clinic Foundation, Presented at the 77th Annual Meeting of the American Association of Thoracic Surgeons, May 1997, 33 pages.

Alonso-Lej, M.D., "Adjustable Annuloplasty for Tricuspid Insufficiency," *The Annals of Thoracic Surgery*, vol. 46, No. 3, Sep. 1988, 2 pages.

Kurlansky et al., "Adjustable Annuloplasty for Tricuspid Insufficiency," *Ann. Thorac. Surg.*, 44:404-406, Oct. 1987.

Savage, M.D., "Repair of left ventricular aneurysm," *The Journal of Thoracic and Cardiovascular Surgery*, vol. 103, No. 3, Sep. 1992, pp. 752-762.

Melvin, "Ventricular Radius Reduction Without Restriction: A Computational Analysis," *ASAIO Journal*, 45:160-165, 1999.

Cox, "Left Ventricular Aneurysms: Pathophysiologic Observations and Standard Resection," *Seminars in Thoracic and Cardiovascular Surgery*, vol. 9, No. 2, Apr. 1997, pp. 113-122.

Boyd et al., "Tricuspid Annuloplasty," *The Journal of Thoracic Cardiovascular Surgery*, vol. 68, No. 3, Sep. 1974, 8 pages.

"Heart 'jacket' could help stop heart failure progression," *Clinica* 916, Jul. 2000.

McCarthy et al., "Device Based Left Ventricular Shape Change Immediately Reduces left Ventricular Volume and Increases Ejection Fraction in a pacing Induced Cardiomyopathy Model in Dogs: A Pilot Study," *JACC*, Feb. 2000, p. 183.

Acorn Cardiovascular, Inc. Abstracts, Nov. 13, 2000.

Acorn Cardiovascular Summary, undated, 1 page.

"Nation's First 'Heart Jacket' Surgery to Treat Heart Failure Performed at HUP; Novel 'Cardiac Support Device' Comes to America After Promising Results in Europe," Jun. 26, 2000, 3 pages.

Acorn Cardiovascular Company Overview, Jun. 2000, 6 pages.

Acorn Cardiovascular Company Overview, undated, 2 pages.

Acorn Cardiovascular Executive Summary, May 2000, 7 pages.

Acorn Cardiovascular Highlights, Abstracts, Mar. 10, 1999.

Acorn Cardiovascular Highlights, Abstracts, Apr. 19, 1999.

Acorn Cardiovascular Highlights, Abstracts, Oct. 1, 1999.

Acorn Cardiovascular Highlights, Abstracts, Nov. 9, 1999.

Batista, M.D. et al., "Partial Left Ventriculectomy to Treat End-Stage Heart Disease," *The Society of Thoracic Surgeons*, 1997, pp. 634-638.

Melvin, "Ventricular Radius-Reduction Without Resection, A Computational Assessment," 4 pages, undated.

Melvin et al., "Reduction of Ventricular Wall Tensile Stress by Geometric Remodeling Device," 1 page, undated.

Melvin et al., "Reduction of Ventricular Wall Tensile Stress by Geometric Remodeling Device," 1999, 6 pages.

Kay et al., "Surgical Treatment of Mitral Insufficiency", *The Journal of Thoracic Surgery*, 29: 618-620, 1955.

Harken et al., "The Surgical Correction of Mitral Insufficiency", *The Journal of Thoracic Surgery*, 28:604-27, 1954.

Bailey et al., "Closed Intracardiac Tactile Surgery", *Diseases of the Chest*, 22:1-24, Jul. 1952.

Sakakibara, "A Surgical Approach to the Correction of Mitral Insufficiency", *Annals of Surgery*, 142:196-203, Aug. 1955.

Glenn et al., "The Surgical Treatment of Mitral Insufficiency: The Fate of A Vascularized Transchamber Intracardiac Graft", *Annals of Surgery*, 141:510-518, Apr. 1955.

Kay et al., "Surgical Treatment of Mitral Insufficiency", *Surgery*, 37:697-706, May 1955.

Bailey et al. "The Surgical Correction of Mitral Insufficiency By The Use of Pericardial Grafts", *The Journal of Thoracic Surgery*, 28:551-603, Dec. 1954.

Harken et al., "The Surgical Correction of Mitral Insufficiency", *Surgical Forum*, 4:4-7, 1953.

Shumacker, Jr., "Attempts to Control Mitral Regurgitation", *The Evolution of Cardiac Surgery*, 203-210, 1992.

Carpentier et al., "Myocardial Substitution With A Stimulated Skeletal Muscle: First Successful Clinical Case, Dept. of Card Surg and Lab for the Study of Cardiac Grafts and Prostheses," p. 1267, 1996.

Ianuzzo et al., "Preservationof the Latissimus Dorsi Muscle During Cardiomyoplasty Sugery," J. Card Surg, 1996, 11:99-108.

Ianuzzo et al., "On Preconditioning of Skeletal Muscle: Application to Dynamic Cardiomyoplasty," J. Card. Surg., 1996, 11:109-110.

Moreira et al., "Latissimus Dorsi Cardiomyoplasty in the Treatment of Patients With Dilated Cardiomyopathy," Cardiac Transplantation, Ventricular Support, and Cardiac Preservation, 1996, pp. VI 257-263.

Lucas et al., "Long-Term Follow-Up (12 to 35 Weeks) After Dynamic Cardiomyoplasty," JACC, vol. 22 No. 3: 758-67, 1993.

Batista et al., "Partial Left Ventriculectomy to Improve Left Ventricular Function in End-Stage Heart Disease," J. Card. Surg, 1996, 11:96-98.

Data Fact Sheet, "Congestive Heart Failure in the United States: A New Epidemic," 6 pages, 1996, from http://www.nhlbi.nih.gov/nhlbi/cardio/other/gp/CHF.htm.

Chachques et al., "Latissimus Dorsi Dynamic Cardiomyoplasty," Ann. Thorac. Surg. 1989; 47:600-604.

US 6,197,052, 03/2002, Cosgrove et al. (withdrawn)

* cited by examiner

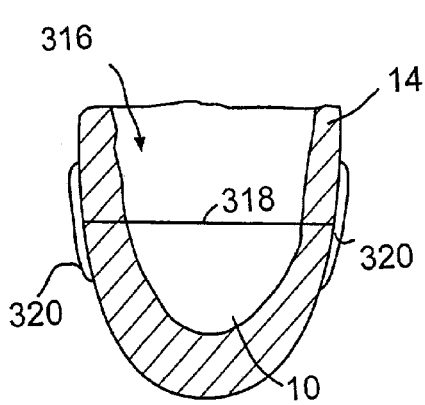
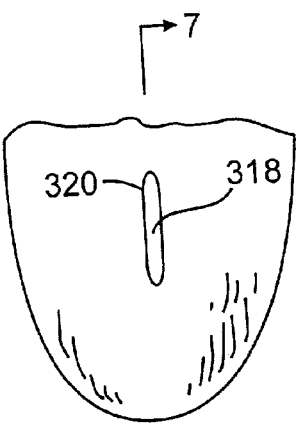
FIG. 7  FIG. 8
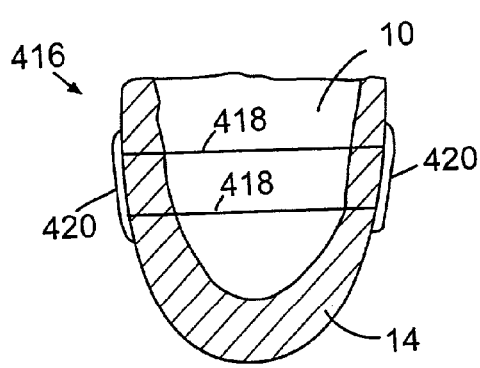
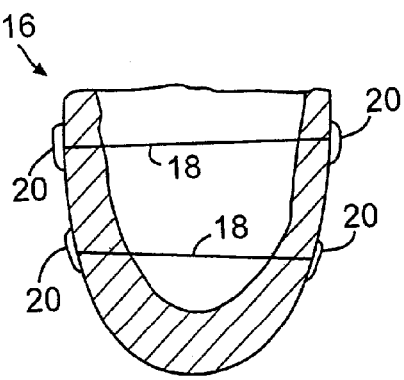
FIG. 9  FIG. 10
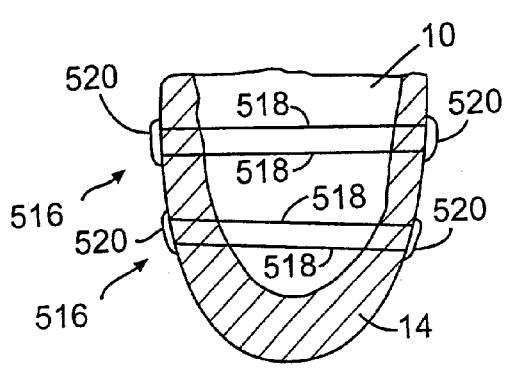
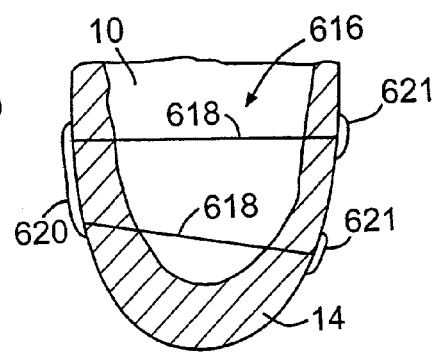
FIG. 11  FIG. 12

METHODS AND DEVICES FOR IMPROVING CARDIAC FUNCTION IN HEARTS

CROSS REFERENCE TO RELATED APPLICATIONS

This application is a continuation of application Ser. No. 09/422,328, filed Oct. 21, 1999, now U.S. Pat. No. 6,406,420, which is a continuation-in-part of application Ser. No. 09/124,286, filed Jul. 29, 1998, now U.S. Pat. No. 6,045,497, which is a continuation-in-part of application Ser. No. 08/933,456, filed Sep. 18, 1997, now U.S. Pat. No. 5,961,440, which is a continuation-in-part of application Ser. No. 08/778,277, filed Jan. 2, 1997, now U.S. Pat. No. 6,050,936, all of which are incorporated herein by reference.

FIELD OF THE INVENTION

The present invention pertains to the field of apparatus for treatment of a failing heart. In particular, the apparatus and its related methods of the present invention is directed toward reducing the wall stress in the failing heart. The present invention further includes methods and devices for improving cardiac function in hearts having discrete zones of infarcted tissue. Such methods and devices reduce the radius of curvature and/or alter the geometry or shape of the infarcted tissue and adjacent regions to thereby reduce wall stress on the heart and improve the heart's pumping performance.

BACKGROUND OF THE INVENTION

The syndrome of heart failure is a common course for the progression of many forms of heart disease. Heart failure may be considered to be the condition in which an abnormality of cardiac function is responsible for the inability of the heart to pump blood at a rate commensurate with the requirements of the metabolizing tissues, or can do so only at an abnormally elevated filling pressure. There are many specific disease processes that can lead to heart failure. Typically these processes result in dilatation of the left ventricular chamber. Etiologies that can lead to this form of failure include idiopathic, valvular, viral, and ischemic cardiomyopathies.

The process of ventricular dilatation is generally the result of chronic volume overload or specific damage to the myocardium. In a normal heart that is exposed to long term increased cardiac output requirements, for example, that of an athlete, there is an adaptive process of slight ventricular dilation and muscle myocyte hypertrophy. In this way, the heart fully compensates for the increased cardiac output requirements. With damage to the myocardium or chronic volume overload, however, there are increased requirements put on the contracting myocardium to such a level that this compensated state is never achieved and the heart continues to dilate.

The basic problem with a large dilated left ventricle is that there is a significant increase in wall tension and/or stress both during diastolic filling and during systolic contraction. In a normal heart, the adaptation of muscle hypertrophy (thickening) and ventricular dilatation maintain a fairly constant wall tension for systolic contraction. However, in a failing heart, the ongoing dilatation is greater than the hypertrophy and the result is a rising wall tension requirement for systolic contraction. This is felt to be an ongoing insult to the muscle myocyte resulting in further muscle damage. The increase in wall stress is also true for diastolic filling. Additionally, because of the lack of cardiac output, there is generally a rise in ventricular filling pressure from several physiologic mechanisms. Moreover, in diastole there is both a diameter increase and a pressure increase over normal, both contributing to higher wall stress levels. The increase in diastolic wall stress is felt to be the primary contributor to ongoing dilatation of the chamber.

Prior treatments for heart failure associated with such dilatation fall into three general categories. The first being pharmacological, for example, diuretics and ACE inhibitors. The second being assist systems, for example, pumps. Finally, surgical treatments have been experimented with, which are described in more detail below.

With respect to pharmacological treatments, diuretics have been used to reduce the workload of the heart by reducing blood volume and preload. Clinically, preload is defined in several ways including left ventricular end diastolic pressure (LVEDP), or indirectly by left ventricular end diastolic volume (LVEDV). Physiologically, the preferred definition is the length of stretch of the sarcomere at end diastole. Diuretics reduce extra cellular fluid which builds in congestive heart failure patients increasing preload conditions. Nitrates, arteriolar vasodilators, angiotensin converting enzyme (ACE) inhibitors have been used to treat heart failure through the reduction of cardiac workload by reducing afterload. Afterload may be defined as the tension or stress required in the wall of the ventricle during ejection. Inotropes function to increase cardiac output by increasing the force and speed of cardiac muscle contraction. These drug therapies offer some beneficial effects but do not stop the progression of the disease.

Assist devices include mechanical pumps. Mechanical pumps reduce the load on the heart by performing all or part of the pumping function normally done by the heart. Currently, mechanical pumps are used to sustain the patient while a donor heart for transplantation becomes available for the patient.

There are at least four surgical procedures for treatment of heart failure associated with dilatation: 1) heart transplantation; 2) dynamic cardiomyoplasty; 3) the Batista partial left ventriculectomy; and 4) the Jatene and Dor procedures for ischemic cardiomyopathy, discussed in more detail below. Heart transplantation has serious limitations including restricted availability of organs and adverse effects of immunosuppressive therapies required following heart transplantation. Cardiomyoplasty involves wrapping the heart with skeletal muscle and electrically stimulating the muscle to contract synchronously with the heart in order to help the pumping function of the heart. The Batista partial left ventriculectomy surgically remodels the left ventricle by removing a segment of the muscular wall. This procedure reduces the diameter of the dilated heart, which in turn reduces the loading of the heart. However, this extremely invasive procedure reduces muscle mass of the heart.

One form of heart failure, ischemic cardiomyopathy, results from the formation of one or more zones of ischemia, or infarction, of the myocardium. Infarction occurs when blood supply to the heart tissue has been obstructed resulting in a region of tissue that loses its ability to contract (referred to as infarcted tissue). The presence of infarcted tissue may lead to three conditions in the heart causing cardiac malfunction. These conditions are ventricular aneurysms (ventricular dyskinesia), non-aneurysmal ischemic or infarcted myocardium (ventricular akinesia), and mitral regurgitation.

Ventricular aneurysms typically result from a transmural myocardial infarction, frequently due to the occlusion of the left anterior descending artery (LAD). This results in a transmural infarcted region of the apical portion of the left ventricle and anterior septal. A ventricular aneurysm is formed when the infarction weakens the heart wall to such an extent that the tissue stretches and thins, causing the left ventricular wall to expand during systole (dyskinesia). FIG. 55 illustrates a ventricular aneurysm A occurring in the apical region of left ventricle LV. As shown by the shaded region in FIG. 55, aneurysm A includes infarcted tissue 24 that results in a reduced wall thickness when compared to adjacent non-infarcted wall regions, as shown by the unshaded regions in FIG. 55. FIG. 55 also shows the septal wall S partially infarcted, again shown by the shaded region. The ventricular aneurysm also may be dyskinetic, meaning that when the ventricle contracts, the aneurysm further dilates, or bulges, outward. The infarcted region of the septal wall S also may be particularly dyskinetic, especially in the case of the infarcted tissue having progressed to an aneurysm.

The bulge resulting from an aneurysm can have several serious effects on the heart and its performance that can lead to in both morbidity and mortality. For example, because the bulge creates a geometric abnormality as well as a region of non-contracting tissue, thrombosis is more likely to occur in that region. Thrombosis is the formation of a blood clot, or thrombus, that can cause other medical complications, such as a stroke. An ischemic stroke is a blockage of blood flow to the brain that occurs when the thrombus breaks free and is ejected out of the ventricle.

Another serious effect this bulging can have is the denigration of the heart's pumping function. The aneurysmal bulge creates problems with pumping function in at least three ways. First, the infarcted tissue does not contribute to the pumping of the ventricle because it does not contract (akinesia). To account for this loss of pumping, remaining portions of the ventricle wall may contract more to maintain cardiac output. If the infarcted region thins and progresses to an aneurysm (dyskinesia), this effect is further exacerbated by the aneurysm expanding with a portion of the blood from the ventricular contraction. This further increases the contractile requirement of the remaining functional myocardium.

Second, the aneurysmal bulge alters the geometry of the entire ventricular chamber. Thus the ventricle develops a larger radius of curvature, which directly applies more tension to the heart wall, as characterized by LaPlace's law.

Third, over time, the above two conditions lead the functional muscle of the ventricle to work harder than normal. This can lead to continued dilatation of the ventricle, increasing tension in the walls of the heart, with increased myocardial oxygen requirement and further progressing heart failure.

Non-aneurysmal ischemic or infarcted myocardium (akinesia) occurs when a major coronary artery is occluded and results in infarction in the myocardial tissue, but without a bulging aneurysm. In a manner similar to an aneurysm, the akinetic ischemic or infarcted zone ceases to participate in the ventricular contraction. This results in the functioning, contractile myocardium needing to contract more to make up for the lack of contraction of the akinetic zone. Typically, the result is the entire ventricle increasing in size, which increases wall stress. Again, since the functioning myocardium must work harder, continuing progression of heart failure can occur.

Mitral regurgitation also may result from infarcted tissue, depending on the region of the ventricle that has become infarcted or aneurysmal and any subsequent overall ventricular dilation. Mitral regurgitation is a condition whereby blood leaks through the mitral valve due to an improper positioning of the valve structures that causes it not to close entirely. If the infarcted or aneurysmal region is located in the vicinity of the mitral valve, geometric abnormalities may cause the mitral valve to alter its normal position and dimension, and may lead to annular dilatation and the development of mitral regurgitation.

Typical treatments of infarcted tissue, and ventricular aneurysms in particular, include a variety of open surgical procedures. In the case of a ventricular aneurysm, traditionally, a "linear" aneurysmectomy is performed. This procedure involves the removal of aneurysmal portions of the anterior wall along with any thrombus that may exist. FIG. 41 illustrates the result of a conventional surgical method when an aneurysm occurs in the distal left ventricle. According to this method, the region of aneurysmal scar tissue that extends through the entire thickness of the chamber wall (transmural infarction) is removed by incision and the remaining border zone regions 24' (i.e., regions where infarcted tissue meets non-infarcted muscle) are sewn together with a suture 27. In a linear aneurysm repair procedure, the ventricular septal wall S that is infarcted is left untouched. Additionally, the septal wall generally remains untouched because simple excision and suturing does not involve excluding or cutting the septal wall. Usually, only those wall portions having infarcted tissue through their thickness (transmural infarcted) are removed while the portions having infarcted tissue only on an inner wall (endocardial infarcted) are left in place. The term border zone refers to this region of endocardial infarction. This surgical procedure results in some infarcted tissue regions remaining in the heart chamber, particularly any infarcted tissue in the septal wall. The effects of the remaining non-contractile tissue stresses the remaining contractile tissue because this contractile tissue must "make up" for the non-contracting and often dyskinetic tissue. Over time, these effects can continue to lead to progression of heart failure.

These procedures have to be performed with the patient on cardiopulmonary bypass. The heart also may be stopped in order to perform the surgery. Any thrombus inside the ventricle is removed. Clinical results of this traditional surgical procedure have been mixed with respect to improvement in cardiac function.

Newer surgical approaches include the "Dor" and "Jatene" procedures. In the "Dor" procedure, the aneurysm is removed and an endocardial patch is placed to cover the dyskinetic septal wall portion of the aneurysm. In this manner, at least the portion of stroke volume "lost" to dyskinesia is restored. In the "Jatene" technique, a purse string suture is placed at the base of the aneurysm. The infarcted septal wall is circumferentially reduced by inbrication with sutures. The result is that most of the aneurysmal tissue is excluded from the ventricle. These procedures address the infarcted septal wall, generally left untouched in the traditional linear aneurysmectomy, by either exclusion or by the use of a surgical patch. These newer techniques are also used in cases of non-aneurysmal infarctions (akinesia). In these cases, the exclusion or elimination of the infarcted region reduces the size and therefore the radius of the chamber, thereby lowering wall stress.

These various described techniques for treating infarcted and aneurysmal tissue regions in the heart wall suffer from limitations and drawbacks. For instance, many of the surgical techniques involve invasive incisions in the heart wall which can be traumatic and risky to patients. Also, while these procedures attempt to improve cardiac function by removal of the aneurysm or infarcted tissue, they only minimally reduce the wall stress of the remaining contractile ventricle. Furthermore, patients typically undergo cardiopulmonary bypass and/or their heart is stopped during many of these surgeries.

SUMMARY OF THE INVENTION

The advantages and purpose of the invention will be set forth in part in the description which follows, and in part will be obvious from the description, or may be learned by practice of the invention. The advantages and purpose of the invention will be realized and attained by means of the elements and combinations particularly pointed out in the appended claims.

Due to the drawbacks and limitations of the previous techniques for treating dilated, infarcted, and aneurysmal tissue in hearts, there exists a need for alternative methods and devices that are less invasive, pose less risk to the patient, and are likely to prove more clinically effective. The present invention provides improvements in these areas over the existing techniques.

One aspect of the present invention pertains to a non-pharmacological, passive apparatus and method for the treatment of a failing heart due to dilatation. The device is configured to reduce the tension in the heart wall. It is believed to reverse, stop or slow the disease process of a failing heart as it reduces the energy consumption of the failing heart, decreases isovolumetric contraction, increases isotonic contraction (sarcomere shortening), which in turn increases stroke volume. The device reduces wall tension during diastole and systole.

These apparatus of the present invention which reduce heart wall stress by changing chamber wall geometry can be referred to as "splints". Splints can be grouped as either "full cycle splints," which engage the heart to produce a chamber shape change throughout the cardiac cycle, or "restrictive splints," which do not engage the heart wall at end systole to produce a chamber shape change.

In one embodiment, the apparatus includes a tension member for drawing at least two walls of the heart chamber toward each other to reduce the radius or area of the heart chamber in at least one cross sectional plane. The tension member has anchoring members disposed at opposite ends for engagement with the heart or chamber wall.

In another embodiment, the apparatus includes a compression member for drawing at least two walls of a heart chamber toward each other. In one embodiment, the compression member includes a balloon. In another embodiment of the apparatus, a frame is provided for supporting the compression member.

Yet another embodiment of the invention includes a clamp having two ends biased toward one another for drawing at least two walls of a heart chamber toward each other. The clamp includes at least two ends having atraumatic anchoring members disposed thereon for engagement with the heart or chamber wall.

In yet another embodiment, a heart wall tension reduction apparatus is provided which includes a first tension member having two oppositely disposed ends and first and second elongate anchor members. A second tension member can be provided. One of the elongate anchors may be substituted for by two smaller anchors.

In an alternate embodiment of the heart wall tension reduction apparatus, an elongate compression member can be provided. First and second elongate lever members preferably extend from opposite ends of the compression member. A tension member extends between the first and second lever members.

The compression member of the above embodiment can be disposed exterior to, or internally of the heart. The tension member extends through the chamber or chambers to bias the lever members toward the heart.

In yet another embodiment of a heart wall tension reduction apparatus in accordance with the present invention, a rigid elongate frame member is provided. The frame member can extend through one or more chambers of the heart. One or more cantilever members can be disposed at opposite ends of the frame member. Each cantilever member includes at least one atraumatic pad disposed thereon. The atraumatic pads disposed at opposite ends of the frame member can be biased toward each other to compress the heart chamber.

One method of placing a heart wall tension apparatus or splint on a human heart includes the step of extending a hollow needle through at least one chamber of the heart such that each end of the needle is external to the chamber. A flexible leader is connected to a first end of a tension member. A second end of the tension member is connected to an atraumatic pad. The leader is advanced through the needle from one end of the needle to the other. The leader is further advanced until the second end of the tension member is proximate the heart and the first end of the tension member is external to the heart. A second atraumatic pad is connected to the first end of the tension member such that the first and second atraumatic pads engage the heart.

Yet another method of placing a heart wall tension apparatus on a heart includes the step of extending a needle having a flexible tension member releasably connected thereto through at least one chamber of the heart such that opposite ends of the tension member are external to the chamber and exposed on opposite sides of the chamber. The needle is removed from the tension member. Then first and second atraumatic pads are connected to the tension member at opposite ends of the tension member.

In the treatment of heart failure due to infarcted tissue, possibly including an aneurysm as well, another aspect of the invention involves placing the splint relative to the infarcted or aneurysmal zone, and, in a preferred embodiment, diametrically across the infarcted or aneurysmal zone, to decrease the stress on the infarcted tissue and adjacent border zone tissue. An alternative to diametric placement of the splint includes placing one atraumatic anchor member of the splint at the center of the infarcted or aneurysmal region, extending the splint across the entire heart chamber, and placing the second atraumatic anchor member on the opposite chamber wall. In the case of infarcted or aneurysmal tissue in the vicinity of the mitral valve, an aspect of the present invention includes a method of placing the splint adjacent but below the mitral valve to draw the papillary muscles together or the walls of the valve seat together. It is also envisioned to use the splint both as the sole device for treating infarcted tissue and aneurysms or in combination with the surgical techniques described earlier.

An external splint, using a compression member, also may be used to treat a heart having infarcted or aneurysmal tissue. The compression member is placed entirely exterior to the heart and positioned so as to result in similar effects as discussed above with reference to the splint.

Other inventive methods and devices to treat infarcted tissue and aneurysms include a variety of patching and suturing methods and related devices. Each of these methods and related devices reduces the radius of curvature of the infarcted wall region and adjacent regions and contains the infarcted region to stop further progression.

A further aspect of the invention involves the identification of aneurysmal and infarcted regions using any one or more of a variety of devices and methods. These devices and methods, which will be described more specifically herein, include a bipolar electrode, liquid dye injection and tracing, fiber optics, MRI, and ultrasound. These devices can be used to distinguish between healthy and infarcted heart tissue.

In accordance with the purposes of the invention as embodied and broadly described herein, methods and related devices for treating a heart having infarcted tissue in one of its chambers are disclosed. In a preferred embodiment of the invention, a method for treating a heart having a zone of infarcted tissue in its chamber includes deforming a wall of the chamber that-includes the infarcted tissue such that a radius of curvature of the wall is reduced.

In another preferred embodiment of the present invention, the method involves providing at least one tension member having two ends and an anchor on each end. The tension member is positioned transverse to the chamber to reduce the radius of curvature of the wall of the chamber that includes the infarcted tissue and/or to draw the walls containing the infarcted tissue together.

In another preferred embodiment, the present invention involves positioning a tension member having anchors on each of its ends transverse to the heart chamber so that the infarcted tissue is drawn toward an interior of the heart chamber. The anchors are placed exterior to the chamber.

In yet another preferred embodiment, the present invention includes positioning a compression member having a first end and a second end, each having anchor members around an exterior of the heart. The compression member is positioned so as to surround the chamber with infarcted tissue and to reduce the radius of curvature of the portion of the heart wall that has the infarcted tissue.

In accordance with another preferred embodiment, a method of treating a heart having infarcted tissue in one of its chambers involves epicardial suturing around the perimeter of a region of infarcted tissue and pulling free ends of the suture to draw the infarcted tissue region together. The suture is then secured to hold the infarcted tissue together. This suture also may be employed in combination with a myocardial patch or a substantially rigid enclosure member, both of which represent other preferred embodiments of the present invention.

In accordance with another preferred embodiment of the present invention, a method of treating a heart having infarcted tissue in one of its chambers involves positioning an enclosure member around a zone of infarcted tissue. During the positioning, the enclosure member has a first configuration. After positioning, the enclosure member is then secured to a wall of the heart and the enclosure member reconfigures to a second configuration. Upon reconfiguration to the second configuration, the radius of curvature of the portion of the heart wall including the infarcted tissue reduces.

In accordance with yet another preferred embodiment of the present invention, an apparatus for treating a heart having a zone of infarcted tissue in one of its chambers is provided. The apparatus includes an enclosure member adapted to assume a first configuration during placement of the enclosure member around an infarcted tissue zone. The enclosure member further is adapted to assume a second configuration after securing the enclosure member to a heart wall surrounding the chamber. The second configuration draws the infarcted tissue toward a center of the enclosure member and reduces the radius of curvature of the heart wall.

In accordance with another preferred embodiment of the present invention, a device for treating a heart having infarcted tissue in one of its chambers is provided. The device includes a patch adapted to be attached to the heart, with a substantially elongated member secured to the patch. When the patch is placed over the infarcted or aneurysmal tissue region, the elongated member tends to push the infarcted tissue region toward an interior of the heart chamber.

In accordance with yet another preferred embodiment of the present invention, a plurality of sutures are attached at one end to points on a chamber wall proximate to an infarcted tissue region and the sutures are extended up through a space defined by an enclosure member to draw the infarcted tissue together and through the enclosure member. The other ends of the sutures are then attached to points on the wall of the chamber to hold the tissue in place.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and, together with the description, serve to explain the principles of the invention. In the drawings.

FIG. 7 is a vertical cross-sectional view of the left ventricle of a human heart showing an alternate version of the splint in accordance with the present invention;

FIG. 8 is an end of the splint shown in FIG. 7;

FIG. 9 is a vertical cross-sectional view of a chamber of a human heart showing another alternative embodiment of the splint in accordance with the present invention;

FIG. 10 is a vertical cross-section of a chamber of a human heart showing another alternative configuration of splints in accordance with the present invention;

FIG. 11 is a vertical cross-sectional view of a chamber of a human heart showing another embodiment of a splint in accordance with the present invention;

FIG. 12 is a vertical cross-sectional view of a chamber of a human heart showing another embodiment of the splint in accordance with the present invention;

DESCRIPTION OF THE PREFERRED EMBODIMENTS

Figure 1:
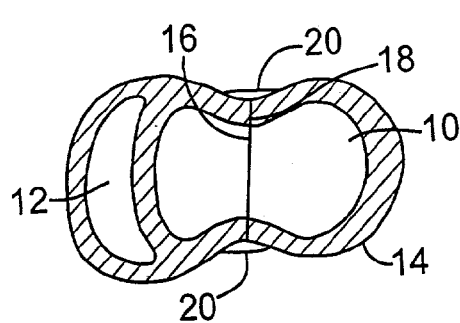
FIG. 1 is a transverse cross-section of the left and right ventricles of a human heart showing the placement of a splint in accordance with the present invention.

The various aspects of the invention to be discussed herein generally pertain to devices and methods for treating heart conditions, including, for example, dilatation and infarction, including infarction causing aneurysms. For the purposes of providing clarity and consistency throughout the remaining description of the invention, the following terms have the general definitions set forth below:

"infarction": or "infarcted": refers to myocardium (also described as tissue or muscle) that has lost its ability to contract as a result of cellular necrosis, this term can include, for example, aneurysmal tissue and scar tissue that replaces the necrotic cellular muscle tissue;

"aneurysm" or "aneurysmal": refers to infarcted myocardium that is dyskinetic with respect to surrounding portions of the myocardium;

"contractile": refers to myocardium that is not infarcted and has generally retained contractile potential, though this muscle tissue may not be fully contracting given other conditions, e.g. too much wall stress; and "border zone": refers to chamber wall that has a region of infarcted tissue and a region of contractile tissue through its thickness.

These definitions are generally consistent with the accepted definitions recognized by those skilled in the art.

The devices of the present invention operate passively in that, once placed in the heart, they do not require an active stimulus either mechanical, electrical, or otherwise, to function. The devices alter the shape or geometry of the heart, both locally and globally, and increase the heart's efficiency by their placement with respect to the heart. That is, the heart experiences an increased pumping efficiency through an alteration in its shape or geometry and concomitant reduction in stress on the heart walls.

The inventive devices and methods offer numerous advantages over the existing treatments for various heart conditions. The devices are relatively easy to manufacture and use, and the related surgical techniques for their implementation do not require the invasive procedures of current surgical techniques. For instance, the surgical technique does not necessarily require removing portions of the heart tissue, opening the heart chamber, or stopping the heart. For these reasons, the surgical techniques of the present invention are also less risky to the patient than other techniques.

The devices and methods of the present invention used to treat infarcted tissue and aneurysms also are likely to be more effective than prior devices. As will be described, the inventive devices alter the shape or geometry of the chamber, either globally or locally, and reduce the radius of curvature of the chamber wall, resulting in lower stresses in the heart wall. Moreover, with many of the inventive devices there is no need to open the heart chamber to deploy the device, even when the device is deployed on the septal wall. These methods and devices also could be used in conjunction with coronary artery bypass grafting (CABG). In CABG surgery, the use of the inventive methods and related devices allow for quickly reducing stress on the myocardium, which may save "stunned" tissue, i.e., tissue that is being starved of nutrients carried with the blood flow, that otherwise may not be recoverable after a certain time period. Also, the inventive methods and device may hinder further progression or dilation of scarred, non-contractile tissue.

The disclosed inventive methods and related devices involve geometric reshaping of the heart. In certain aspects of the inventive methods and related devices, substantially the entire chamber geometry is altered to return the heart to a more normal configuration. FIGS. 36 through 40, which will be described in further detail later, show a model of this geometric reshaping, which includes a reduction in radius of curvature of the chamber walls. Prior to reshaping the chamber geometry, the heart walls experience high stress due to a combination of both the relatively large increased diameter of the chamber and the thinning of the chamber wall. Geometric reshaping according to the present invention reduces the stress in the walls of the heart chamber to increase the heart's pumping efficiency, as well as to stop further dilatation of the heart.

Other aspects of the inventive methods and devices involve geometric reshaping a particular area of the chamber and/or reducing the radius of curvature of the chamber wall in that area. When portions of the heart wall form a bulge due to an aneurysm, the radius of much of the heart chamber changes. This increases stress on the heart walls. Additionally, the healthy regions of the heart work harder to pump in order to make up pumping volume due to lost contractility in the infarcted tissue region. Together, these effects limit the pumping effectiveness of the heart and can contribute to further degradation of the heart. Geometrically reshaping the area of the aneurysm by, for example, reducing the radius of curvature of the wall, lowers stress on the wall regions in that vicinity and improves pumping function. In addition, the geometric reshaping permits the scar tissue to heal in a more organized fashion and reduces progression of the scar tissue into other areas and further aneurysmal bulging.

Although many of the methods and devices are discussed below in connection with their use in the left ventricle of the heart, these methods and devices may be used in other chambers of the heart for similar purposes. One of ordinary skill in the art would understand that the use of the devices and methods described herein would be substantially the same if employed in other chambers of the heart. The left ventricle has been selected for illustrative purposes because a large number of the disorders that the present invention treats occur in the left ventricle.

Reference will now be made in detail to the present preferred embodiments of the invention, examples of which are illustrated in the accompanying drawings.

Wherever possible, the same reference numbers will be used throughout the drawings to refer to the same or like parts.

FIG. 1 shows a transverse cross-section of a left ventricle 10 and a right ventricle 12 of a human heart 14. Extending through the left ventricle is a splint 16 including a tension member 18 and oppositely disposed anchors 20. Splint 16, as shown in FIG. 1, has been positioned to draw opposite walls of left ventricle 10 toward each other to reduce the "radius" of the left ventricular cross-section or the cross-sectional area thereof to reduce left ventricular wall stresses. It should be understood that although the splint 16 and the alternative devices disclosed herein are described in relation to the left ventricle of a human heart, these devices could also be used to reduce the radius or cross-sectional area of the other chambers of a human heart in transverse or vertical directions, or at an angle between the transverse and vertical.

Those apparatus of the present invention which reduce heart wall stress by changing chamber wall geometry can be referred to as "splints". "Full cycle splints" engage the heart to produce a chamber shape change throughout the cardiac cycle. "Restrictive splints" do not engage the heart wall at end systole to 110 produce a chamber shape change.

Figure 2:
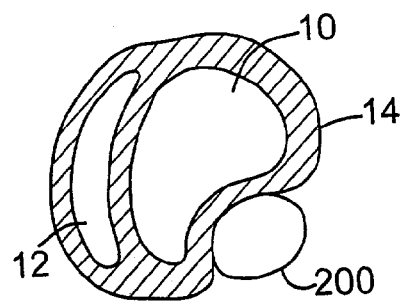
FIG. 2 is a transverse cross-section of the left and right ventricles of a human heart showing the placement of a balloon device in accordance with the present invention.

FIG. 2 discloses an alternate embodiment of the present invention, wherein a balloon 200 is deployed adjacent the left ventricle. The size and degree of inflation of the balloon can be varied to reduce the radius or cross-sectional area of left ventricle 10 of heart 14.

Figure 3:
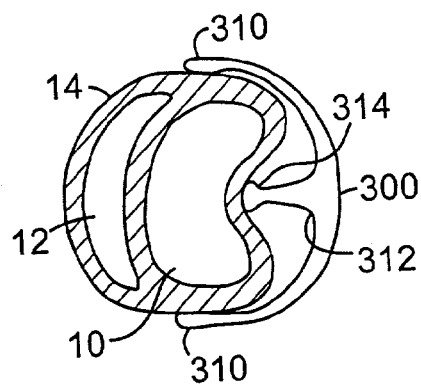
FIG. 3 is a transverse cross-section of the left and right ventricles of a human heart showing the placement of an external compression frame structure in accordance with the present invention.

FIG. 3 shows yet another alternative embodiment of the present invention deployed with respect to left ventricle 10 of human heart 14. Here a compression frame structure 300 is engaged with heart 14 at atraumatic anchor pads 310. A compression member 312 having an atraumatic surface 314 presses against a wall of left ventricle 10 to reduce the radius or cross-sectional area thereof.

Figure 4:
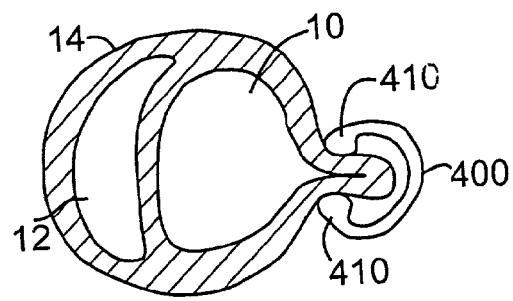
FIG. 4 is a transverse cross-section of the left and right ventricles of a human heart showing a clamp in accordance with the present invention.

FIG. 4 is a transverse cross-sectional view of human heart 14 showing yet another embodiment of the present invention. In this case a clamp 400 having atraumatic anchor pads 410 biased toward each other is shown disposed on a wall of left ventricle 10. Here the radius or cross-sectional area of left ventricle 10 is reduced by clamping off the portion of the wall between pads 410. Pads 410 can be biased toward each other and/or can be held together by a locking device.

Each of the various embodiments of the present invention disclosed in FIGS. 1–4 can be made from materials which can remain implanted in the human body indefinitely. Such biocompatible materials are well-known to those skilled in the art of clinical medical devices.

Figure 5:
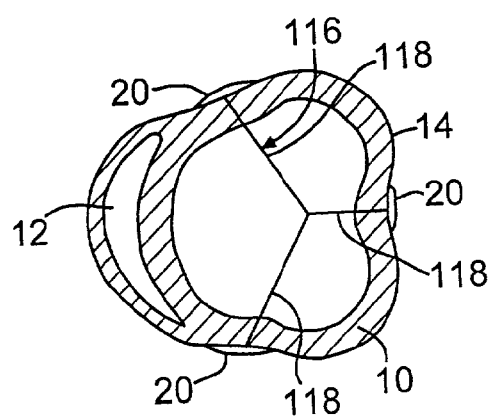
FIG. 5 is a transverse cross-section of the left and right ventricles of a human heart showing a three tension member version of the splint of FIG. 1.
Figure 6:
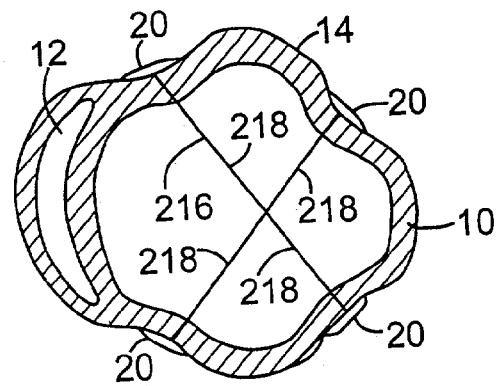
FIG. 6 is a transverse cross-section of the left and right ventricles of a human heart showing a two tension member version of the splint shown in FIG. 1.

FIG. 5 shows an alternate embodiment of the splint of FIG. 1 referred to in FIG. 5 by the numeral 116. The embodiment 116 shown in FIG. 5 includes three tension members 118 as opposed to a single tension member 18 as shown in FIG. 1. FIG. 6 shows yet another embodiment of the splint 216 having four tension members 218. It is anticipated that in some patients, the disease process of the failing heart may be so advanced that three, four or more tension members may be desirable to reduce the heart wall stresses more substantially than possible with a single tension member as shown in FIG. 1.

FIG. 7 is a partial vertical cross-section of human heart 14 showing left ventricle 10. In FIG. 7, another splint embodiment 316 is shown having a tension member 318 extending through left ventricle 10. On opposite ends of tension member 318 are disposed elongate anchors or pads 320. FIG. 8 is an end view of tension member 318 showing elongate anchor 320.

FIG. 9 shows another embodiment of a splint 416 disposed in a partial vertical cross-section of human heart 14. Splint 416 includes two elongate anchors or pads 420 similar to those shown in FIGS. 7 and 8. In FIG. 9, however, two tension members 418 extend through left ventricle 10 to interconnect anchors 420 on opposite sides of heart 14.

FIG. 10 is a vertical cross section of heart 14 showing left ventricle 10. In this case, two splints 16 are disposed through left ventricle 10 and vertically spaced from each other to resemble the configuration of FIG. 9.

FIG. 11 is a vertical cross-sectional view of the left ventricle of heart 14. Two alternate embodiment splints 516 are shown extending through left ventricle 10. Each splint 516 includes two tension members 518 interconnecting two anchors or pads 520.

FIG. 12 is yet another vertical cross-sectional view of left ventricle 10 of heart 14. An alternate embodiment 616 of the splint is shown extending through left ventricle 10; Splint 616 includes an elongate anchor pad 620 and two shorter anchors or pads 621. Splint 616 includes two tension members 618. Each tension member 618 extends between anchors 620 and respective anchors 621.

Figure 13:
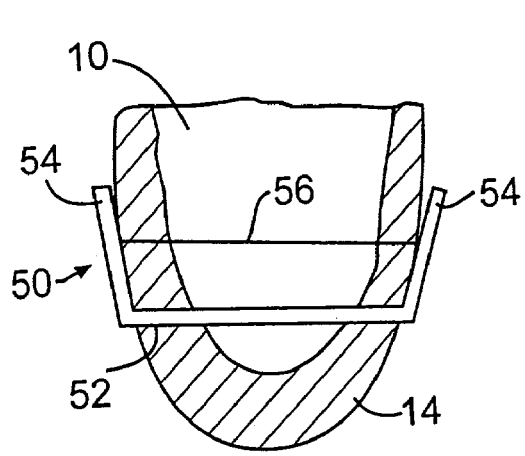
FIG. 13 is a vertical cross-sectional view of a chamber of a human heart showing a compression member version of the splint in accordance with the present invention.

FIG. 13 is a vertical cross-sectional view of left ventricle 10 of heart 14. A splint 50 is shown disposed on heart 14. Splint 50 includes a compression member 52 shown extending through left ventricle 10. Opposite ends of compression member 52 are disposed exterior to left ventricle 10. Lever members 54 extend from each end of compression member 52 upwardly along the exterior surface of ventricle 10. A tension member 56 extends between lever members 54 to bias lever members 54 toward heart 14 to compress chamber 10. Compression member 52 should be substantially rigid, but lever members 54 and to some degree compression member 52 should be flexible enough to allow tension member 56 to bias lever members 54 toward heart 14. Alternately, lever members 54 could be hinged to compression member 52 such that lever members 54 could pivot about the hinge when biased toward heart 14 by tension member 56.

Figure 14:
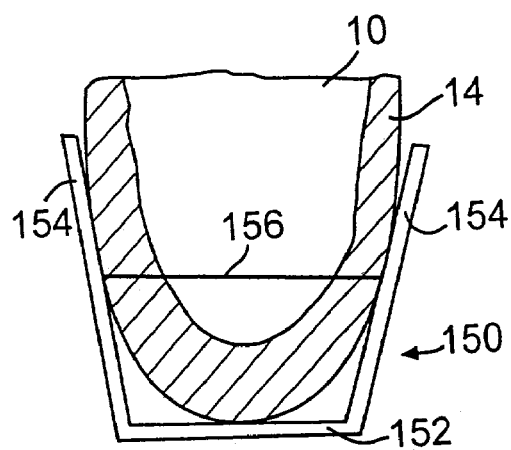
FIG. 14 is a vertical cross-sectional view of a chamber of a human heart showing another version of the splint shown in FIG. 13.

FIG. 14 shows an alternate embodiment 156 of the splint shown in FIG. 13. In this case lever members 154 are longer than members 54 as compression member 152 of splint 150 has been disposed to the exterior of left ventricle 10.

Figure 15:
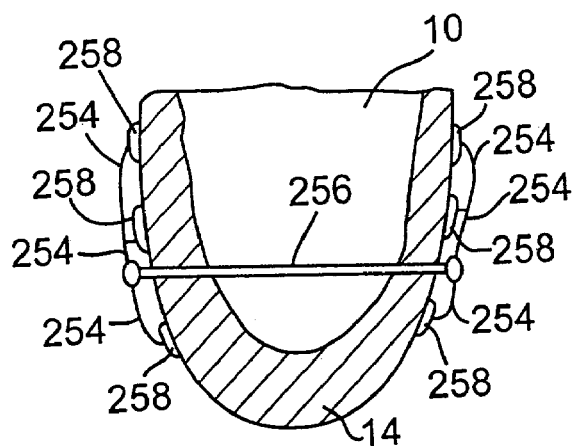
FIG. 15 is a vertical cross-sectional view of a chamber of a human heart showing a frame member version of the splint in accordance with the present invention.
Figure 16:
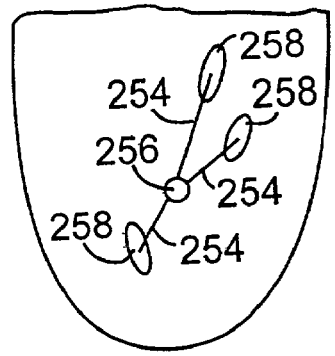
FIG. 16 is an end view of the splint of FIG. 15.

FIG. 15 is a vertical cross-sectional view of left ventricle 10 of heart 14. An alternate embodiment 250 of the splint is shown on heart 14. A preferably relatively rigid frame member 256 extends through ventricle 10. Disposed on opposite ends of frame 256 are cantilever member 254. Disposed on cantilever members 254 are atraumatic pads 258. Cantilever members 254 can be positioned along frame member 256 such that atraumatic pads 258 press against heart 14 to compress chamber 10. FIG. 16 is an end view of frame member 256 showing cantilever members 254 and pads 258.

It should be understood that each of the embodiments described above should be formed from suitable biocompatible materials known to those skilled in the art. The tension members can be formed from flexible or relatively more rigid material. The compression members and frame member should be formed from generally rigid material which may flex under load, but generally hold its shape.

Figure 17:
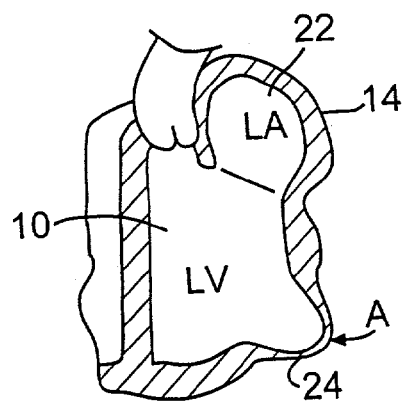
FIG. 17 is a vertical cross-section of the left ventricle and atrium, the left ventricle having aneurysmal scar tissue.

As will be described in more detail herein, FIG. 17 is a partial vertical cross-section of human heart 14 showing left ventricle 10 and left atrium 22. As shown in FIG. 17, heart 14 includes a region of scar tissue 24 associated with an aneurysm or ischemia. As shown in FIG. 17, the scar tissue 24 increases the radius or cross-sectional area of left ventricle 10 in the region affected by the scar tissue. Such an increase in the radius or cross-sectional area of the left ventricle will result in greater wall stresses on the walls of the left ventricle.

Figure 18:
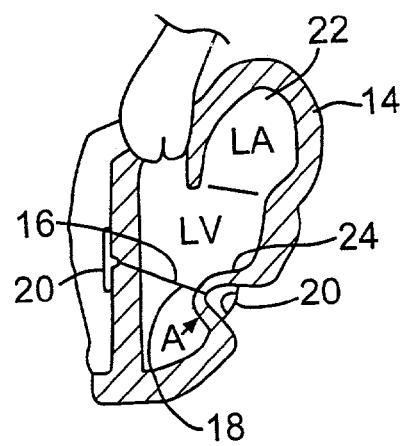
FIG. 18 is a vertical cross-section of the heart of FIG. 17 showing the splint of FIG. 1 drawing the aneurysmal scar tissue toward the opposite wall of the left ventricle.

FIG. 18 is a vertical cross-sectional view of the heart 14 as shown in FIG. 17, wherein a splint 16 has been placed to draw the scar tissue 24 toward an opposite wall of left ventricle 10. As a consequence of placing splint 16, the radius or cross-sectional area of the left ventricle affected by the scar tissue 24 is reduced. The reduction of this radius or cross-sectional area results in reduction in the wall stress in the left ventricular wall and thus improves heart pumping efficiency.

Figure 19:
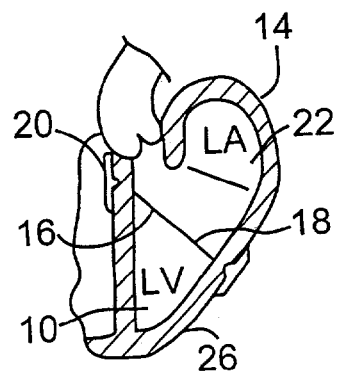
FIG. 19 is a vertical cross-section of the left ventricle and atrium of a human heart showing a version of the splint of FIG. 1 having an elongate anchor bar.

FIG. 19 is a vertical cross-sectional view of left ventricle 10 and left atrium 22 of heart 14 in which a splint 16 has been placed. As shown in FIG. 19, splint 16 includes an alternative anchor 26. The anchor 20 is preferably an elongate member having a length as shown in FIG. 19 substantially greater than its width (not shown). Anchor bar 26 might be used to reduce the radius or cross-sectional area of the left ventricle in an instance where there is generalized enlargement of left ventricle 10 such as in idiopathic dilated cardiomyopathy. In such an instance, bar anchor 26 can distribute forces more widely than anchor 20.

Figure 20:
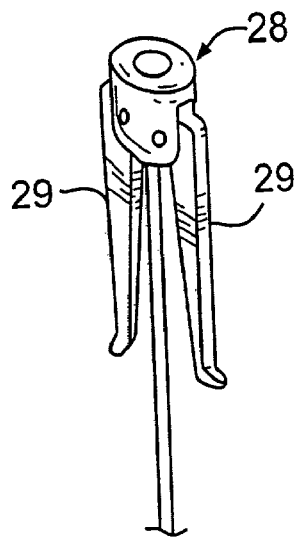
FIG. 20 is a side view of an undeployed hinged anchor member.
Figure 21:
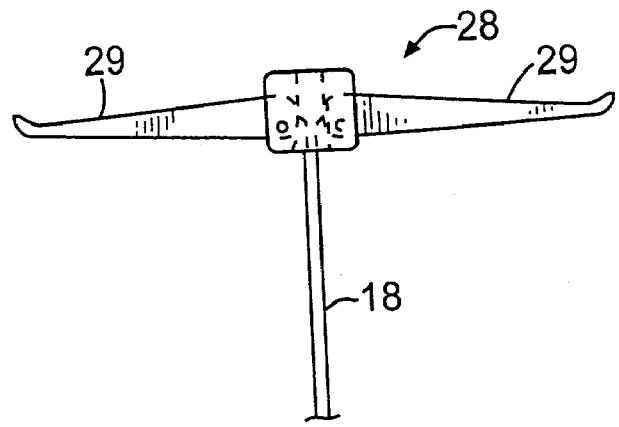
FIG. 21 is a side view of a deployed hinged anchor member of FIG. 10.

FIGS. 20 and 21 are side views of a hinged anchor 28 which could be substituted for anchors 20 in undeployed and deployed positions respectively. Anchor 28 as shown in FIG. 20 includes two legs similar to bar anchor 26. Hinged anchor 28 could include additional legs and the length of those legs could be varied to distribute the force over the surface of the heart wall. In addition there could be webbing between each of the legs to give anchor 28 an umbrella-like appearance.

Preferably the webbing would be disposed on the surface of the legs which would be in contact with the heart wall.

Figure 22:
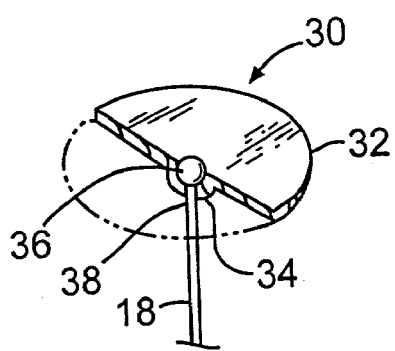
FIG. 22 is a cross-sectional view of an captured ball anchor member.

FIG. 22 is a cross-sectional view of a capture ball anchor 30. Capture ball anchor 30 can be used in place of anchor 20. Capture ball anchor 30 includes a disk portion 32 to distribute the force of the anchor on the heart wall, and a recess 34 for receiving a ball 36 affixed to an end of tension member 18. Disk 32 and recess 34 include a side groove which allows tension member 38 to be passed from an outside edge of disk 32 into recess 34. Ball 36 can then be advanced into recess 34 by drawing tension member 18 through an opening 38 in recess 34 opposite disk 32.

Figure 23:
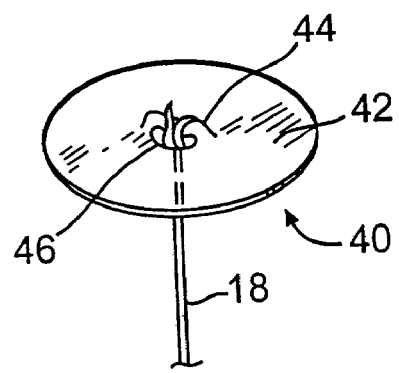
FIG. 23 is a perspective view of a cross bar anchor member.

FIG. 23 is a perspective view of a cross bar anchor 40. The cross bar anchor 40 can be used in place of anchors 20. The anchor 40 preferably includes a disk or pad portion 42 having a cross bar 44 extending over an opening 46 in pad 42. Tension member 18 can be extended through opening 46 and tied to cross bar 42 as shown.

Figure 24:
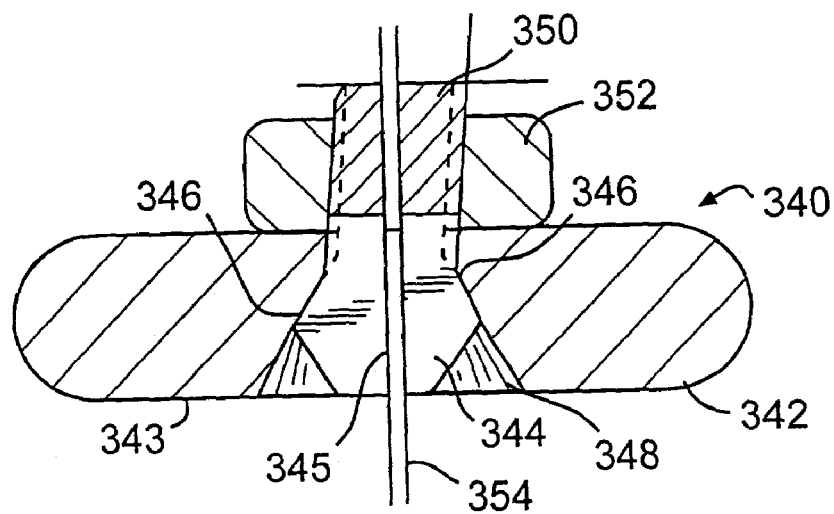
FIG. 24 is a cross sectional view of an alternate anchor pad.

FIG. 24 is a cross sectional view of an alternate embodiment of anchor pad 340 in accordance with the present invention. Anchor pad 340 preferably includes a disc shaped pad portion 342. Disc-shaped pad portion 342 includes side 343, which in use is disposed toward the heart. A conical aperture 348 having sloping sides 346 extends through pad 342. Collet 344 is disposed within orifice 348. A threaded portion 350 of collet 344 extends from orifice 348 opposite side 343, nut 352 is threaded over threaded portion 350. Lumen 345 extends through collet 344. A tension member 354 is shown extending through lumen 345. Lumen 345 has a diameter such that when nut 352 is not tightened on threaded portion 350, tension member 354 can slide freely through lumen 345. When nut 352 is tightened, it draws collet 344 away from side 343. Collet 344 is then pinched between walls 346 of orifice 348. When collet 344 is pinched, the size of lumen 345 is reduced such that tension member 354 can no longer move freely within lumen 345, fixing the position of pad 340 on tension member 354.

Figure 25:
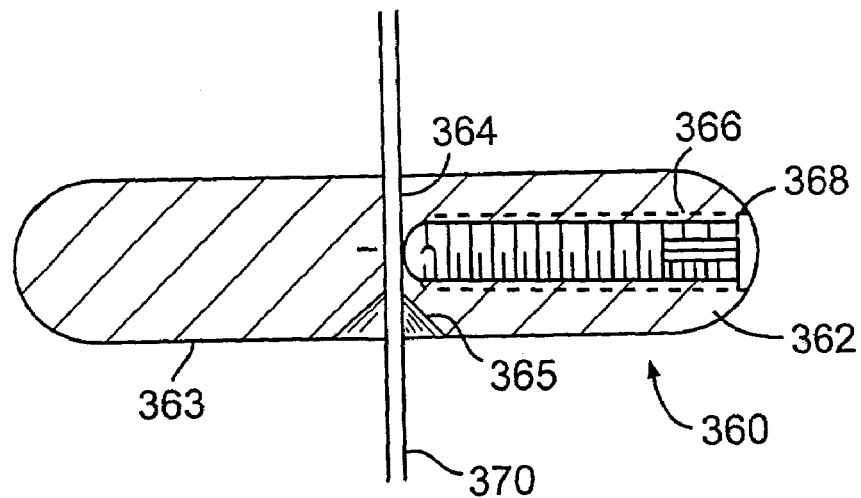
FIG. 25 is a cross sectional view of an alternate anchor pad.

FIG. 25 is a cross sectional view of an alternate embodiment of an anchor pad 360 in accordance with the present invention. Anchor pad 360 includes a generally disc-shaped pad portion 362. Pad 362 includes a side 363 which when the pad is in use, is disposed toward the heart. A tension member lumen 364 extends through pad 362. Lumen 364 preferably has a generally conical shaped portion 365 disposed toward side 363. Tension member 370 is shown disposed through lumen 364 in FIG. 25. Pad 362 includes a threaded passage 366 extending from an edge of pad 362 to lumen 364. A set screw 368 is threaded into passage 366. Set screw 368 can be tightened to engage tension member 370 to fix the position of anchor pad 360. When set screw 368 is not tightened, the size of lumen 364 is preferably large enough that anchor pad 360 can slide relatively freely over tension member 370.

Figure 26:
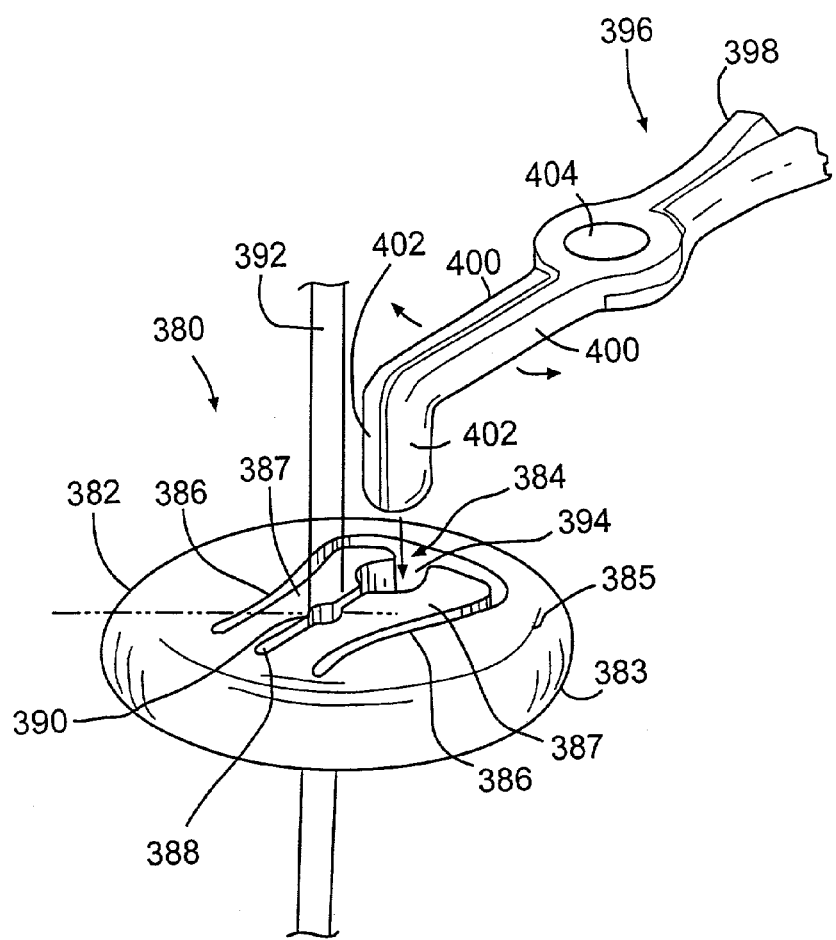
FIG. 26 is a perspective view of yet another alternate embodiment of an anchor pad including an anchor pad loosening device.

FIG. 26 is a perspective view of yet another embodiment of anchor pad 380 in accordance with the present invention. Anchor pad 380 preferably includes a generally disc-shaped pad portion 382 having a first side 383 which in use would be disposed toward the heart and a second side 385. Pad 382 as well as pads 342 and 362 are preferably formed from a metal such as stainless steel alloys or titanium alloys.

A tension member fastener 384 is formed in pad 382 by cutting a series of grooves and apertures through pad 382 from side 385 to side 383. A first groove 386 has a generally horseshoe shape. Second groove 388 extends between opposite portions of horseshoe shaped groove 386 to form two oppositely disposed cantilever members 387. A relatively large aperture 394 is formed between cantilever members 387 proximate their free ends. A second and smaller aperture 390 is formed closer to the fixed ends of cantilever members 387. Tension member 392 is shown extending through aperture 390.

As shown in FIG. 26, tension member 392 is clamped between cantilever members 387 such that the location of pad 382 is fixed along tension member 392. Pad 382 can be released by using a spreading device 396 to spread cantilever members 387 apart. Spreading device 396 includes handle 398 to spreading arms 400 each having a finger 402. Fingers 402 can be placed within aperture 394 then aims 400 and fingers 402 can be spread apart by pivoting them around a pin 404 such that cantilevers 387 are spread apart and pad 382 can move freely along tension member 392. It can be appreciated that although spreader 396 is shown extending transversely from tension member 392, it could also be configured such that fingers 402 do not curve transversely from arms 400 and thus spreader 396 could be disposed parallel to tension member 392. This would be particularly desirable in a situation where anchor pad 380 was being placed through a port or window during a less invasive splint implantation procedure. It can be appreciated that cantilever members 387 can be held apart such that pad 380 can be moved along tension member 392 by placement of a temporary wedge or pin in groove 388. For example, grooves 388 may include an additional small aperture disposed between aperture 390 and aperture 394 into which a pin could be placed to hold open members 387. When it is desired to fix the position of anchor pad 380 on tension member 392, device 396 could be used to spread cantilever members 387 to remove the pin. The cantilever members could then be released to engage tension member 392. Aperture 390 of pad 380 can also include a conical portion disposed toward side 383 such as conical portion 365 of pad 360.

Cantilever arms 384 are preferably configured such that they do not stress tension member 392 beyond its elastic limit. It can also be appreciated that the force developed by cantilever members 387 impinging on tension member 392 is operator independent and defined by the geometry and material characteristics of members 387.

Figure 27:
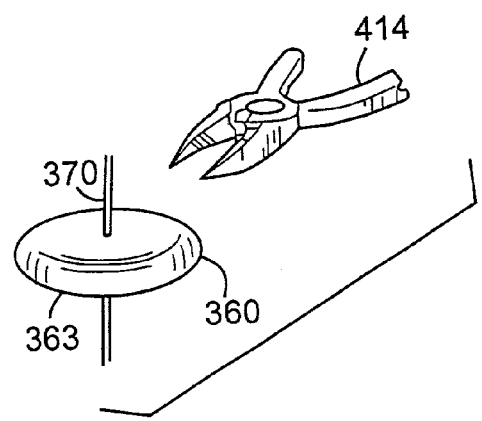
FIG. 27 is a perspective view of a tension member clip.

FIG. 27 is a perspective view of an anchor pad 360 having a tension member 370 extending therethrough. After pad 360 is secured to tension member 370, that portion of tension member 370 which extends from the side of anchor pad 360 opposite side 363 is preferably removed. This can be accomplished by trimming tension member 370 with wire cutter 414 or scissors. Although anchor pad 360 is used here to illustrate trimming tension member 370, it can be appreciated that in each of the embodiments disclosed herein there may be an excess portion of tension member extending from an anchor, which is preferably removed or trimmed.

Figure 28:
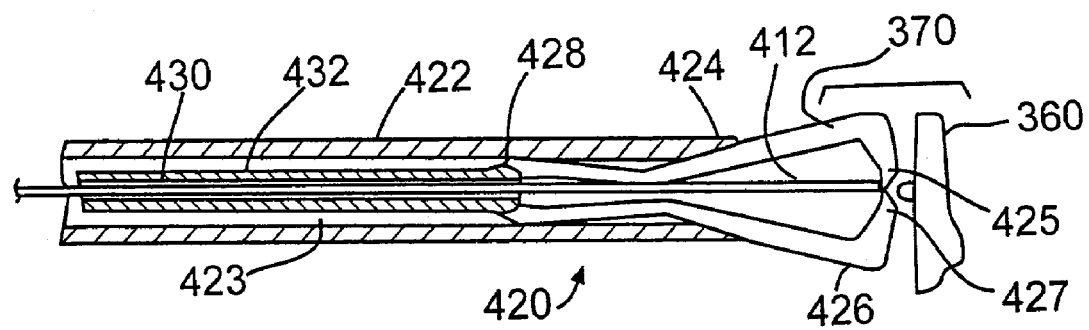
FIG. 28 is a cross sectional view of an alternate embodiment of a tension member clip.

FIG. 28 is a cross sectional view of an alternate embodiment 420 of a tension member cutter. Device 420 includes an elongate outer tube 422 having a distal end 424. Tube 424 defines a lumen 423 through which extends a second tube 430 having a distal end 428. Extending distally from distal end 428 are two cutting arms 424 and 426 which are shown partially withdrawn into lumen 423 and transversely restrained by distal end 424 of outer tube 422. When unrestrained by distal end 424, arms 424 and 426 are biased apart. Each arm 424 and 426 has a cutting element 425 and 427, respectively. Elements 425 and 427 are shown in contact with each other in FIG. 28. A tension member 370 extends between arms 424 and through lumen 432 of inner tube 430. A representative anchor pad 360 is disposed adjacent elements 425 and 427. Device 420 of FIG. 28 is particularly useful when trimming excess tension member using less invasive techniques as it can be readily advanced over a tension member through a port or window trocar.

Figure 29:
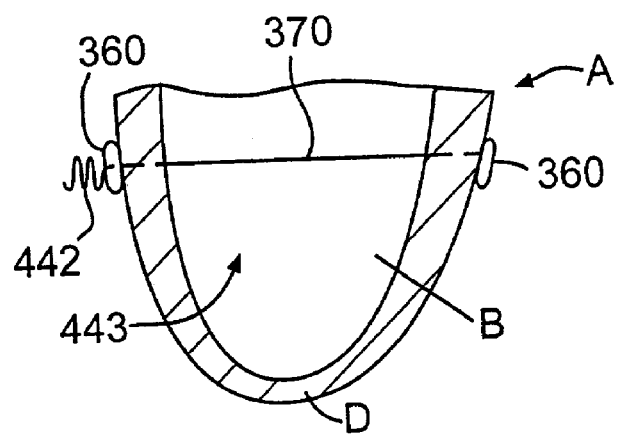
FIG. 29 is a cross sectional view of a heart including a tension member having a heat set end.

FIG. 29 is a vertical cross sectional view of left ventricle B of heart A. A transventricular splint 443 including a tension member 370 and anchor pads 360 are shown disposed on heart A. To the left of heart A as shown in the figure is a coiled portion 442 of tension member 470. As an alternative to trimming an excess length of tension member, tension member 370 could be formed from a shape memory alloy such that portion 442 could be preset to assume a coil shape when warmed to near body temperature.

Once the length of the tension member has been adjusted, the anchors are secured in place along the tension member and the excess length of tension member removed if desired, the anchor or anchor pads are preferably secured in place on the heart. The anchor or anchor pads are secured such that relatively movement between the anchors or anchor pads and the heart is limited to reduce abrasion of the heart wall. To secure the anchor or anchor pads to heart A, a biocompatible adhesive could be placed between the pad and the heart to adhere the pad to the heart. Alternately, apertures could be provided in the pad such that sutures could be extended through the apertures and into the heart to secure the pad. In addition to sutures, the pad could include threaded apertures into which anchor screws could be advanced through the pad and- into the heart wall to secure the pad to the heart.

Figure 30:
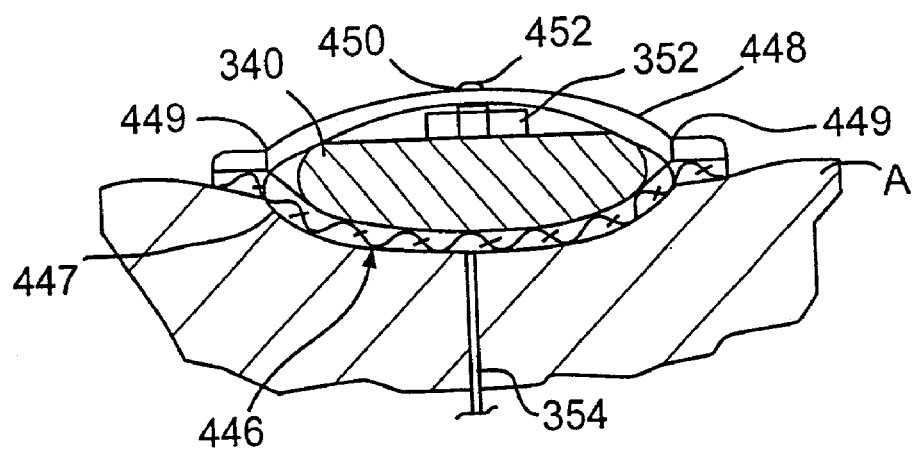
FIG. 30 is a cross sectional view of the pad including an envelope.

FIG. 30 illustrates yet another alternative approach to securing the anchors or anchor pads to the heart surface. FIG. 30 is a cross sectional view of an anchor pad 340 disposed on heart A. Anchor pad 340 is disposed within an envelope 446. Envelope 446 includes a bottom layer 447 disposed between anchor pad 340 and heart A and a top layer 448 disposed on the opposite side of anchor pad 340. Layers 347 and 340 are held together by sutures 449. Bottom layer 447 is preferably a mesh or expanded PTFE which has a pore size or intranodial dimension sufficient to promote tissue ingrowth. The pore size is preferably between about 10 and about 100 microns and more preferably, between about 20 and about 40 microns. With respect to expanded PTFE, the intranodial dimension is preferably between about 10 to about 100 microns and more preferably between about 20 to about 40 microns. The top material could also be expanded PTFE or the like having a pore size which preferably does not promote ingrowth and thus resists adhesion to surrounding tissue. As an alternative embodiment, the pores could be formed directly in the pad surface.

Figure 31:
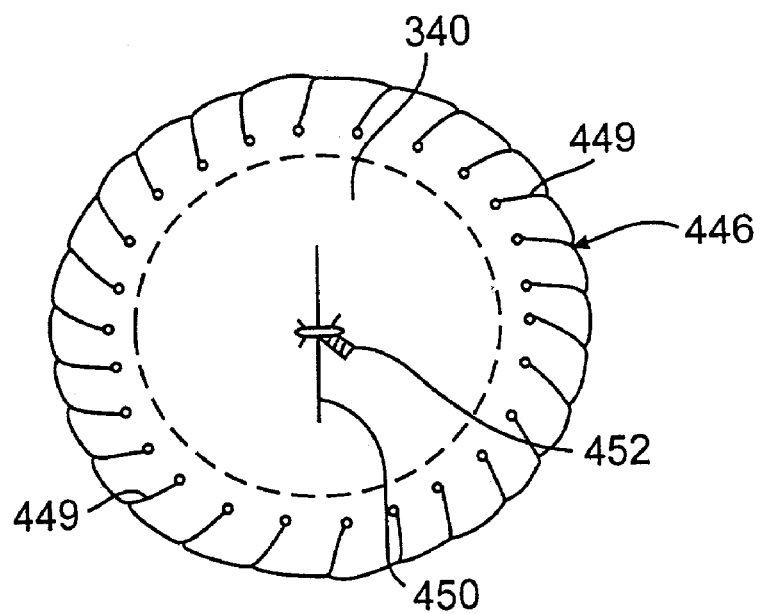
FIG. 31 shows the envelope of FIG. 30.

Envelope 446 would preferably be placed around pad 340 prior to placing pad 340 on tension member 354. A window 450 can be provided to provide access to nut 352 to secure pads to tension member 354. After tightening nut 352, window 450 can be closed by suture 452. FIG. 31 is a top view of pad 340 and envelope 446 of FIG. 30. It can be appreciated that a similar envelope can be placed around the various anchor pads disclosed herein. The location of the window may have to vary, however, to provide access to the respective means for securing the anchor pads to the tension member.

The splints of the present invention can be implanted acutely or chronically. When the splints are implanted chronically, it is particularly important that the tension member or members be highly fatigue resistant. Typical materials for the tension member can include, among other biocompatible materials, stainless steel, titanium alloys, NiTi alloys such as Nitinol or elgiloy. In a preferred embodiment, the tension member is a wire having a diameter of between 0.005 to 0.035 inches in diameter or, more preferably, between 0.01 and 0.02 inches in diameter and, most preferably, about 0.014 inches in diameter. The length of the tension member between the pads is preferably about 0.6 to 4 inches, and more preferably, between about 1 to 3 inches and, most preferably, about 2 inches. To improve the fatigue resistance of the metallic tension members, their surface can be electro-polished, buffed or shot peened. Drawing or annealing of the metal will also improve fatigue resistance.

The tension member, in a preferred embodiment, articulates with respect to the anchor pad to reduce bending of the tension member at the pad. This can be accomplished by a ball and socket joint shown in FIG. 22, for example. The tension member itself can be made more flexible or bendable by providing a multi-filament tension member such as a braided or twisted wire cable tension member. A multifiber filament structure of numerous smaller wires can then easily, while reducing the stress level on any individual wire as compared to a solid wire of the same diameter as the multifilament bundle. Such a multi-filament tension member can be made from biocompatible materials such as, but not limited to, stainless steel, Nitinol, titanium alloys, LCP (liquid crystal polymer), Spectra™ fiber, kevlar fiber, or carbon fiber. In a preferred embodiment, the multi-filament structure is coated or covered to substantially seal the multi-filament structure. Coatings such as silicone, urethane or PTFE are preferred.

Figure 32:
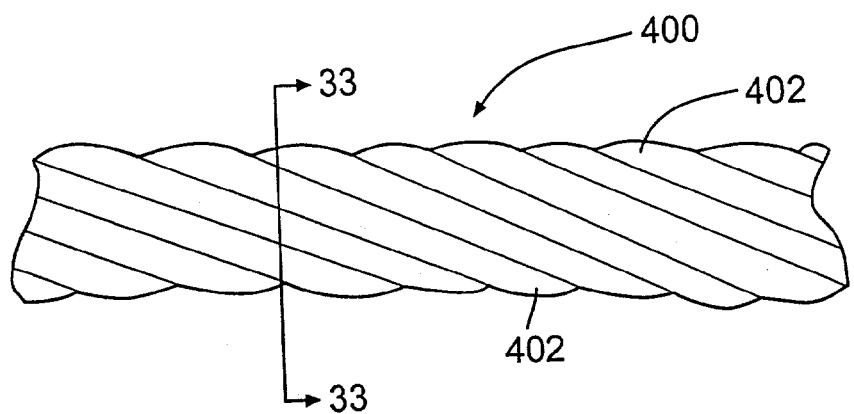
FIG. 32 is a side view of a multifilament twisted cable.
Figure 33:
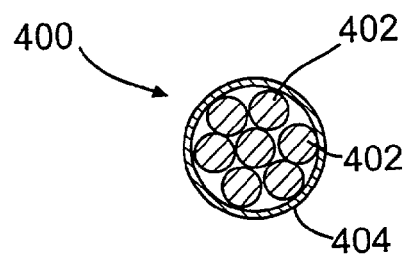
FIG. 33 is a cross sectional of the cable of FIG. 32.

FIG. 32 is a side view of multifilament twisted cable 400. Cable 400 includes a plurality of wires or filaments 402 twisted about the longitudinal axis of cable 400. FIG. 33 is a transverse cross sectional view of cable 400. In FIG. 33, cable 400 includes a surrounding coating 404 not shown in FIG. 32.

Figure 34:
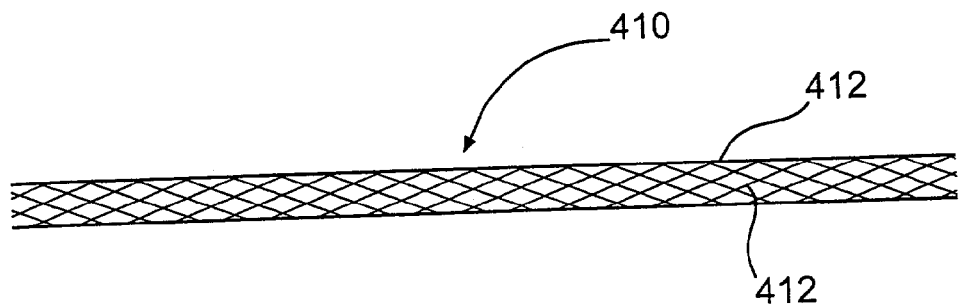
FIG. 34 is a side of a multifilament braided tension member.

FIG. 34 is a side view of a braided multifilament tension member 410. Tension member 410 includes a plurality of filaments or wires 412. It can be appreciated that numerous braiding patterns are known to those skilled in the art of multifilament members. It is anticipated that in a preferred embodiment, braided member 410 can have an optional core of fibers running parallel to an elongate axis of tension member 410. In yet another preferred embodiment, tension member 410 could have a solid wire core extending parallel to and along the longitudinal axis of tension member 410.

The tension members and anchors or anchor pads are preferably bio-resistant, i.e., resistant to physiologic attack. To improve bio-resistance, tension member and/or anchors or anchor pads can be coated with carbon material such as glass, pyrolytic carbon, diamond or graphite, zirconium nitrate or oxide. Roughened or porous urethanes, silicone or polymer coatings or sheaths can be used to promote tissue ingrowth to create a biological seal. Hydrophilic and albumin coatings can also be used. Drugs incorporated into a binder coating can also be used to reduce biological attack on the splint and irritation of tissue by the splint. Such drugs include heparin, coumadin, anti-inflammatory steroid or ASA-aspirin. The oxide layer of the underlying metal could also be optimized to improve bio-resistance. This is particularly true for stainless steel, titanium, or nickel titanium on which an oxide layer can be formed by heating the component to improve biocompatibility. Further coatings include calcium hydroxy appetite, beta tricalcium phosphate and aluminum oxide can be applied to the tension member. The tension member and/or pad or anchor pad can at least be, in part, formed from titanium to enhance electronegativity.

The anchors or anchor pads and, particularly the tension members are biocompatible, preferably antithrombogenic and made to prevent hemolysis. The coatings used to enhance bio-resistance described above can generally be used to improve biocompatibility. Since the tension member is exposed to significant blood flows through the left ventricle, in a preferred embodiment, the tension member has a generally small size and shape elliptical cross sectional shape to reduce turbulence or drag over the tension member. If such elliptical, transverse cross section tension member were used, it can be appreciated that the narrow end would be preferably oriented toward the direction of blood flow. It is also desirable to select a tension member material and shape which would not vibrate at resonant frequency under the influence of blood flow.

Where the tension member passes through the heart wall, various approaches can be taken to reduce or prevent bleeding. For example, the surface of the anchor or anchor pad and/or tension member in contact with the heart wall can be coated or include an ingrowth inducing covering such as collagen, dacron, expanded PTFE or a roughened/porous surface. A clotting inducing substance may also be bound to the tension member and/or anchor or anchor pads, such as avitene or collagen. It is also contemplated that the portion of the heart wall where the tension member passes through could be cauterized. In a preferred embodiment, the tissue can be cauterized by heating the tension member. A glue such as cyanoacrylate can also be disposed between the tension member and the heart wall to reduce or prevent bleeding from the heart wall. Mechanical means such as an O-ring or compression fitting could also be disposed between the heart wall and the tension member to reduce bleeding. A purse string suture can be placed on the heart, around the tension member adjacent the pad as well.

The tension member is preferably flexible enough to allow for changing interface conditions between the heart and the splint, and alternating pad orientation throughout the cardiac cycle. The flexibility should be sufficient enough to avoid injury to the heart or bleeding. It is also preferable that if the heart were to contract sufficiently enough to put the tension member in compression that it would readily buckle. Buckling could be promoted by providing a ribbon shaped tension member, chain link tension member, thin wire tension member, bent tension member or multi-filament tension member.

The tension member is preferably radiopaque, echo cardiographic visible, or MRI compatible or includes a marker which is radiopaque, echo visible, or MRI compatible. The preferred locations for markers would include the center of the tension member and at the ends of the tension member disposed at the heart walls. The radiopaque markers could be gold or platinum or other biocompatible metal or heavy metal filled polymeric sleeves. With respect to echo compatible or MRI compatible tension members or markers, the tension or marker are preferably non-interfering or visible. Having radiopaque echo compatible or MRI compatible tension members or markers is particularly desirable for follow-up, non-invasive monitoring of the tension member after implantation. The presence of the tension member can be visualized and the distance between two or more markers measured. Integrity of the tension member can be confirmed as well.

In a preferred embodiment, the tension member is not conductive to the action potential of muscle. This can be accomplished by insulating the tension member, anchor and/or anchor pad interface or fabricating the tension member anchor and/or anchor pad from a non-conductive metal such as titanium.

In addition to monitoring the performance of the tension member by visualization techniques such as fluoroscopy or echo imagery, sensors can advantageously be incorporated into the splints. For example, a strain gauge can be disposed on a tension member to monitor the loading on the member in use. Strain can be related to load as known to those skilled in the art by developing a stress/strain relationship for a given tension member. The strain gauge can be connected by a biocompatible lead to a conventional monitoring device. A pressure gauge formed from, for example, piezo electric material can also be disposed on the tension member to monitor filling pressures or muscle contractility.

In a preferred embodiment, a tension member can be slidably enclosed within a tube. If the tension member were to fail, the tube would contain the tension member therein.

It is anticipated that the tension member could be connected to a pacing lead. In such an instance, if the tension member were conductive, pacing signals could be conveyed along the tension member from one heart wall to another.

In use, the various embodiments of the present invention are placed in or adjacent the human heart to reduce the radius or cross-section area of at least one chamber of the heart. This is done to reduce wall stress or tension in the heart or chamber wall to slow, stop or reverse failure of the heart. In the case of the splint 16 shown in FIG. 1, a cannula can be used to pierce both walls of the heart and one end of the splint can be advanced through the cannula from one side of the heart to the opposite side where an anchor can be affixed or deployed. Likewise, an anchor is affixed or deployed at the opposite end of splint 16. Additional methods for splint placement are described in more detail in U.S. Pat. No. 6,260,552, issued on Jul. 17, 2001 and entitled "Transventricular Implant Tools and Devices" and incorporated herein by reference.

It can be appreciated that the methods described above to advance the tension members through the ventricles can be repeated to advance the desired number of tension members through the ventricle for a particular configuration. The length of the tension members can be determined-based upon the size and condition of the patient's heart. It should also be noted that although the left ventricle has been referred to here for illustrative purposes, that the apparatus and methods of this invention can also be used to splint multiple chambers of a patient's heart as well as the right ventricle or either atrium.

Figure 35:
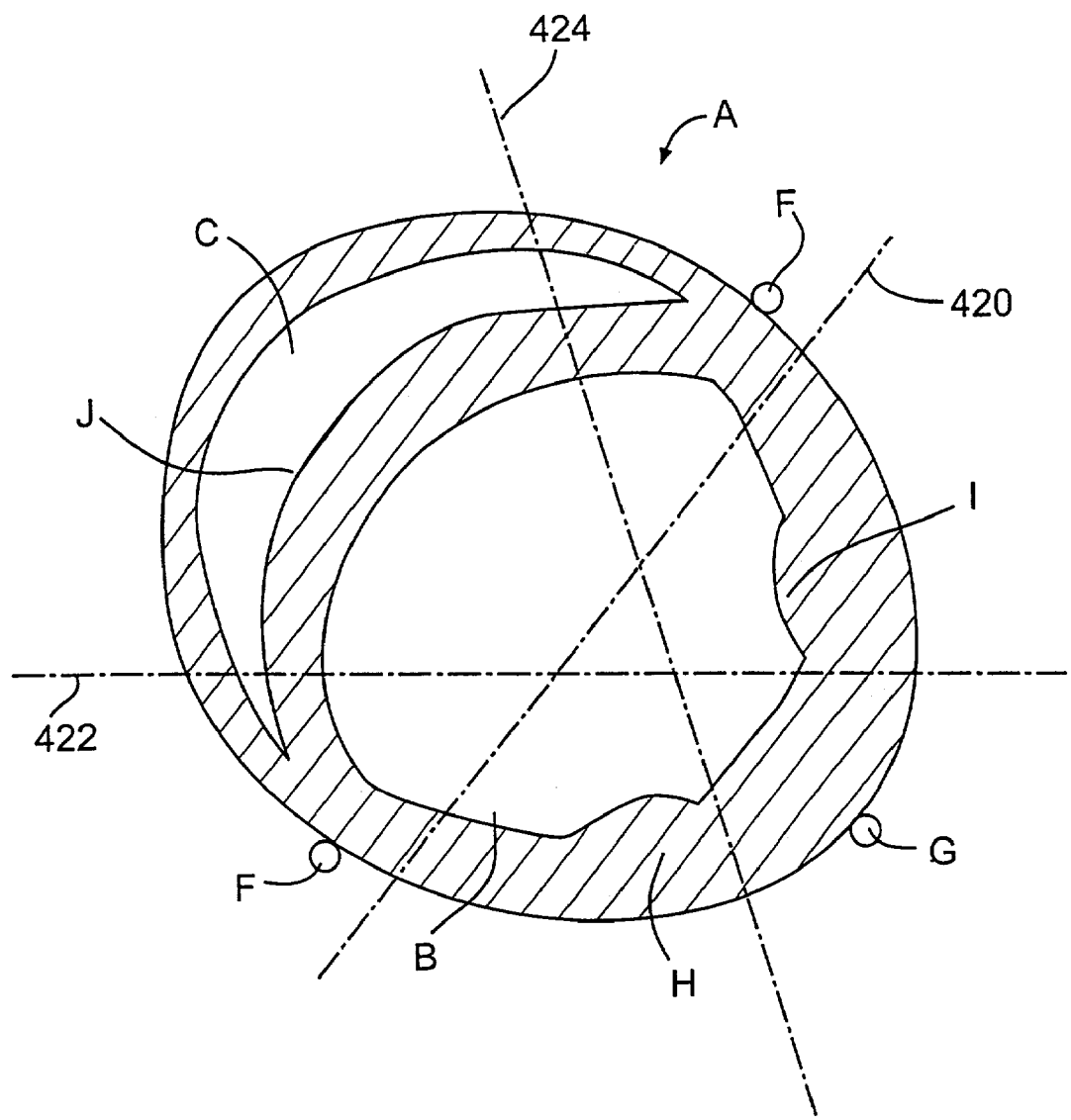
FIG. 35 is a schematic generally horizontal cross sectional view of the heart showing preferred tension member alignments.

FIG. 35 is a schematic view of generally horizontal cross section of heart A including left ventricle B and right ventricle C. Also shown are left anterior descending artery E, posterior descending artery F, obtuse marginal artery G, postero-medial papillary muscle H and antero-lateral papillary muscle 1. Shown in FIG. 35 are three generally horizontal preferred alignments for tension member placement for the splints of the present invention when used for the purpose of treating ventricular dilatation. These alignments generally met three goals of splint positioning including good bisection of the left ventricle, avoidance of major coronary vessels and avoidance of valve apparatus including chordae leaflets and papillary muscles. Alignment 420 can be referred to as the anterior/posterior (AP) position. Alignment 422 can be referred as the posterior septal/lateral wall (PSL) position. Alignment 424 can be referred to as the anterior septal/lateral wall (ASL) position.

It can be appreciated that the alignments shown are illustrative only and that the alignments may be shifted or rotated about a vertical axis generally disposed through the left ventricle and still avoid the major coronary vessels and papillary muscles. When the alignment passes through a substantial portion of right ventricle C, it may be desirable to dispose not only two pads on the exterior of the heart at opposite ends of a tension member, but also a third pad within right ventricle C on septal J. The spacing between the third pad and the pad disposed outside the heart proximate left ventricle B preferably defines the shape change of left ventricle B. This will allow the spacing of the third pad relative to the pad disposed outside the heart proximate right ventricle C to define a shape change if any of right ventricle C in view of the spacing between those pads. With the alignments as shown in FIG. 35, the third pad will be unnecessary. It is likely, however, that with alignments 422 and 424 in order to achieve the desired shape change of left ventricle B, the exterior pad of the wall proximate the right ventricle C will be drawn into contact with septal J. This will consequently somewhat reduce the volume of right ventricle C.

Figure 36:
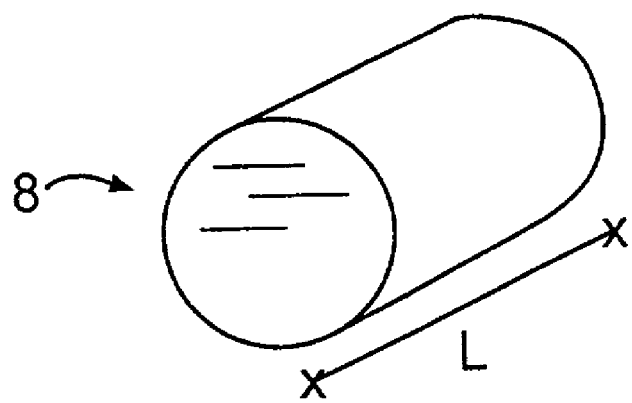
FIG. 36 is a idealized cylindrical model of a left ventricle of a human heart.

FIG. 36 is a view of a cylinder or idealized heart chamber 48 which is used to illustrate the reduction of wall stress in a heart chamber as a result of deployment of the splint in accordance with the present invention. The model used herein and the calculations related to this model are intended merely to illustrate the mechanism by which wall stress is reduced in the heart chamber. No effort is made herein to quantify the actual reduction which would be realized in any particular in vivo application.

Figure 37:
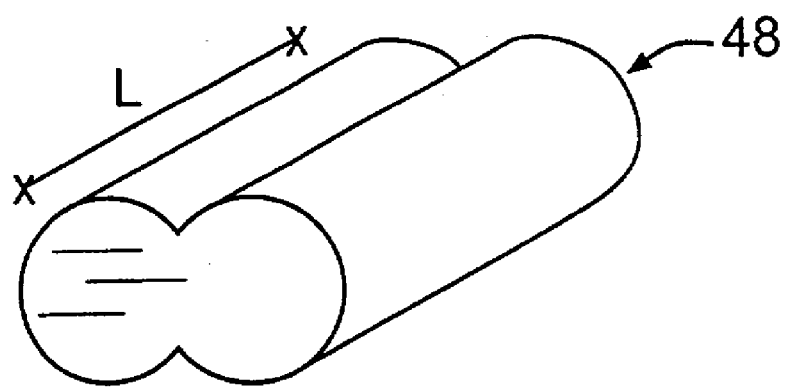
FIG. 37 is a splinted model of the left ventricle of FIG. 14.

FIG. 37 is a view of the idealized heart chamber 48 of FIG. 36 wherein the chamber has been splinted along its length L such that a "figure eight" cross-section has been formed along the length thereof. It should be noted that the perimeter of the circular transverse cross-section of the chamber in FIG. 36 is equal to the perimeter of the figure eight transverse cross-section of FIG. 37. For purposes of this model, opposite lobes of the figure in cross-section are assumed to be mirror images.

Figure 38:
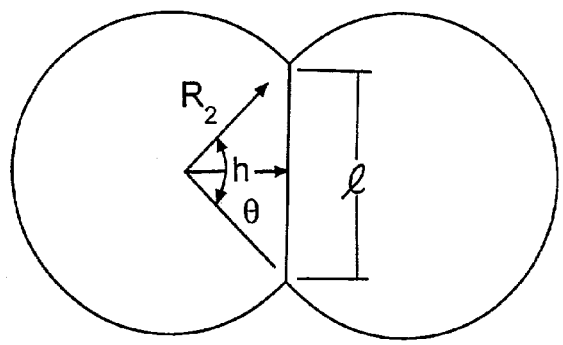
FIG. 38 is a transverse cross-sectional view of FIG. 15 showing various modeling parameters.

FIG. 38 shows various parameters of the FIG. 1 cross-section of the splinted idealized heart chamber of FIG. 37. Where l is the length of the splint between opposite walls of the chamber, $R_2$ is the radius of each lobe, θ is the angle between the two radii of one lobe which extends to opposite ends of the portion of the splint within chamber 48 and h is the height of the triangle formed by the two radii and the portion of the splint within the chamber 48 ($R_1$ is the radius of the cylinder of FIG. 36). These various parameters are related as follows:

$h = R_2 \cos(\theta/2)$ $l = 2R_2 \sin(\theta/2)$ $R_2 = R_1 \pi/(2\pi - \theta)$ From these relationships, the area of the figure eight cross-section can be calculated by:

$A_2 = 2\pi(R_2)^2(1 - \theta/2\pi) + hl$

Where chamber 48 is unsplinted as shown in FIG. 36 $A_1$ the original cross-sectional area of the cylinder is equal to $A_2$ where θ=180°, h=0 and l=2$R_2$. Volume equals $A_2$ times length L and circumferential wall tension equals pressure within the chamber times $R_2$ times the length L of the chamber.

Thus, for example, with an original cylindrical radius of four centimeters and a pressure within the chamber of 140 mm of mercury, the wall tension T in the walls of the cylinder is 104.4 newtons. When a 3.84 cm splint is placed as shown in FIGS. 37 and 38 such that l=3.84 cm, the wall tension T is 77.33 newtons.

Figure 39:
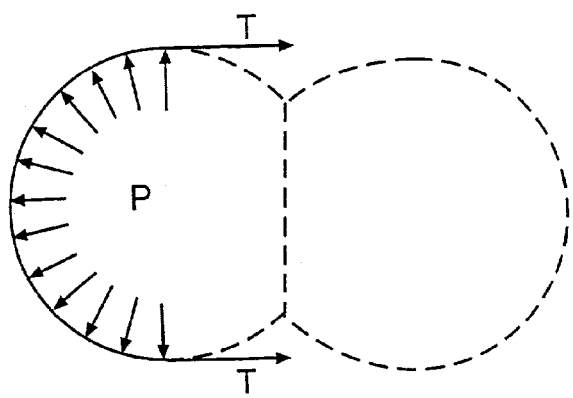
FIG. 39 is a transverse cross-section of the splinted left ventricle of FIG. 15 showing a hypothetical force distribution.
Figure 40:
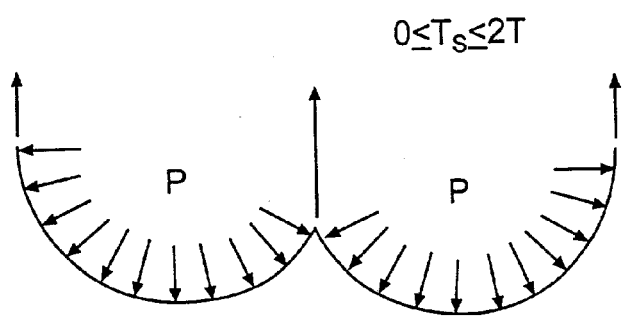
FIG. 40 is a second transverse cross-sectional view of the model left ventricle of FIG. 15 showing a hypothetical force distribution.
Figure 41:
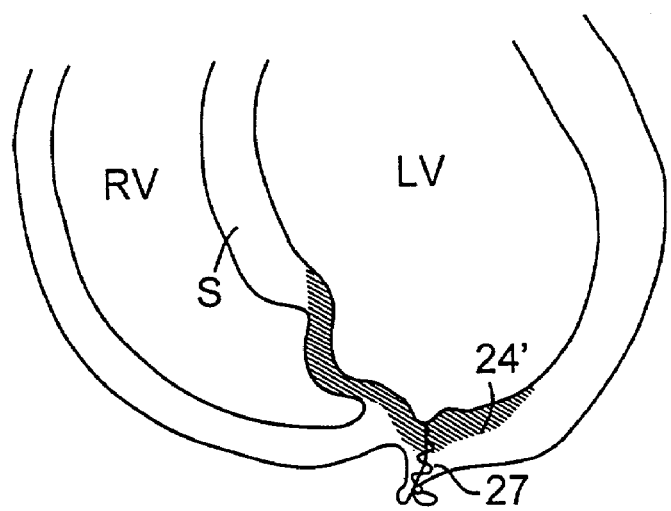
FIG. 41 is a transverse, partial cross-section of left and right ventricles showing a traditional surgical method of treating infarcted tissue regions.

FIGS. 39 and 40 show a hypothetical distribution of wall tension T and pressure P for the figure eight cross-section. As θ goes from 180° to 0°, tension $T_s$, in the splint goes from 0 to a 2T load where the chamber walls carry a T load.

In yet another example, assuming that the chamber length L is a constant 10 cm, the original radius $R_1$, is 4 cm, at a 140 mmHg the tension in the walls is 74.7 N. If a 4.5 cm splint is placed such that l=4.5 cm, the wall tension will then be 52.8 N.

When a splint is actually placed on the heart, along an alignment such as those shown in FIG. 35, the length l between the two pads as measured along the tension member is preferably 0.4 to about 0.8 and more preferably between about 0.5 to about 0.7 and most preferably about 0.6 times the distance along the length of the tension member at end diastole if the pads were not secured to the tension member and provided no resistance to expansion of the heart. A more detailed discussion of tension member length can be found in U.S. Pat. No. 6,260,552, issued on Jul. 17, 2001 and entitled "Transventricular Implant Tools and Devices" which is incorporated herein by reference.

As mentioned earlier, FIG. 17 is a partial vertical cross-section of human heart 14 showing left ventricle 10 and left atrium 22. As shown in FIG. 17, heart 14 includes a region of scar tissue 24 associated with an aneurysm. The aneurysmal scar tissue 24 increases the radius or cross-sectional area of left ventricle 10 in the region affected by the scar tissue. Such an increase in the radius or cross-sectional area of the left ventricle will result in greater wall stresses on the walls of the left ventricle, especially those walls adjacent to the aneurysm.

In addition to the various uses of the splint to treat ventricular dilatation as heretofore discussed, the inventive splint also can be used to treat infarcted tissue or aneurysms occurring on the heart wall, as illustrated by FIGS. 18 and 42–44, 46, and 47. These figures show various placements of a splint to treat infarcted tissue or aneurysms. It is to be understood that variations of these placements that have similar effects are within the scope of this invention.

Figure 42:
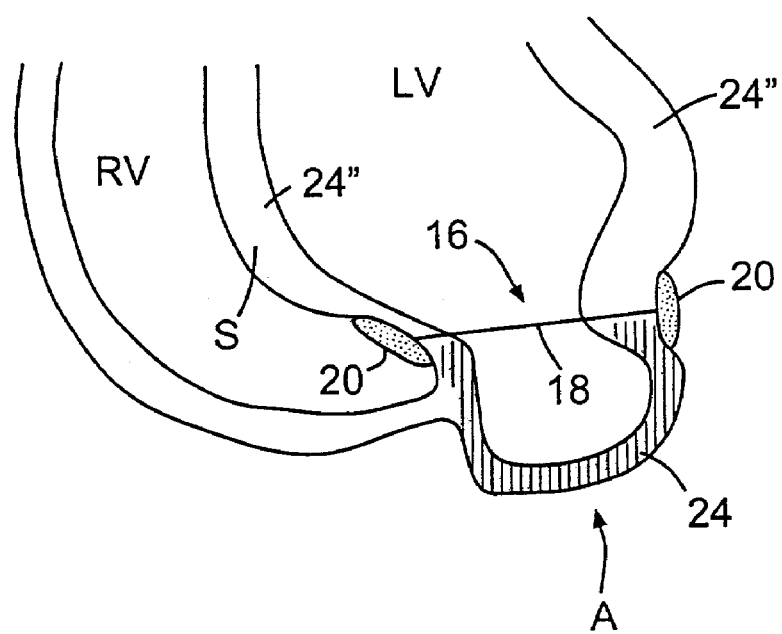
FIG. 42 is a transverse, partial cross-sectional view of left and right ventricles with an infarcted or aneurysmal region in the apical portion of the left ventricle and a splint according to an embodiment of the invention placed diametrically across the region.

FIG. 42 illustrates a method for placing a splint of the present invention to treat a heart with infarcted tissue, including an aneurysm. The particular aneurysm A shown in FIG. 42 affects the ventricular septal wall. FIG. 42 shows a partial transverse cross-section of a human heart having an aneurysm A (shown by shading) in the left ventricle wall. It is contemplated that the methods and devices of this invention also apply to treatment of hearts with akinetic scar tissue that has not progressed past an infarcted stage and into an aneurysmal stage, in which case there would be little or no bulging of the heart wall. Such a condition is shown in FIGS. 43a–43d to be described shortly. In FIG. 42, splint 16 is placed diametrically across aneurysm A to lessen the load carried by the transmural infarcted tissue 24 forming aneurysm A, as well as any adjacent border zone tissue that may be present. The border zone (although not shown in FIG. 42) is the portion of the heart wall which has a mix of contractile tissue 24" and infarcted tissue 24. Anchors 20 of splint 16 are located on the outside of the chamber walls and are placed generally adjacent to the portions of the chamber wall that transition from infarcted myocardium 24 to regions of contractile myocardium 24". Tension member 18 extends through the heart chamber with each of its ends connecting to opposing anchors 20. Anchors 20, especially when used to anchor splint 16 on septal wall S, can be of the self-deploying type disclosed in U.S. Pat. No. 6,260,552, issued on Jul. 17, 2001, entitled "Transventricular Implant Tools and Devices," the complete disclosure of which is incorporated herein by reference.

Splint 16 reduces the radius of curvature of the aneurysmal region A and the adjacent regions of the chamber wall. By reducing the radius of curvature in these regions, contractile regions 24" of the myocardium that were under high stress due to geometric abnormalities associated with an aneurysmal region A are relieved from that high stress, thereby resulting in increased pumping ability upon contraction. Even if the infarcted tissue has not led to bulging of the heart wall, reducing the radius of curvature helps to reduce some of the stress in the adjacent contractile myocardium. By increasing the pumping ability of the contractile myocardium 24", the heart can more easily pump the required blood flow output, helping to offset the pumping lost by the infarcted muscle 24. Those regions of the chamber wall that have only endocardial infarcted tissue, that is border zone regions 24', likely will experience an increase in their ability to contract and contribute to pumping.

It is also contemplated to use more than one splint, and splints having different lengths, to optimize the reduction in the radius of curvature of infarcted and aneurysmal regions and adjacent regions. Another contemplated mode of the invention includes closing off the infarcted or aneurysmal region completely by shortening the splint so that the walls adjacent the anchors contact each other. Closing off the infarcted or aneurysmal tissue from the rest of the heart chamber in this way renders this tissue completely nonfunctional with respect to contributing to the pumping. Shortening the splint to achieve contact of the heart walls may also reduce the risk of embolic thrombus because no blood would be expected to flow into the excluded region. Additionally, the need to remove any thrombus already adhered to the heart wall may be unnecessary because the thrombus would have no way of escaping back into the heart chamber to cause stroke or other malfunctions. If the infarcted or aneurysmal tissue extends to the septal wall of the chamber, the splint would be placed across the chamber so as to exclude the non-contractile tissue of the septal wall as well.

As described earlier, FIG. 18 is a vertical cross-sectional view of heart 14 as shown in FIG. 17. FIG. 18 depicts another method of the present invention, wherein splint 16 is placed to draw aneurysm A toward an opposite wall of left ventricle 10. An anchor 20 of splint 16 is placed on the outside wall of heart 14, approximately at the center of the infarcted tissue 24 forming aneurysm A. Tension member 18, connected to this anchor, is then extended across the chamber of the heart to the opposite wall and connected to another anchor 20 placed on the outside chamber wall to secure splint 16. The radius or cross-sectional area of the left ventricle affected by the infarcted tissue 24 is thereby reduced. The reduction of this radius or cross-sectional area results in reduction in the stress in the left ventricular wall and thus improves heart pumping efficiency. Furthermore, infarcted tissue 24 is supported by anchor 20 of the splint to prevent any additional bulging of the wall or progression of the infarcted tissue to other areas of the myocardium.

Bringing infarcted tissue 24 into the chamber, as shown in FIG. 18, likely reduces the risk of thrombosis due to contact between the endocardial infarcted tissue and circulating blood flow occurring in these regions of the chamber. Clots are less likely to form on tissue that is subject to an active flow of blood. The forces associated with such flow diminish stagnation points that allow clots to form and adhere to the wall more readily.

Figure 43A:
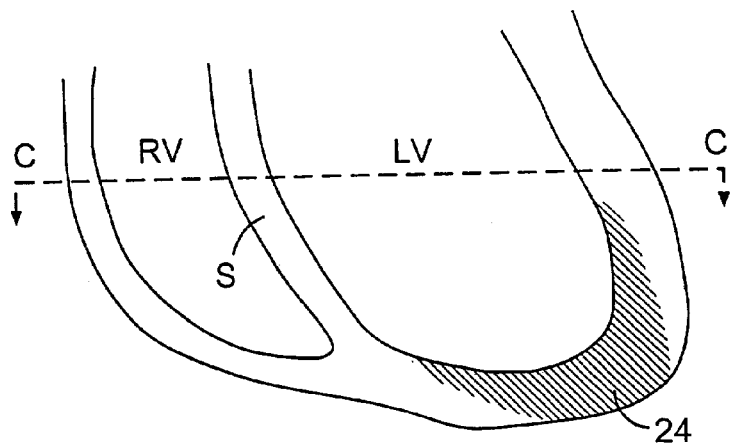
FIGS. 43a–43b are long axis cross-sectional views of left and right ventricles showing a region of infarcted tissue in a portion of the basal left ventricle and a splint according to an embodiment of the invention placed across the infarcted region.
Figure 43B:
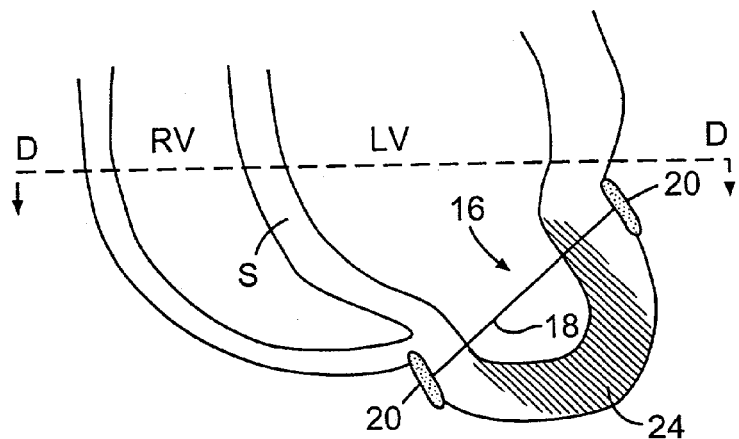
Figure 43C:
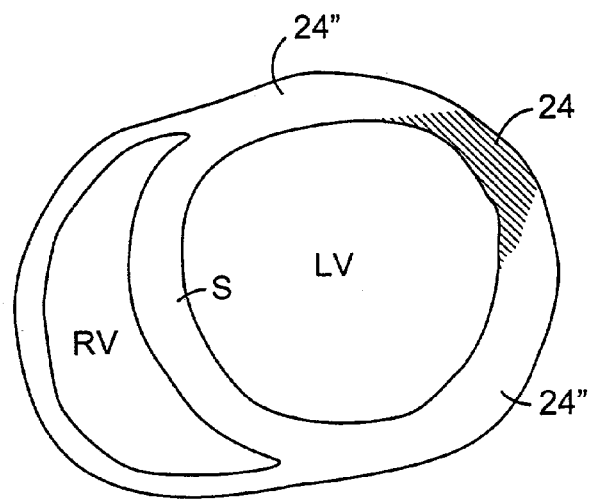
FIGS. 43c–43d are short axis cross-sectional views of the heart in FIGS. 43a–43b shown from the perspective of lines c—c and d—d, respectively.
Figure 43D:
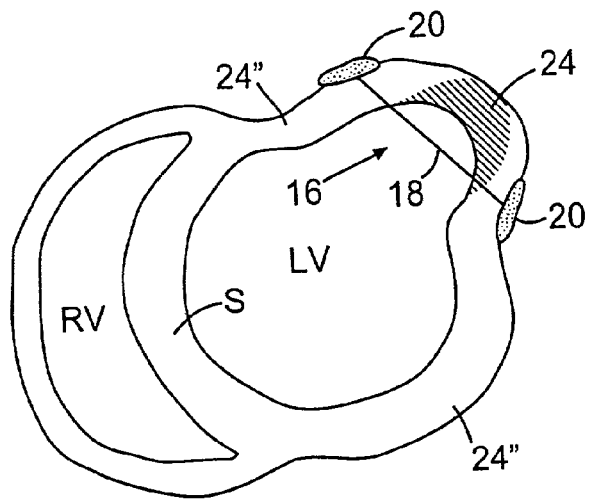

FIGS. 43a–43d depict the use of splint 16 to treat a heart chamber having a discrete zone of akinetic infarcted myocardium 24 that has not yet developed into an aneurysm. FIGS. 43a and 43b depict a long axis (or essentially vertical) cross-sectional view of the heart, with FIG. 43b showing the placement of splint 16. FIGS. 43c and 43d show the heart in short axis (or essentially horizontal) cross-section, with placement of splint 16 shown in FIG. 43d. In FIGS. 43b and 43d, splint 16 is shown treating a heart including infarcted tissue 24 that does not affect septal wall S. Thus, both anchors 20 are placed on exterior wall portions of left ventricle LV. However, it is contemplated that a splint could be used to alter the geometry of the chamber in cases in which an infarcted region does affect septal wall S.

By utilizing splint 16, the radius of curvature, particularly with respect to the short axis direction, is reduced. This reduction of curvature facilitates the pumping ability of any portions near the infarcted region 24 that have some contractile potential by reducing wall stress in the region. By allowing this once marginally contractile tissue to increase its contractile ability, the heart improves its ejection fraction, cardiac reserve, and muscle contractibility. Additionally, the remainder of the ventricle also experiences a reduced radius of curvature, as shown in FIG. 43b and 43d, further facilitating the contractile ability of the entire ventricle. By improving the contracting ability of the entire chamber, the heart has the ability to account for the lost pumping ability of the infarcted myocardium 24. Left untreated, this condition causes the rest of the ventricle to attempt to contract more, ultimately over-working and weakening the heart to a greater degree.

Figure 44A:
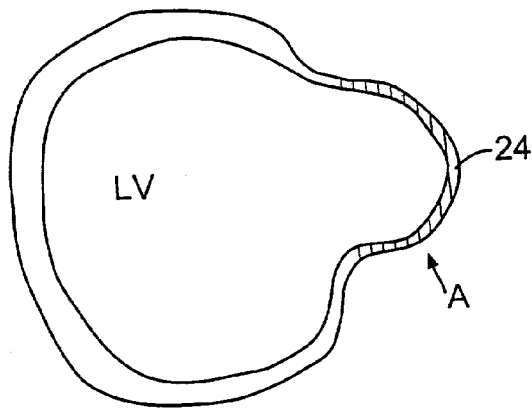
FIGS. 44a–44b are short axis cross-sectional views of the left ventricle having an aneurysm and a placement of a splint according to an embodiment of the present invention with respect to the aneurysm to treat the heart.
Figure 44B:
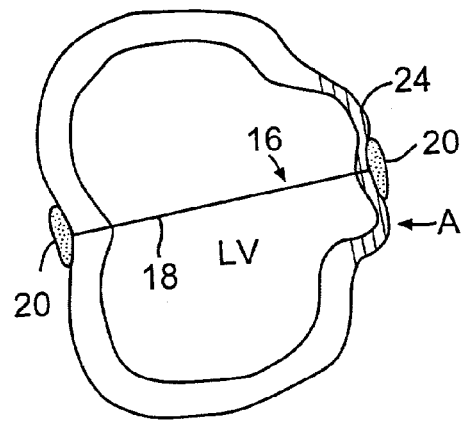

FIGS. 44a–44b show a cross-sectional view of the left ventricle with an aneurysmal region A. As shown in FIG. 44b, splint 16 can also be placed such that one anchor 20 engages approximately the center of the bulge formed by aneurysm A. Tension member 18 is then extended through the center of aneurysm A and across left ventricle LV to anchor splint 16 to a point on the surrounding heart wall substantially opposite to aneurysm A. This positioning of splint 16 tends to bring the aneurysmal bulge in line with the normal curvature of the heart wall. By this placement of splint 16, it is expected that greater blood flow would occur in the region of aneurysmal tissue A, potentially reducing thrombus formation.

Figure 45:
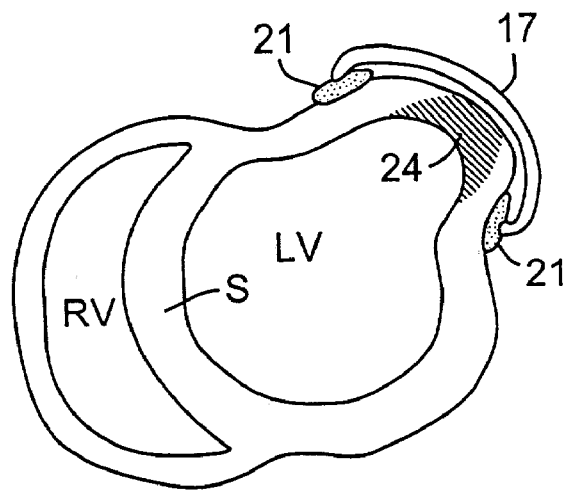
FIG. 45 is a short axis cross-sectional view of the right and left ventricles having an infarcted region like that shown in FIG. 43c and an external splint device according to an embodiment of the present invention placed to treat the infarction.

FIG. 45 shows the use of a completely external device to treat a heart having a zone of infarcted tissue 24. In the embodiment shown in FIG. 45, the external splint device is an external frame generally in the form of a clamp 17 with anchor pads 21 on each end of the clamp. The clamp 17 is configured to exert a compressive force on the heart wall to cause shape change of the heart chamber. Other external splint devices, in addition to clamp 17, that are contemplated for use in treating a heart having infarcted myocardium are disclosed in U.S. Pat. No. 6,183,411, issued on Feb. 6, 2001, and entitled "External Stress Reduction Device and Method," the complete disclosure of which is incorporated herein by reference. In addition to the benefits described above with respect to using a splint to treat a heart having infarcted tissue, external splint devices such as that shown in FIG. 45 include the potential further advantage of significantly reducing the possibility of thrombus formation resulting from surfaces of devices that contact blood flowing through the chamber.

Figure 46A:
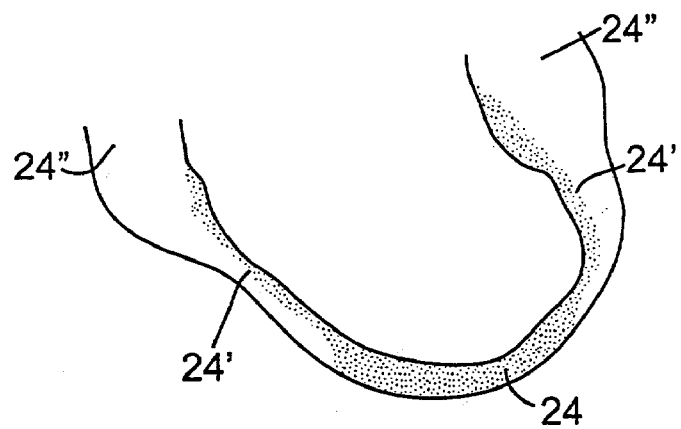
FIGS. 46a–46c show transverse, partial cross-sectional views of a left ventricle having an infarcted region, illustrating the combined inventive method of surgical removal of the infarcted tissue and placement of a splint according to an embodiment of the present invention.
Figure 46B:
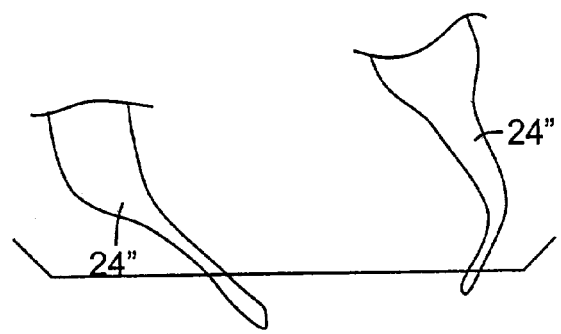
Figure 46C:
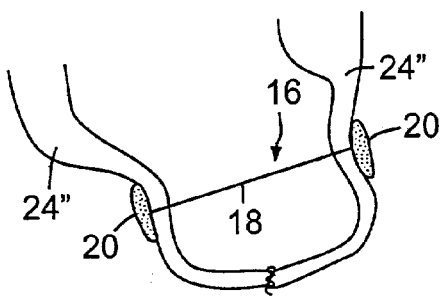

Another use for splint 16 in treating heart chambers having infarcted or aneurysmal tissue is shown with reference to FIGS. 46a through 46c. This method combines the use of splint 16 with the traditional surgical technique in which the infarcted tissue is removed. By using the techniques described later for identifying and distinguishing between healthy tissue and infarcted tissue, all of the infarcted myocardium 24 shown in FIG. 46*a* can be excised from the chamber, as shown in FIG. 46*b*. The separated portions of the chamber walls will then be sutured back together. Splint 16 is then placed diametrically transverse to the portion of heart chamber walls 24" that have been partially excised, as shown in FIG. 46*c*. Anchors 20 are placed between the portions of the chamber wall from which infarcted tissue 24 was removed and portions of the chamber wall that contained contractile tissue throughout its thickness. Because only contractile tissue regions 24" would remain after this procedure, as opposed to conventional surgery which leaves some of the infarcted tissue occurring in border zone regions in place, contractile function, and thus cardiac function, likely would improve. Splint 16 reduces the radius of curvature in those thinner regions of the walls that remain after the surgery, allowing them to produce stronger contractions and relieving stress in those wall portions.

If the infarcted tissue is not removed, as shown in FIG. 42, the border zone cannot contribute significantly to the pumping function, for the contractile muscle must contract against the stiffness of the infarcted muscle. But, with the infarcted tissue removed, the thin contractile section of myocardium shown in FIG. 46*c* can be made to contract and contribute to pumping, particularly since splint 16 has reduced stress enough to allow the thin region of tissue to exert the required pressure to pump. In addition to combining the surgical excision of the infarcted tissue with the use of a splint of the present invention, an external device, like clamp 17 shown in FIG. 45, can also be combined with the surgical technique. Such an external device would be placed with respect to the heart chamber walls such that its anchors are disposed in the approximate locations as anchors 20 on splint 16, and the device between the anchors could extend around the portions of the walls that have been sutured together. It is contemplated that the splint 16 could be used in hearts where the aneurysm involves the septal wall of the ventricle. Similar to the splinting shown in FIG. 42, one or both anchor pads could be self-deploying.

Figure 47:
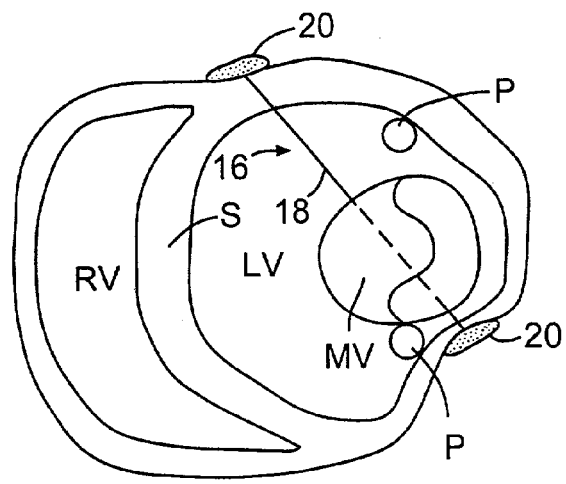
FIG. 47 is a short axis cross-sectional view of the left and right ventricles including a view of the mitral valve with an infarcted or aneurysmal region in a portion of the basal left ventricle and a splint according to an embodiment of the invention placed in the vicinity of the mitral valve.

Another use of the splint to treat infarcted or aneurysmal tissue near the base of a mitral valve MV is shown in FIG. 47. In this embodiment, the splint is placed such that its anchors 20 are diametrically opposed to one another across an aneurysm, or generally dilated annular region, located in a portion of the basal left ventricle in the vicinity of mitral valve MV. Anchors 20 are placed on the outer wall of left ventricle LV with tension member 18 of splint 16 drawn through the heart chamber and diametrically across the infarcted or aneurysmal region. The dotted line of tension member 18 shown in FIG. 47 illustrates that splint 16 lies below mitral valve MV. Placing the splint in this manner results in the papillary muscles P of mitral valve MV or the leaflets of mitral valve MV being drawn together and reduces the risk of mitral regurgitation. In addition, splint 16 reduces the radius of curvature of the aneurysmal or infarcted region. As previously described, this reduction lowers the stress in the heart wall, improving pumping effectiveness. FIG. 47 shows the placement of splint 16 such that both anchors are disposed on external walls of the left ventricle. It should be noted that the splint also could be placed so that one anchor is disposed on septal wall S, in which case a self-deploying anchor preferably would be used. Also, tension member 16 may be made to curve between anchors 20 in order to avoid damaging internal structures of the ventricle.

Figure 48A:
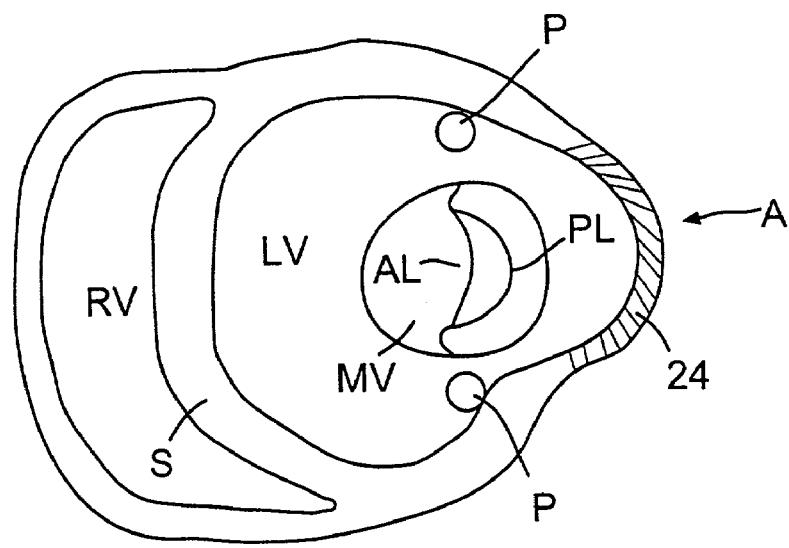
FIGS. 48a–48b are short axis cross-sectional views of the left and right ventricles and a view of the mitral valve with an aneurysmal region in a portion of the basal left ventricle and an external device according to an embodiment of the invention placed in the vicinity of the mitral valve and aneurysm.
Figure 48B:
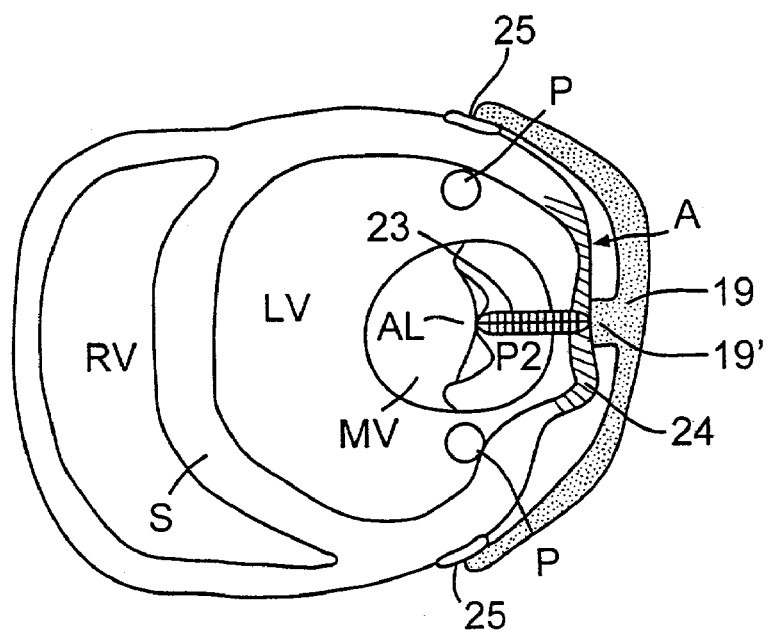

FIGS. 48*a*–48*b* show the use of an external splint device to treat a heart having an aneurysm A in the vicinity of mitral valve MV. As a result of the aneurysm, the anterior leaflet AL and posterior leaflet PL of mitral valve MV have separated causing mitral regurgitation, as shown in FIG. 48*a*. FIG. 48*b* show the placement of an external splint device having a clamp portion 19 connecting two anchors 25. It is contemplated that the external splint device used to treat this particular heart condition may also include a protrusion 19' as part of clamp portion 19. In placing clamp 19 on the heart, protrusion 19' engages aneurysm A so as to push aneurysm A toward a center of the ventricle. Additionally, a stabilizing bar 23 could be attached to the end of protrusion 19'. Stabilizing bar 23 is configured to extend through the heart chamber wall and anchor to the edge of posterior leaflet PL of mitral valve MV to bring the leaflet in close proximity to anterior leaflet AL. Such a stabilizing bar may be made of a semi-rigid, or rigid, material such as implantable metals or other suitable material. While FIGS. 48 and 49 show the use of various splints associated with an aneurysm in the vicinity of the mitral valve, it is contemplated to utilize splints also in the case where there is no true aneurysm, but an area of infarcted tissue near the mitral valve.

Figure 49A:
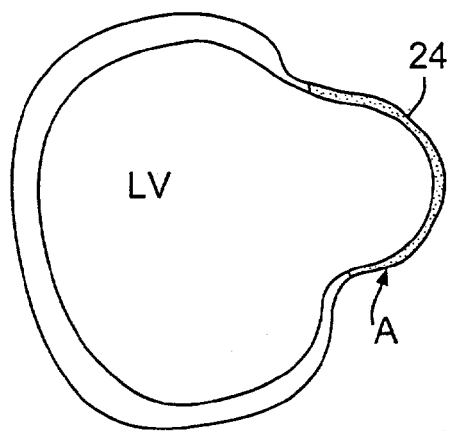
FIGS. 49a–49b are transverse cross-sections of a left ventricle having an aneurysmal region and the placement of a staked patch according to an embodiment of the present invention.
Figure 49B:
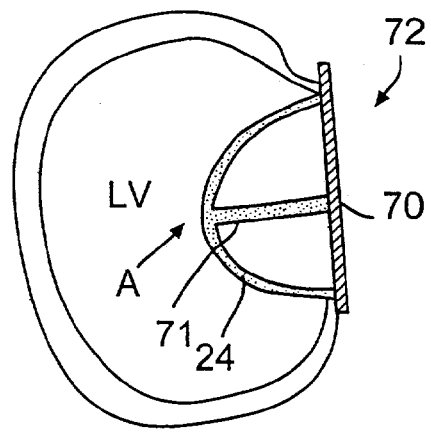

The present invention also includes myocardial patches and related methods used to treat aneurysms. FIGS. 49*a*–49*b* illustrate one preferred embodiment of the invention. FIG. 49*a* shows left ventricle LV with an aneurysm A in a portion of the chamber wall. FIG. 49*b* illustrates placement of a staked patch 72 according to an embodiment of the present invention used to treat aneurysmal bulge A. Staked patch 72 includes a patch 70, made of Dacron or PTFE for example, and an elongated member 71 secured to the patch. When staked patch 72 is secured into position (by sutures or the like) over the surface of aneurysmal bulge A, elongated member 71 pushes on the aneurysmal tissue region. Staked patch 72 pushes bulge A into the heart chamber. This pushing likely will result in an even further reduction in the stresses experienced by the adjacent heart wall due to the reduction in the radius of curvature resulting from drawing adjacent regions in toward each other when the patch is in place. Such further reduction in stress would tend to promote a more organized healing of the scar tissue region and prevent progression of the scar into other healthy myocardium. Additionally, by pushing the bulge into the chamber space, thrombosis is less likely to occur because of the active blood flow past the surface of the bulge.

As shown in FIG. 49*b*, staked patch 72 has a single stake 71 secured to the patch in a substantially perpendicular direction. However, it is contemplated that several stakes could be secured to the patch depending on the size of the affected tissue area to be treated. Additionally, stakes could be secured in various orientations, including skewed orientations, relative to the patch. The stakes have different sizes in order to optimize the degree and direction in which the bulge is pushed in, especially when the bulge has a non-uniform surface configuration. The stakes may be rigid or semi-rigid and may be manufactured from implantable metals and polymers, or other suitable materials of similar characteristics.

A three-dimensional patch also is contemplated by the present invention. Such a patch could be inflatable or solid. The patch would consist of an essentially flat surface configured to lie flush with the epicardial surface and a bulging surface that would engage with the aneurysmal region to push the aneurysm into the chamber in a manner similar to the stake described above. A suture ring maybe placed around the perimeter of the flat surface to secure the patch into place on the heart.

A further embodiment of the present invention is a shrinkable patch for treating aneurysms. For example, such a patch may be made of heat-shrinkable material and applied via sutures to the aneurysmal tissue region while the tissue is in a relaxed state. Gentle heat, such as that produced by, for example, a hot air gun, an infrared heating lamp, or other similar heating mechanisms, would then be applied to shrink the patch. This shrinking also will cause the size of the affected area to be decreased by being pulled in tightly with the shrinking patch, thereby reducing the radius of curvature of the adjacent myocardium. The patch may be made of any suitable material compatible with the human body and having heat-shrinking characteristics. Examples of such a material include oriented polyethylene, oriented polypropylene, and a woven Dacron polyester of partially-oriented yarn. Partially-oriented yarn is capable of significant longitudinal shrinkage when heated. Additionally, targeting and heating certain areas yields a non-uniform shrinking that more precisely tailors the resulting configuration of the patch and the affected tissue region.

Figure 50A:
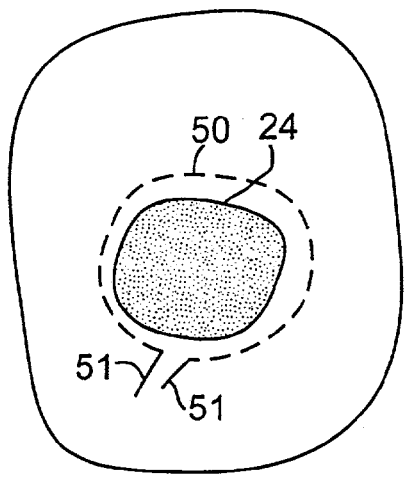
FIGS. 50a–50b are planar views of an infarcted or aneurysmal tissue region with a purse-string suture according to an embodiment of the present invention.
Figure 50B:
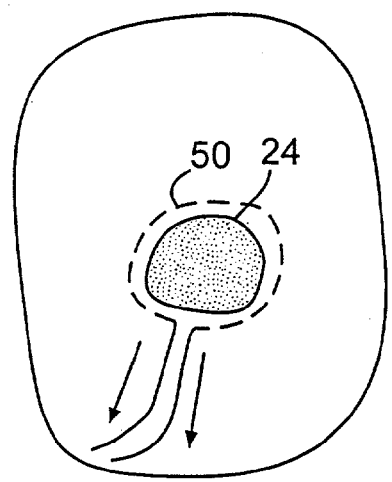

Another embodiment of the present invention, which may be used either alone or in combination with a patch, is a purse-string suture 50, as shown in FIGS. 50a–50b. In this embodiment, a suture 50 is placed to encircle the affected tissue area 24, as shown in FIG. 50a. Suture 50 has free ends 51 that are pulled to draw in suture 50 and reduce the perimeter of the affected tissue, as shown in FIG. 50b. Free ends 51 are then secured so as to keep the gathered tissue region in place. The securing can be accomplished by tying free ends 51 to one another or by some like means. By gathering the infarcted tissue together and reducing the perimeter, tension in the walls adjacent to the infarcted tissue 24 decreases due to the reduction in radius of the wall in that region. Thus, improved contractile function of the adjacent tissue is expected. Purse-string suture 50 could be drawn in to such an extent that the outer walls of the perimeter of infarcted tissue 24 contact each other. Drawing the infarcted tissue 24 to this extent cuts off the tissue completely from the rest of the heart chamber and renders it non-functional. In addition to the purse-string suture 50, a patch may be applied to support any bulging tissue area that remains after application of suture 50, as well as provide a more secure means of maintaining the gathered portions of the myocardium.

Figure 51A:
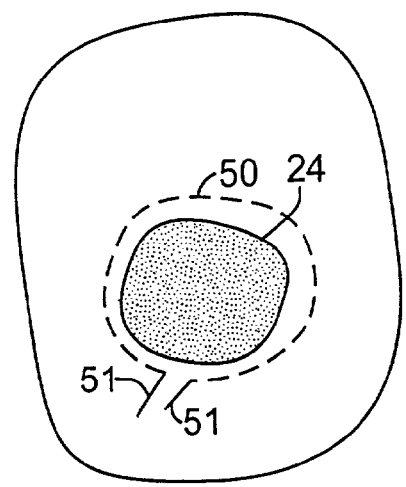
FIGS. 51a–51c are planar views of an infarcted or aneurysmal tissue region and a purse-string suture and enclosure member according to an embodiment of the present invention.
Figure 51B:
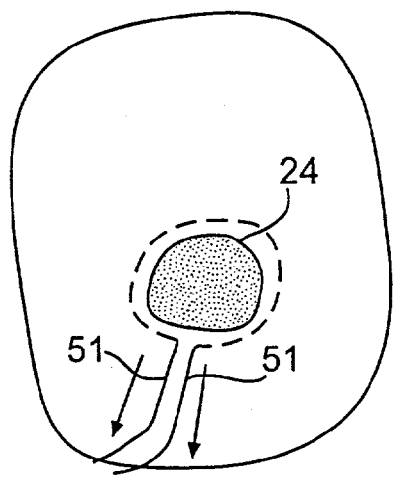
Figure 51C:
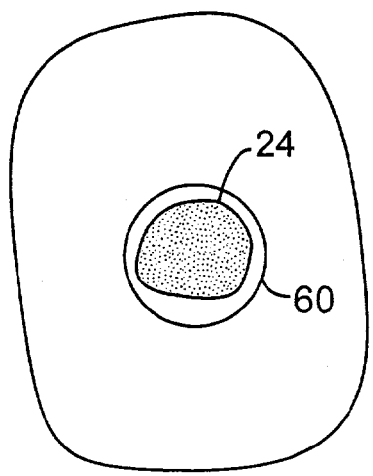

FIGS. 51a–51c illustrate a further embodiment of the present invention, the combination of a purse-string suture and an enclosure member 60. In this embodiment, purse-string suture 50 is applied to infarcted or aneurysmal tissue 24 as described above with reference to FIGS. 50a–50b. After the suture is pulled tight to gather the affected tissue region in, an enclosure member 60 is secured into place. As shown in FIG. 51c, enclosure member 60 is placed around the gathered tissue 24 so that substantially all of the infarcted tissue is contained inside enclosure member 60. In a preferred form of the invention, sutures are used to secure the enclosure member 60 into place, however other securing means are also contemplated. Enclosure member 60 preferably is made from a substantially rigid material, for example stainless steel, semi-rigid material, or any other material exhibiting like characteristics such as, for example, polyamide imide, titanium, or ultra high molecular weight polyethelene, in order to carry the load created by the gathered infarcted tissue. Because of its relative rigidity, enclosure member 60 withstands the load of the gathered tissue better than sutures alone and contains the progression of the infarcted tissue. Although FIG. 51c shows a ring as enclosure member 60, other shapes may be used to serve the inventive purposes. Overall, regardless of the shape of enclosure member 60, its perimeter should be selected to have approximately the same shape as the perimeter of the infarcted tissue region once it has been gathered together by purse-string suture 50.

Figure 52A:
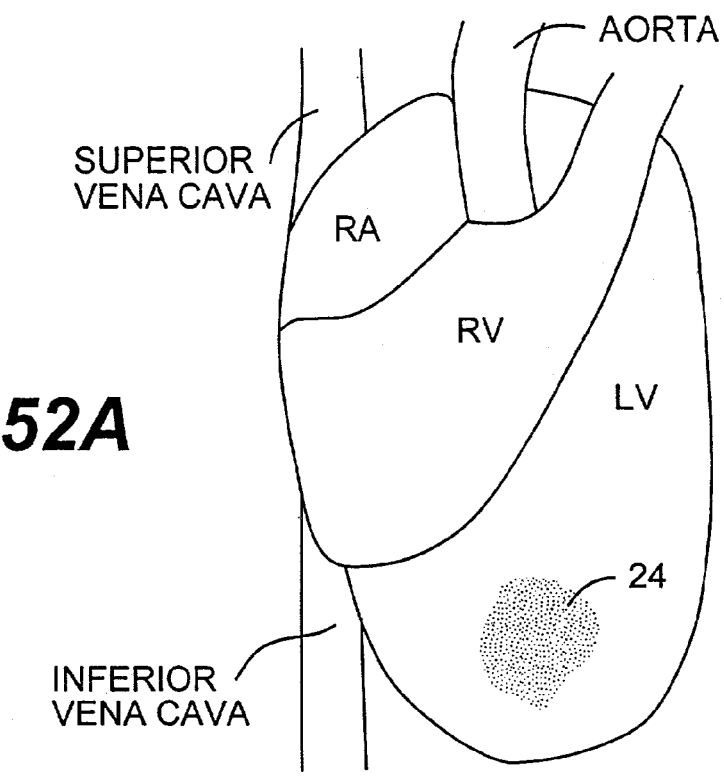
FIGS. 52a–52c are planar exterior views of the heart with an infarcted region of tissue in the left ventricle and an enclosure member according to an embodiment of the invention, showing one configuration during application of the member and a second configuration after application of the member.
Figure 52B:
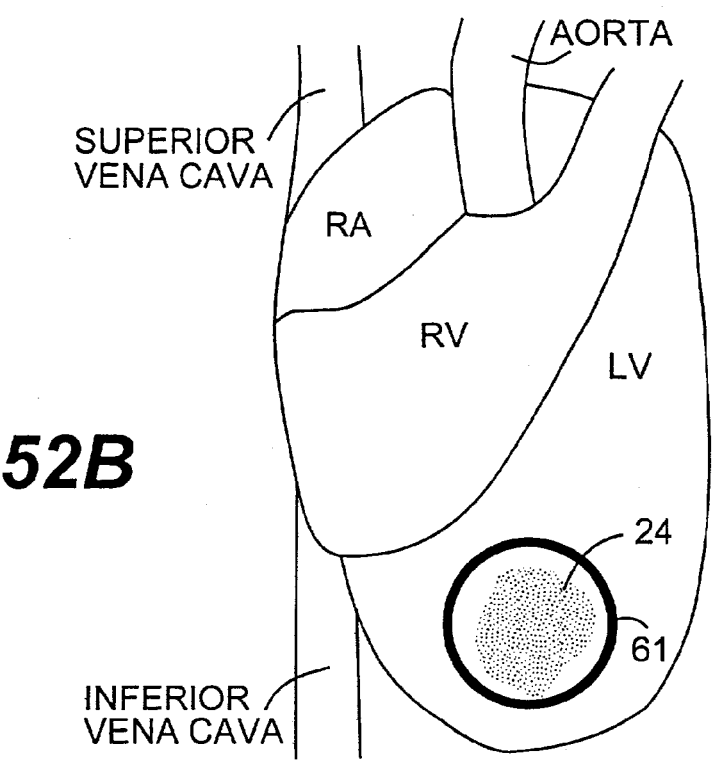
Figure 52C:
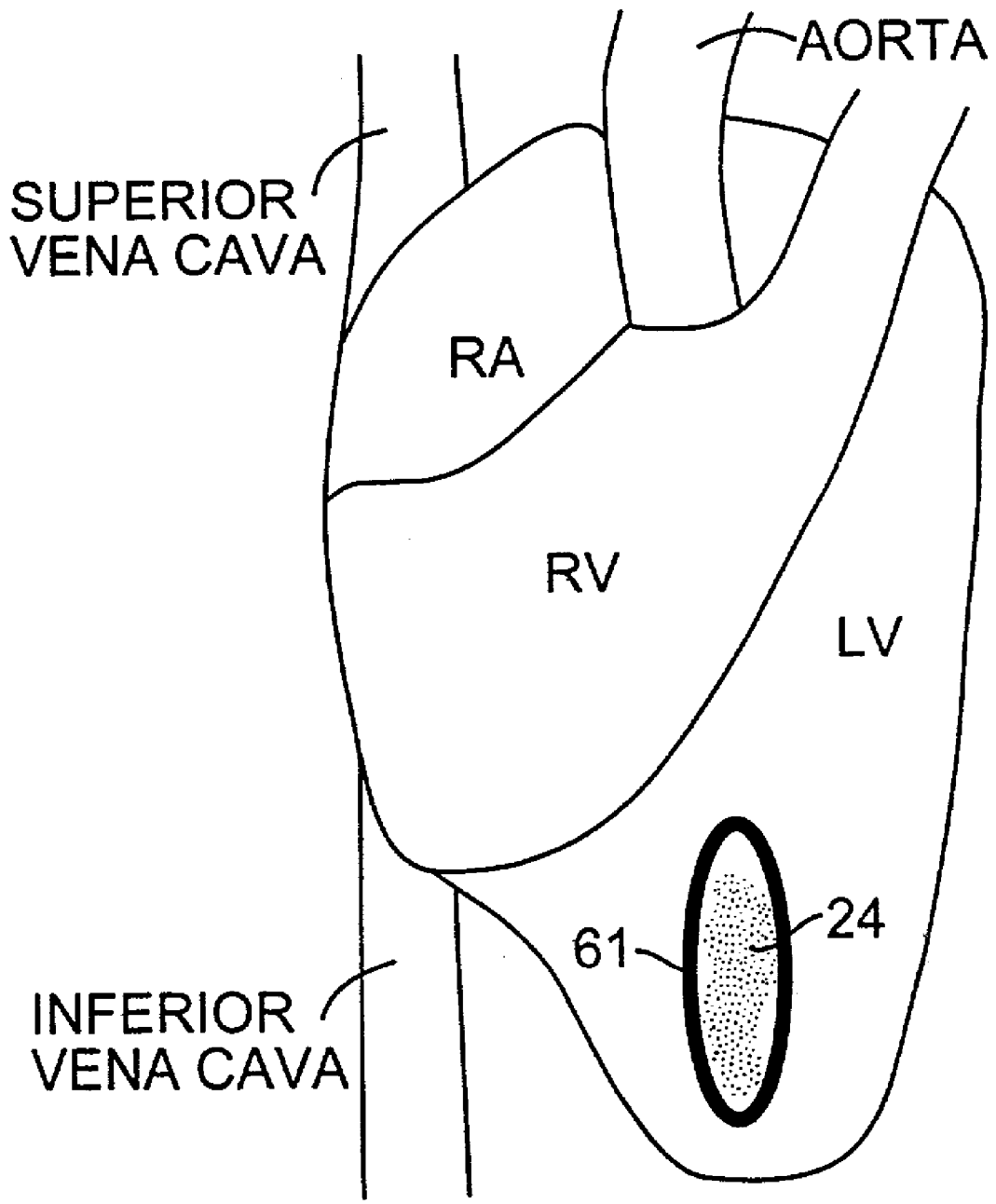

Another enclosure device is shown in FIGS. 52a–52c. FIG. 52a shows a region 24 of infarcted myocardium on left ventricle LV. Other heart structure shown in these figures includes the right ventricle RV, the right atrium RA, the superior and inferior vena cavas, and the aorta. The inventive enclosure member 61 of FIGS. 52a–52c is configured to change from a circular shape to an elliptical or oval shape. Such an enclosure member can be fabricated from a shape memory alloy, such as nitinol, or other similar suitable material, and processed such that it has a circular shape at a temperature below its transformation temperature, which is approximately equal to body temperature. Upon reaching the transformation temperature, the ring, comprised of the shape memory material, alters its configuration to the shape of an ellipse or oval, or other suitable configurations. During surgical application, the temperature of the heart is below body temperature and therefore ring 61 remains in the circular shape during application of ring 61 to the heart, as shown in FIG. 52b. After installation of the ring is complete, the heart reaches normal body temperature, transforming ring 61 into the elliptical or oval shape, as shown in FIG. 52c. this shape transformation deforms the infarcted region of tissue on the heart wall to change the shape and/or size of the heart chamber, relieve stress on the heart walls, and improve overall contractile function of the heart. In a preferred embodiment, infarcted region 24 deforms in a short axis direction, as shown in FIG. 52c.

Alternatively, enclosure member 61 can be formed of a spring metal, such as, for example, high tensile strength stainless steel. When such a material is used, the enclosure member is initially processed into the elliptical or oval configuration. The enclosure member is then attached around a circular polymer, or other suitable material, sheet to form and maintain a circular shape during attachment of the ring to the ventricle. Once attached, the circular polymer sheet is removed, causing the enclosure member to spring back to its original elliptical shape.

Other embodiments of the present invention include enclosure members that deform non-uniformly, either by having a non-uniform configuration at the shape memory transformation temperature, or at the initial processing shape of the spring metal. It also should be noted that enclosure member 61 can take on any suitable shape both before application and after, depending on such factors. as, for example, the particular infarcted region to be treated and the desired final radius of curvature.

Figure 53A:
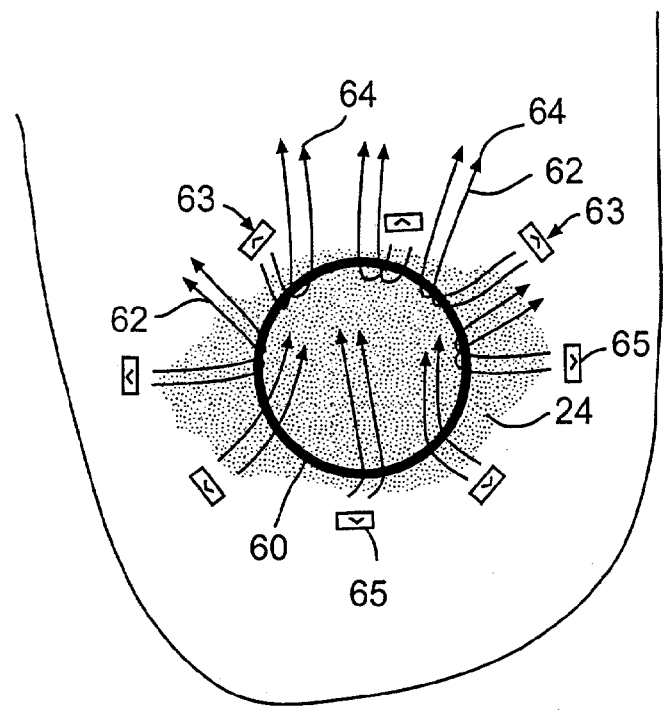
FIGS. 53a–53b are planar views of an infarcted or aneurysmal tissue region and placement of a tie enclosure according to an embodiment of the present invention.
Figure 53B:
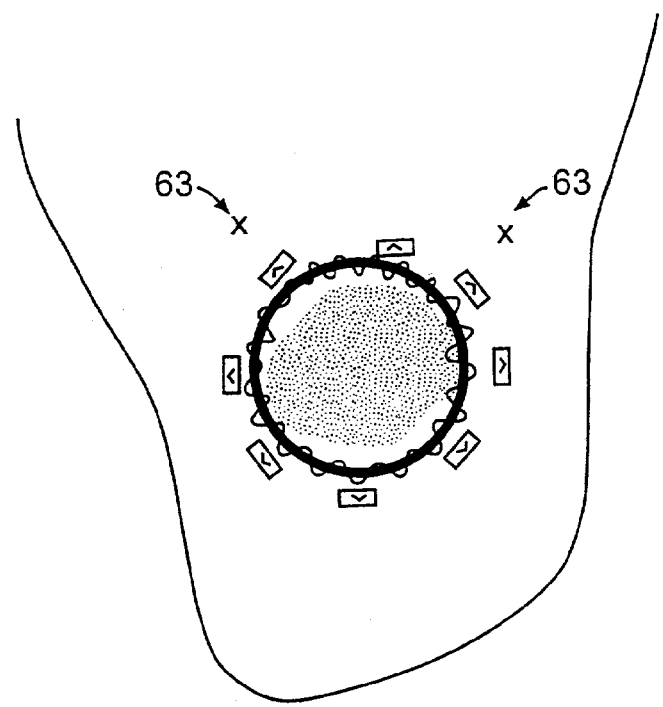

FIGS. 53a–53b illustrate a tie enclosure, a further embodiment of the invention and a variation on the use of the enclosure member. The tie enclosure includes a plurality of sutures 62 having free ends 64. Sutures 62 secure around the perimeter of the infarcted or aneurysmal tissue 24, as shown in FIG. 53a. Sutures 62 are secured at points 63 using pledgets 65. Enclosure member 60 is then placed over the affected tissue region and free ends 64 of the plurality of sutures 62 are extended through enclosure member 60 to pull sutures 62 through enclosure member 60 as well. By pulling on free ends 64 of sutures 62, the infarcted or aneurysmal tissue region 24 is again gathered and its perimeter reduced. The tissue is drawn so that pledgets 65 ultimately are adjacent enclosure member 60. The tissue, attached to the sutures, is drawn through enclosure member 60, and once in place, enclosure member 60 can be sutured to the myocardium. Free ends 64 of sutures 62 are drawn until pledgets 65 are brought close to enclosure member 60. Sutures 62 are then tied to the enclosure member 60. Additionally, enclosure member 60 may be directly sutured to the myocardium, as shown in FIG. 53b. Again, drawing in the aneurysmal tissue region reduces stress on the chamber walls, hinders the progression of the infarction, and results in a more uniform scar formation, and reduces the radius of curvature, and therefore the stress, in the region of the chamber adjacent the infarction, as well as more global reduction of radius of curvature.

The tie enclosure also allows for non-uniform drawing in of the affected tissue region by using a plurality of sutures of varying lengths. Thus, the tie enclosure allows for particular regions of the aneurysm or infarction to be targeted and drawn in while others are left intact or drawn in to a lesser degree. This allows for a more precise change in geometrical configuration that may be necessary due to non-uniformities existing in the initial geometry of the infarcted or aneurysmal region. Enclosure member 60 also may be made of a flexible material so as to allow enclosure member 60 to take on a non-uniform configuration when sutures 62 are drawn and secured.

As discussed previously, enclosure member 60 may be made of a rigid, semi-rigid, or flexible material, depending on the particular application for which the device will be used. The shape of enclosure member 60 can be that of a ring as shown in FIGS. 53a–53b or can be another shape, as long as the perimeter of enclosure member 60 is less than or equal to that of the drawn in tissue region.

Using enclosure member 60 and sutures 62 in the manner described with respect to FIGS. 53a–53b, wider zones of infarcted or aneurysmal tissue preferentially may be drawn further toward enclosure member 60, thereby maximizing the radius reduction in the direction of the widest dimension. This enables portions of the ventricle that are the most affected by the infarction to experience the greatest radius reduction and therefore the greatest stress relief.

Figure 54:
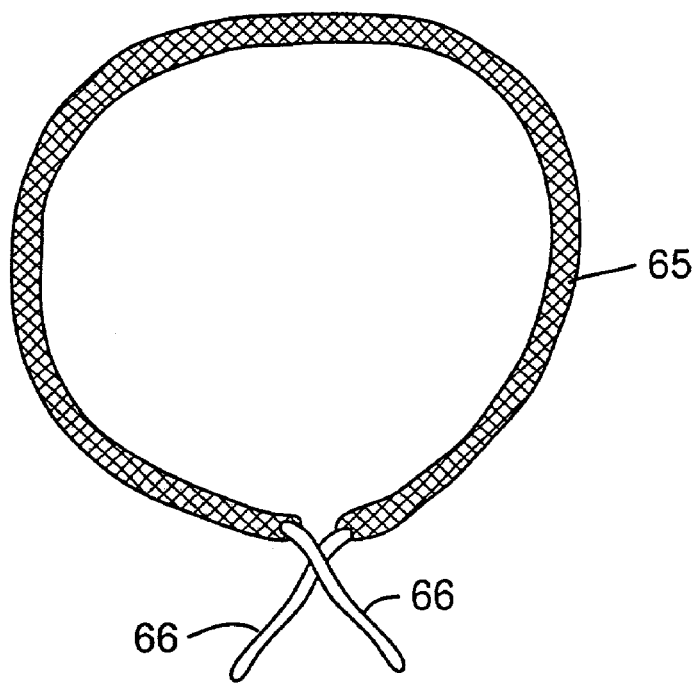
FIG. 54 is a planar view of yet another embodiment of an enclosure member according to an embodiment of the present invention.
Figure 55:
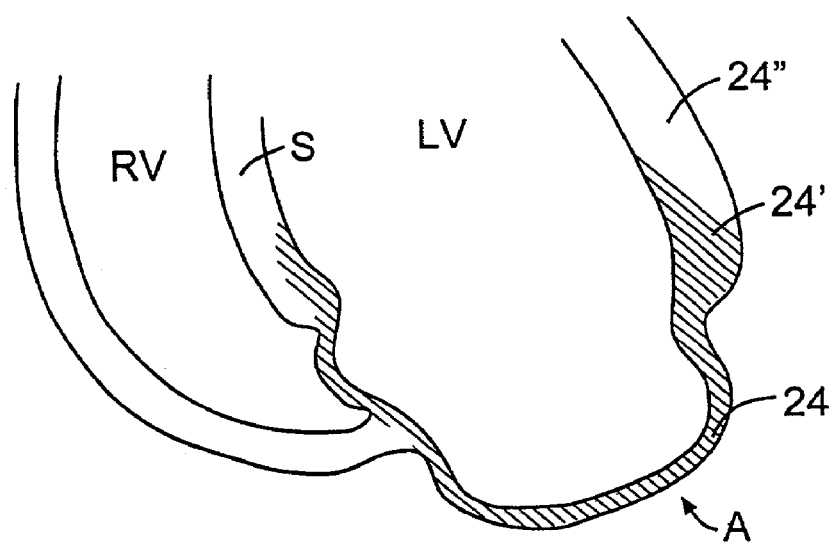
FIG. 55 is a transverse, partial cross-section of left and right ventricles with an aneurysmal region located at an apical portion of the left ventricle and infarcted tissue along the septal wall.

Yet another form of an enclosure member contemplated by the present invention is illustrated in FIG. 54. Enclosure member 65 in FIG. 54 takes the form of a braided ring with a lumen through which tightening cords 66 extend. Enclosure member 65 can be sutured into place surrounding an infarcted zone of tissue, with the sutures passing through enclosure member 65 only and not through tightening cords 66. Once member 65 is secured around the infarcted tissue, tightening cords 66 can be pulled to draw in enclosure member 65, causing the infarcted tissue region to be drawn together to thereby reduce the radius of curvature of the heart wall in that location. Enclosure member 65 may be made of a relatively flexible material that is either atraumatic itself or is wrapped in an atraumatic material such as Dacron or PTFE for example. Other materials that encompass these characteristics are considered to be within the scope of this invention as well.

In treating infarcted tissue and aneurysms with the various inventive methods and devices discussed above, it may be necessary to identify and distinguish between the infarcted tissue regions of the chamber wall and the contractile tissue regions of the chamber wall. Thus, a further aspect of the invention consists of the use of various devices for performing such identification in order to achieve precise placement of the inventive devices, including the splints, sutures, patches, and rings. The identification devices can be used either endocardially, epicardially, or transcardially, depending on which treatment procedure is being performed.

One such method of identifying infarcted tissue regions from contractile tissue regions involves the use of a bipolar electrode. Using the electrode, differences in impedance sensed by the electrode will indicate regions of infarcted versus contractile tissue.

Another method involves the use of fiber optics to distinguish infarcted from contractile regions of tissue. In this case, the fiber optics sense either density or color differences in transmitted or reflected light. Such differences would indicate whether a region contained infarcted tissue or contractile tissue. For instance, a known intensity of light could be directed toward a tissue region, with a known nominal intensity transmitting through contractile tissue regions. Intensities of the transmitted light through the chamber wall could then be measured. Upon sensing a decrease in intensity from the nominal value, the infarcted region could be pinpointed. Border zones also could be sensed in this way by looking for a gradation in transmission differences from the nominal value to a lowest value.

Another method to locate regions of infarcted versus contractile tissue can be employed during the surgical procedure itself. This method involves the injection of radioactive media, such as in a thallium scan, with "real-time" imaging of the radiation during the surgery through the use of a Geiger counter contact probe. Higher observed radiation densities indicate regions of perfused tissue. Yet another injection method uses a visible dye injected into coronary vessels to identify contractile perfused tissue. In this identification technique, the dye travels only to contractile tissue, not to infarcted or scarred tissue regions. Finally TEE, or transesophageal echo ultrasounds may be used to detect regions of infarcted tissue.

Aside from those listed above, other methods are contemplated to locate infarcted tissue regions. For example, the surgeon may use his fingers to probe the outer surface of the chamber wall and feel for differences in the tissue regions.

All of the inventive passive devices to be implanted in the heart may be made of biocompatible material that can remain in the human body indefinitely. Any surface engaging portions of the heart should be atraumatic in order to avoid tissue damage.

It will be understood that this disclosure, in many respects, is only illustrative. Changes may be made in details, particularly in matters of shape, size, material, number and arrangement of parts without exceeding the scope of the invention. Accordingly, the scope of the invention is as defined in the language of the appended claims.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating a heart valve, the method comprising:
   providing a device having an elongate member, the elongate member having a first end and a second end;
   positioning the elongate member transverse a heart chamber associated with the heart valve so as to reposition at least one leaflet associated with the heart valve,
   wherein, when the elongate member is positioned transverse the heart chamber, the elongate member does not contact each of papillary muscles, leaflets, and an annulus associated with the heart valve; and wherein the entire device is positioned solely above an apex of the heart and below an annulus associated with the heart valve.

2. The method of claim 1, further comprising fixing the elongate member in position transverse the heart chamber.

3. The method of claim 2, wherein fixing the elongate member in position includes fixing the elongate member via at least one anchoring mechanism configured to be secured to a wall surrounding the heart chamber.

4. The method of claim 3, wherein the anchoring mechanism is configured to be secured to an exterior surface of the wall.

5. The method of claim 2, wherein an anchoring mechanism is provided on each of the first end and the second end of the elongate member and fixing the elongate member in position includes securing the anchoring mechanisms to portions of a wall surrounding the heart chamber.

6. The method of claim 1, wherein positioning the elongate member includes positioning the elongate member transverse a left ventricle of the heart.

7. The method of claim 1, wherein the valve is a mitral valve.

8. The method of claim 1, wherein positioning the elongate member transverse the heart chamber includes positioning the elongate member so as to avoid internal structures of the heart chamber.

9. The method of claim 1, wherein providing the elongate member includes providing a tension member.

10. The method of claim 1, further comprising reducing a radius of curvature in at least a region of the heart chamber.

11. The method of claim 10, wherein reducing the radius of curvature in at least a region of the heart chamber includes reducing the radius of curvature at one of an aneurysmal and an infracted region of a wall surrounding the heart chamber.

12. A method of treating a heart valve, the method comprising:
providing a device configured to be implanted proximate the heart valve;
implanting the device such that a first portion of the device is positioned external to a heart chamber associated with the valve and closer to a first leaflet of the valve than to a second leaflet of the valve and such that a second portion of the device is positioned external to the heart chamber associated with the valve and closer to the second leaflet of the valve than the first leaflet of the valve; and
repositioning at least one of the first leaflet and the second leaflet of the valve,
wherein, when the device is implanted, the device does not contact each of papillary muscles, leaflets, and an annulus associated with the valve, and wherein the entire device is implanted solely above an apex of the heart and below an annulus associated with the heart valve.

13. The method of claim 12, further comprising drawing the first and second leaflets toward each other.

14. The method of claim 12, wherein the valve is a mitral valve.

15. The method of claim 12, wherein implanting the device includes implanting the device such that the first portion contacts a wall of the heart.

16. The method of claim 15, wherein implanting the device includes implanting the device such that the second portion contacts a wall of the heart.

17. The method of claim 16, wherein the wall surrounds a left ventricle of the heart.

18. The method of claim 16, wherein implanting the device includes implanting the device such that the second portion contacts an exterior surface of the wall of the heart.

19. The method of claim 15, wherein implanting the device includes implanting the device such that the first portion contacts an exterior surface of the wall of the heart.

20. The method of claim 12, wherein providing the device includes providing an elongate member.

21. The method of claim 20, wherein providing the elongate member includes providing a tension member configured to extend transverse a chamber of the heart.

22. The method of claim 20, wherein the elongate member has a first end and a second end and providing the device further includes providing an anchoring mechanism on each of the first end and the second end.

23. The method of claim 22, wherein implanting the device further comprises engaging the anchoring mechanisms with a wall of the heart.

24. The method of claim 22, wherein the first portion and the second portion of the device include the anchoring mechanisms.

25. A method of treating a heart valve having a first leaflet and a second leaflet, the method comprising:
providing a device configured to be implanted proximate the heart valve;
implanting the device such that a first portion of the device contacts heart structure located on a first side of a line defined by an intersection of the first leaflet and the second leaflet and such that a second portion of the device contacts heart structure located on a second side of the line opposite the first side; and
repositioning at least one of the first leaflet and the second leaflet of the valve,
wherein, when the device is implanted, the device does not contact each of papillary muscles, leaflets, and an annulus associated with the valve, and wherein the entire device is implanted solely above an apex of the heart and below an annulus associated with the heart valve.

26. The method of claim 25, further comprising drawing the first leaflet and the second leaflet toward each other.

27. The method of claim 25, wherein the valve is a mitral valve.

28. The method of claim 25, wherein implanting the device includes implanting the device such that the first portion contacts a wall of the heart.

29. The method of claim 28, wherein implanting the device includes implanting the device such that the second portion contacts a wall of the heart.

30. The method of claim 29, wherein the wall surrounds a left ventricle of the heart.

31. The method of claim 29, wherein implanting the device includes implanting the device such that the second portion contacts an exterior surface of the wall of the heart.

32. The method of claim 28, wherein implanting the device includes implanting the device such that the first portion contacts an exterior surface of the wall of the heart.

33. The method of claim 25, wherein providing the device includes providing an elongate member.

34. The method of claim 33, wherein providing the elongate member includes providing a tension member configured to extend transverse a chamber of the heart.

35. The method of claim 33, wherein the elongate member has a first end and a second end and providing the device further includes providing an anchoring mechanism on each of the first end and the second end.

36. The method of claim 35, wherein implanting the device further comprises engaging the anchoring mechanisms with a wall of the heart.

37. The method of claim 35, wherein the first portion and the second portion of the device include the anchoring mechanisms.

* * * * *

UNITED STATES PATENT AND TRADEMARK OFFICE
CERTIFICATE OF CORRECTION

| | |
|---|---|
| PATENT NO. | : 7,189,199 B2 |
| APPLICATION NO. | : 10/136446 |
| DATED | : March 13, 2007 |
| INVENTOR(S) | : Patrick M. McCarthy et al. |

It is certified that error appears in the above-identified patent and that said Letters Patent is hereby corrected as shown below:

Column 32, line 40, replace "lealfets" with --leaflets--.

Signed and Sealed this

First Day of May, 2007

JON W. DUDAS
*Director of the United States Patent and Trademark Office*